United States Patent
Alnemri (12)

(10) Patent No.: US 6,610,541 B2
(45) Date of Patent: Aug. 26, 2003

(54) RECOMBINANT, ACTIVE CASPASES AND USES THEREOF

(75) Inventor: Emad S. Alnemri, Ambler, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/954,697

(22) Filed: Sep. 14, 2001

(65) Prior Publication Data

US 2002/0106631 A1 Aug. 8, 2002

Related U.S. Application Data

(62) Division of application No. 09/227,721, filed on Jan. 8, 1999, now Pat. No. 6,379,950.
(60) Provisional application No. 60/070,987, filed on Jan. 9, 1998.

(51) Int. Cl.[7] .......................... C12N 5/00; C12N 15/00; C07K 1/00; C07H 21/02; C07H 21/04
(52) U.S. Cl. ................... 435/375; 435/69.1; 435/320.1; 435/325; 435/335; 530/350; 530/351; 536/23.1; 536/23.5
(58) Field of Search .............................. 435/69.1, 320.1, 435/325, 455, 375, 335, 6, 7.1; 530/350, 351

(56) References Cited

FOREIGN PATENT DOCUMENTS

| EP | 533 350 A1 | 3/1993 |
|---|---|---|
| WO | WO 95/31535 | 11/1995 |

OTHER PUBLICATIONS

Anderson, "Human Gene Therapy," *Nature* 392: 25–30, 1998.

Srinivasula et al., "Generation of Constitutively Active Recombinant Caspases –3 and –6 by Rearrangement of Their Subunits," *J. Biol. Chem.* 273(17):10107–10111, 1998.

Srinivasula et al., "The Ced–3/Interleukin 1β Converting Enzyme–Like Homolog Mch6 and the Lamin–Cleaving Enzyme Mch2α Are Substrates for the Apoptotic Mediator CPP32," *J. Biol. Chem.* 271(43):27099–27106, 1996.

Touchette, "Gene Therapy: Not Ready for Prime Time," *Nature Medicine* 2(1): 7–8, 1996.

Verma and Somia, "Gene Therapy—Promises, Problems and Prospects," *Nature* 389: 239–242, 1997.

*Primary Examiner*—Jeffrey Fredman
*Assistant Examiner*—Sumesh Kaushal
(74) *Attorney, Agent, or Firm*—Seed Intellectual Property Law Group PLLC

(57) ABSTRACT

Rev-caspases comprising a primary product in which the small subunit is N-terminal to the large subunit are provided. Rev-caspases are used for screening and identifying caspase inhibitors and enhancers. Rev-caspase genes can be delivered to cells for gene therapy.

7 Claims, 36 Drawing Sheets

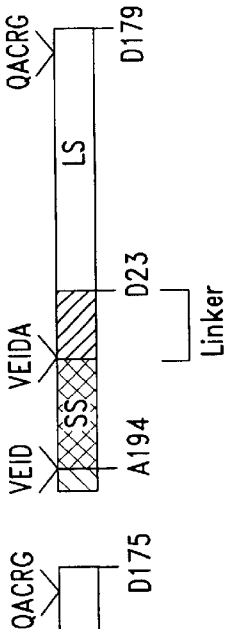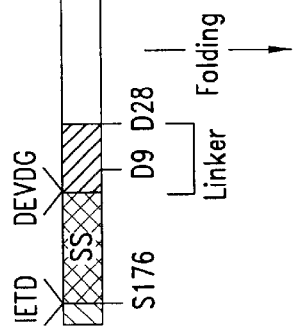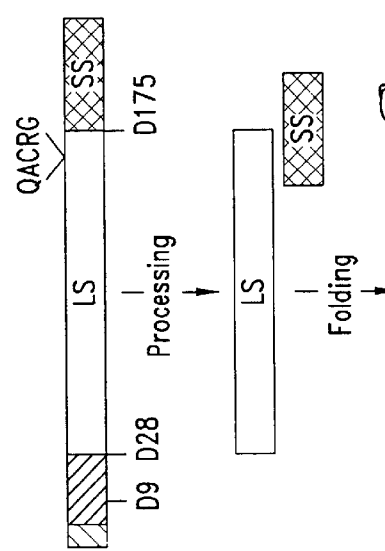
Fig. 1A
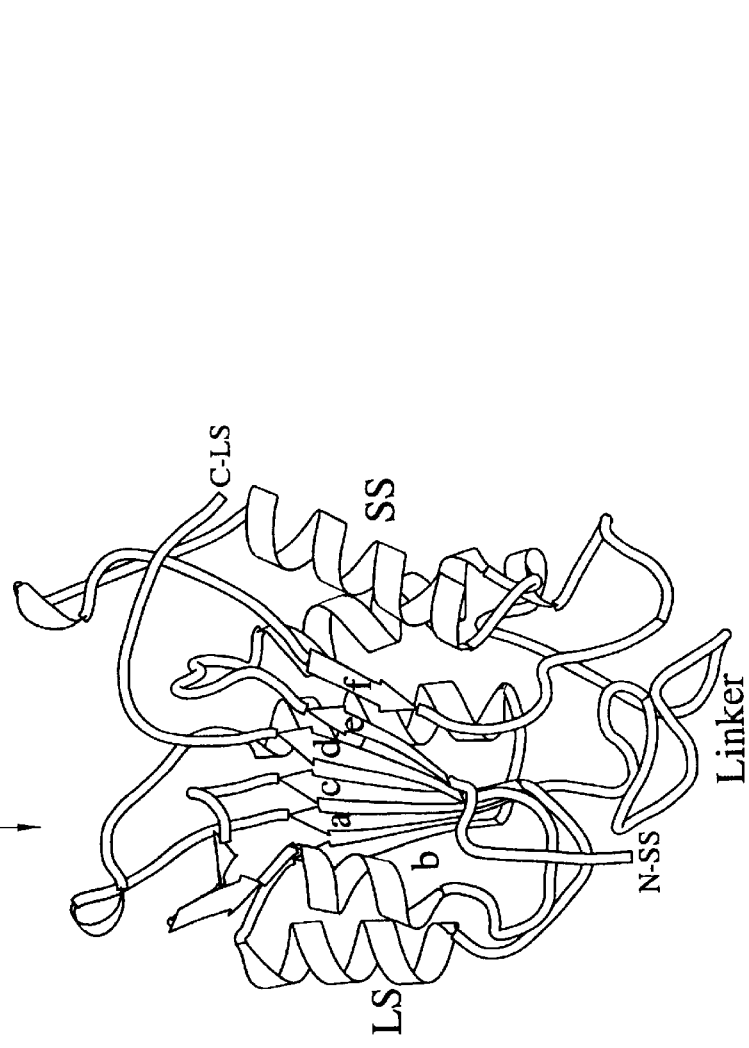
Fig. 1B
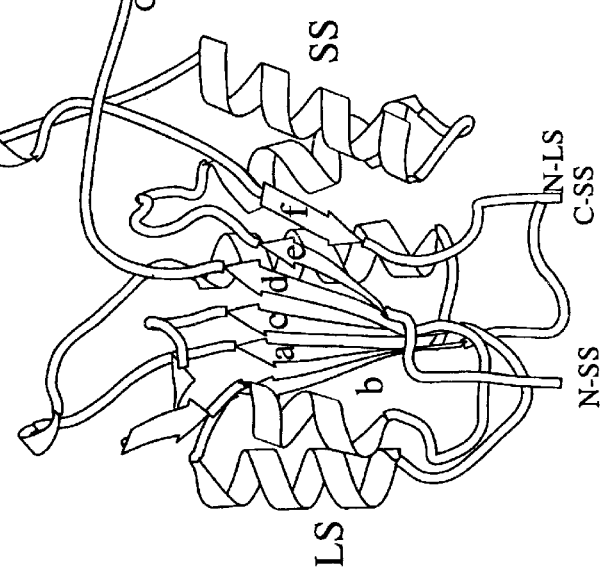
Fig. 1C

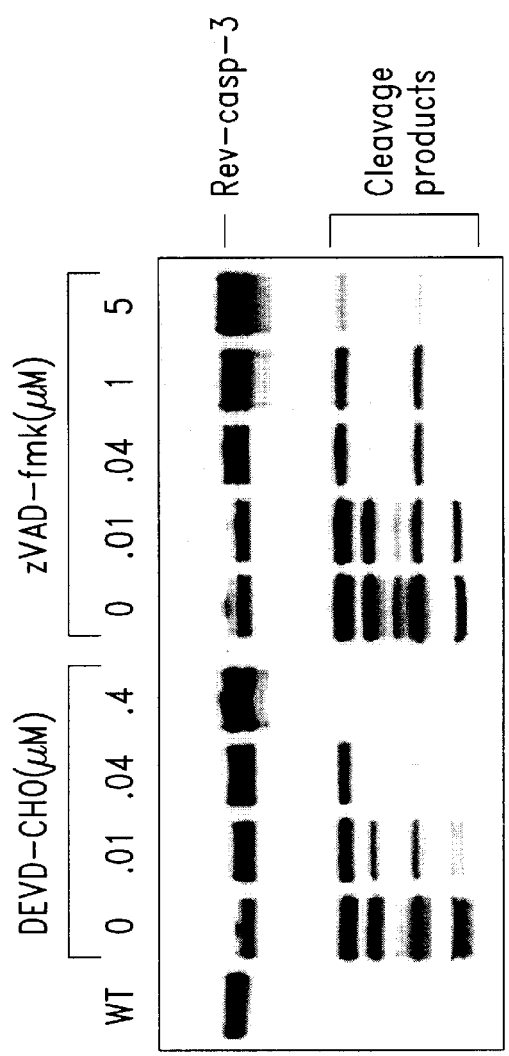
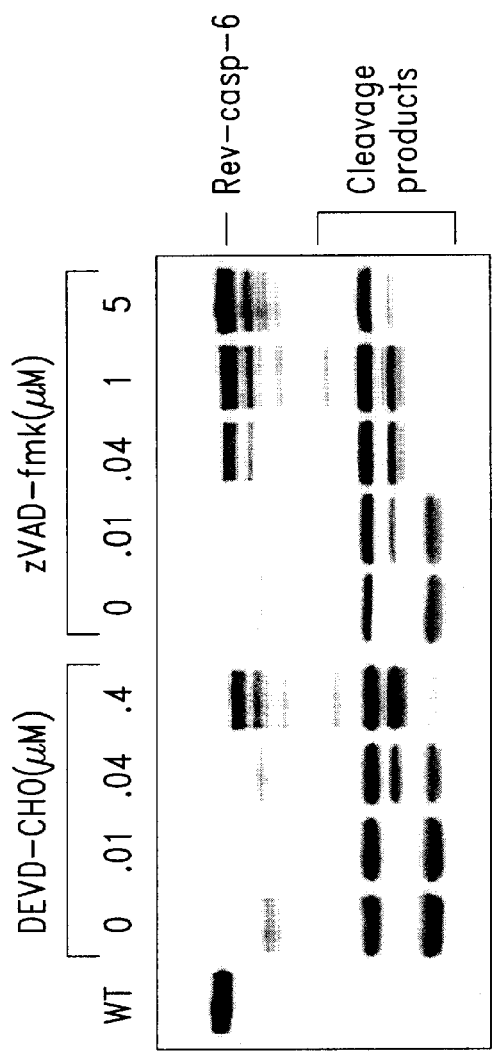
Fig. 2B
Fig. 2C

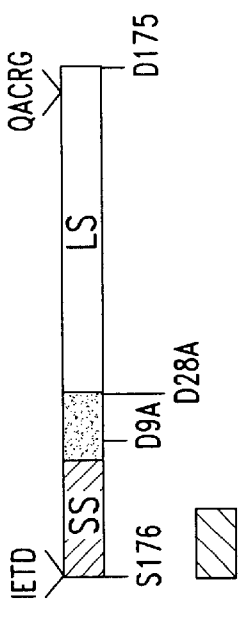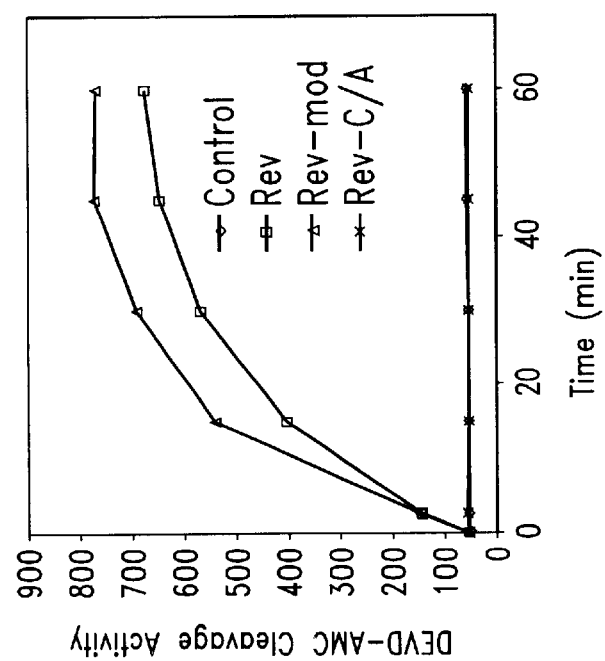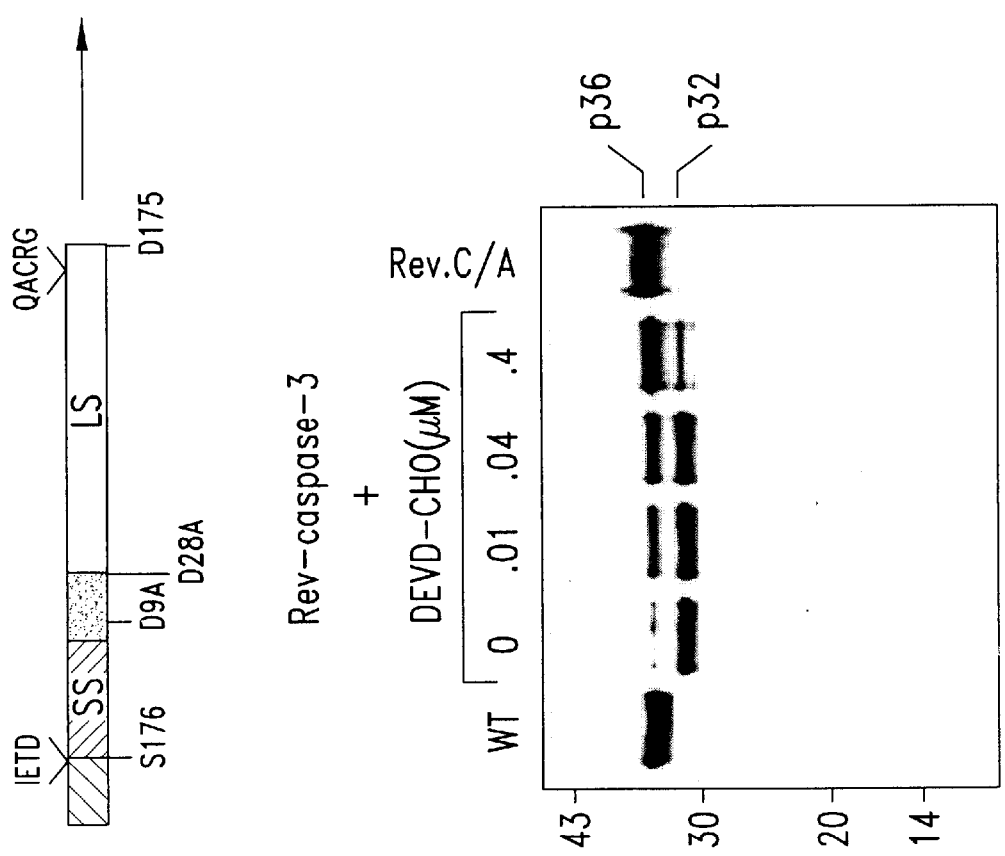
Fig. 5A
Fig. 5B

|       |     | Large Subunit | * |  | Small Subunit |
|-------|-----|---------------|---|--|---------------|
| Mch6  | 178 | RTRTGS..LSHGCQ..FIQACGGEQ..PEPDA..DQLDA..GFVSWRDPKSGSWYV |
| Mch5  | 275 | RDRNGT..LSHGDK..FIQACQGDN..VETDS..LEMDL..NCVSYRNPAEGTWYI |
| Mch4  | 255 | KDRQGT..LTHGRF..FIQACQGEE..IEADA........GYVSFRHVEEGSWYI |
| Mch3  |  85 | GVRNGT..LSHGEE..FIQACRGTE..IQADS.........GYYSWRSPGRGSWFV |
| Mch2  |  62 | PERRGT..LSHGEG..IIQACRGNQ..DVVDN..TEVDA..GYYSHRETVNGSWYI |
| CPP32 |  62 | TSRSGT..LSHGEE..IIQACRGTE..IETDS.........GYYSWRNSKDGSWFI |
| CED-3 | 257 | PTRNGT..LSHGEE..FVQACRGER..DSVDG.........QYVSWRNSARGSWFI |

I

|           |     |                  |                  |                  |
|-----------|-----|------------------|------------------|------------------|
| ICE       | 177 | PRRTGA..MSHGIR..IIQACRGDS..WFKDS..FEDDA..DNVSWRHPTMGSVFI |
| TX        | 150 | PPRNGA..MSHGIL..IVQACRGAN..WVKDS..LEEDA..HNVSWRDSTMGSIFI |
| ICErelIII | 191 | PARNGA..MSHGIL..IVQACRGEK..WVRDS..LEADS..HNVSWRDRTRGSIFI |

II

|       |     |                  |                  |                  |
|-------|-----|------------------|------------------|------------------|
| ICH-1 | 200 | EFRSGG..LSHGVE..FIQACRGDE..DQQDG..EESDA..GTAAMRNTKRGSWYI |
|       |     | b    acc    bac    DX    DX    aaabaa a ba |

III

Rev-Caspase-3
Translation start 1
Translation stop 873

```
  1 ATGATTGAGA CAGACAGTGG TGTTGATGAT GACATGGCGT GTCATAAAAT

51 ACCAGTGGAG GCCGACTTCT TGTATGCATA CTCCACAGCA CCTGGTTATT

101 ATTCTTGGCG AAATTCAAAG GATGGCTCCT GGTTCATCCA GTCGCTTTGT

151 GCCATGCTGA AACAGTATGC CGACAAGCTT GAATTTATGC ACATTCTTAC

201 CCGGGTTAAC CGAAAGGTGG CAACAGAATT TGAGTCCTTT TCCTTTGACG

251 CTACTTTTCA TGCAAAGAAA CAGATTCCAT GTATTGTTTC CATGCTCACA

301 AAAGAACTCT ATTTTTATCA CGATGAAGTT GATGGGGGAT CCCCCATGGA

351 GAACACTGAA AACTCAGTGG ATTCAAAATC CATTAAAAAT TTGGAACCAA

401 AGATCATACA TGGAAGCGAA TCAATGGACT CTGGAATATC CCTGGACAAC

451 AGTTATAAAA TGGATTATCC TGAGATGGGT TTATGTATAA TAATTAATAA

501 TAAGAATTTT CATAAGAGCA CTGGAATGAC ATCTCGGTCT GGTACAGATG

551 TCGATGCAGC AAACCTCAGG GAAACATTCA GAAACTTGAA ATATGAAGTC

601 AGGAATAAAA ATGATCTTAC ACGTGAAGAA ATTGTGGAAT TGATGCGTGA

651 TGTTTCTAAA GAAGATCACA GCAAAAGGAG CAGTTTTGTT TGTGTGCTTC

701 TGAGCCATGG TGAAGAAGGA ATAATTTTTG GAACAAATGG ACCTGTTGAC

751 CTGAAAAAAA TAACAAACTT TTTCAGAGGG GATCGTTGTA GAAGTCTAAC

801 TGGAAAACCC AAACTTTTCA TTATTCAGGC CTGCCGTGGT ACAGAACTGG

851 ACTGTGGCAT TGAGACAGAC TGA
```

Fig. 8A

Uncleavable Rev-caspase-3
Translation start 1
Translation stop 858

```
  1 ATGATTGAGA CAGACAGTGG TGTTGATGAT GACATGGCGT GTCATAAAAT
 51 ACCAGTGGAG GCCGACTTCT TGTATGCATA CTCCACAGCA CCTGGTTATT
101 ATTCTTGGCG AAATTCAAAG GATGGCTCCT GGTTCATCCA GTCGCTTTGT
151 GCCATGCTGA AACAGTATGC CGACAAGCTT GAATTTATGC ACATTCTTAC
201 CCGGGTTAAC CGAAAGGTGG CAACAGAATT TGAGTCCTTT TCCTTTGACG
251 CTACTTTTCA TGCAAAGAAA CAGATTCCAT GTATTGTTTC CATGCTCACA
301 AAAGAACTCT ATTTTTATCA CGGATCCCCC ATGGAGAACA CTGAAAACTC
351 AGTGGCTTCA AAATCCATTA AAAATTTGGA ACCAAAGATC ATACATGGAA
401 GCGAATCAAT GGCCTCTGGA ATATCCCTGG ACAACAGTTA TAAAATGGAT
451 TATCCTGAGA TGGGTTTATG TATAATAATT AATAATAAGA ATTTTCATAA
501 GAGCACTGGA ATGACATCTC GGTCTGGTAC AGATGTCGAT GCAGCAAACC
551 TCAGGGAAAC ATTCAGAAAC TTGAAATATG AAGTCAGGAA TAAAAATGAT
601 CTTACACGTG AAGAAATTGT GGAATTGATG CGTGATGTTT CTAAAGAAGA
651 TCACAGCAAA AGGAGCAGTT TTGTTTGTGT GCTTCTGAGC CATGGTGAAG
701 AAGGAATAAT TTTTGGAACA AATGGACCTG TTGACCTGAA AAAAATAACA
751 AACTTTTTCA GAGGGGATCG TTGTAGAAGT CTAACTGGAA AACCCAAACT
801 TTTCATTATT CAGGCCTGCC GTGGTACAGA ACTGGACTGT GGCATTGAGA
```

851 CAGACTGA

Rev-caspase-6
Translation start 1
Translation stop 903

```
  1 ATGGTAGAAA TAGATGCAGC CTCCGTTTAC ACGCTGCCTG CTGGAGCTGA
 51 CTTCCTCATG TGTTACTCTG TTGCAGAAGG ATATTATTCT CACCGGGAAA
101 CTGTGAACGG CTCATGGTAC ATTCAAGATT TGTGTGAGAT GTTGGGAAAA
151 TATGGCTCCT CCTTAGAGTT CACAGAACTC CTCACACTGG TGAACAGGAA
201 AGTTTCTCAG CGCCGAGTGG ACTTTTGCAA AGACCCAAGT GCAATTGGAA
251 AGAAGCAGGT TCCCTGTTTT GCCTCAATGC TAACTAAAAA GCTGCATTTC
301 TTTCCAAAAT CTAATCTCGA GCACCACCAC CACCACCACG TTGAAATTGA
351 TGGGGGATCC CCCATGAGCT CGGCCTCGGG GCTCCGCAGG GGGCACCCGG
401 CAGGTGGGGA AGAAAACATG ACAGAAACAG ATGCCTTCTA TAAAAGAGAA
451 ATGTTTGATC CGGCAGAAAA GTACAAAATG GACCACAGGA GGAGAGGAAT
501 TGCTTTAATC TTCAATCATG AGAGGTTCTT TTGGCACTTA ACACTGCCAG
551 AAAGGCGGGG CACCTGCGCA GATAGAGACA ATCTTACCCG CAGGTTTTCA
601 GATCTAGGAT TTGAAGTGAA ATGCTTTAAT GATCTTAAAG CAGAAGAACT
651 ACTGCTCAAA ATTCATGAGG TGTCAACTGT TAGCCACGCA GATGCCGATT
701 GCTTTGTGTG TGTCTTCCTG AGCCATGGCG AAGGCAATCA CATTTATGCA
751 TATGATGCTA AAATCGAAAT TCAGACATTA ACTGGCTTGT TCAAAGGAGA
801 CAAGTGTCAC AGCCTGGTTG GAAAACCCAA GATATTTATC ATCCAGGCAT
```

*Fig. 9B*

851 GTCGGGGAAA CCAGCACGAT GTGCCAGTCA TTCCTTTGGA TGTAGTAGAT

901 TAA

| I | SS | P | LS |

| SS | P | LS |

| SS | X | LS |

CASPASE 1

```
  +1  MetAlaAspLysValLeuLysGluLysArgLysLeuPheIleArgSerMetGlyGluGly
      ]------------------------------------------------------------
   1  ATGGCCGACAAGGTCCTGAAGGAGAAGAGAAAGCTGTTTATCCGTTCCATGGGTGAAGGT
      TACCGGCTGTTCCAGGACTTCCTCTTCTCTTTCGACAAATAGGCAAGGTACCCACTTCCA

+1  ThrIleAsnGlyLeuLeuAspGluLeuLeuGlnThrArgValLeuAsnLysGluGluMet
      ------------------------------------------------------------
  61  ACAATAAATGGCTTACTGGATGAATTATTACAGACAAGGGTGCTGAACAAGGAAGAGATG
      TGTTATTTACCGAATGACCTACTTAATAATGTCTGTTCCCACGACTTGTTCCTTCTCTAC

+1  GluLysValLysArgGluAsnAlaThrValMetAspLysThrArgAlaLeuIleAspSer
      ------------------------------------------------------------
 121  GAGAAAGTAAAACGTGAAAATGCTACAGTTATGGATAAGACCCGAGCTTTGATTGACTCC
      CTCTTTCATTTTGCACTTTTACGATGTCAATACCTATTCTGGGCTCGAAACTAACTGAGG

+1  ValIleProLysGlyAlaGlnAlaCysGlnIleCysIleThrTyrIleCysGluGluAsp
      ------------------------------------------------------------
 181  GTTATTCCGAAAGGGGCACAGGCATGCCAAATTTGCATCACATACATTTGTGAAGAAGAC
      CAATAAGGCTTTCCCCGTGTCCGTACGGTTTAAACGTAGTGTATGTAAACACTTCTTCTG

+1  SerTyrLeuAlaGlyThrLeuGlyLeuSerAlaAspGlnThrSerGlyAsnTyrLeuAsn
      ------------------------------------------------------------
 241  AGTTACCTGGCAGGGACGCTGGGACTCTCAGCAGATCAAACATCTGGAAATTACCTTAAT
      TCAATGGACCGTCCCTGCGACCCTGAGAGTCGTCTAGTTTGTAGACCTTTAATGGAATTA

+1  MetGlnAspSerGlnGlyValLeuSerSerPheProAlaProGlnAlaValGlnAspAsn
      ------------------------------------------------------------
 301  ATGCAAGACTCTCAAGGAGTACTTTCTTCCTTTCCAGCTCCTCAGGCAGTGCAGGACAAC
      TACGTTCTGAGAGTTCCTCATGAAAGAAGGAAAGGTCGAGGAGTCCGTCACGTCCTGTTG

+1  ProAlaMetProThrSerSerGlySerGluGlyAsnValLysLeuCysSerLeuGluGlu
      ------------------------------------------------------------
 361  CCAGCTATGCCCACATCCTCAGGCTCAGAAGGGAATGTCAAGCTTTGCTCCCTAGAAGAA
      GGTCGATACGGGTGTAGGAGTCCGAGTCTTCCCTTACAGTTCGAAACGAGGGATCTTCTT

+1  AlaGlnArgIleTrpLysGlnLysSerAlaGluIleTyrProIleMetAspLysSerSer
      ------------------------------------------------------------
 421  GCTCAAAGGATATGGAAACAAAAGTCGGCAGAGATTTATCCAATAATGGACAAGTCAAGC
      CGAGTTTCCTATACCTTTGTTTTCAGCCGTCTCTAAATAGGTTATTACCTGTTCAGTTCG

+1  ArgThrArgLeuAlaLeuIleIleCysAsnGluGluPheAspSerIleProArgArgThr
      ------------------------------------------------------------
 481  CGCACACGTCTTGCTCTCATTATCTGCAATGAAGAATTTGACAGTATTCCTAGAAGAACT
      GCGTGTGCAGAACGAGAGTAATAGACGTTACTTCTTAAACTGTCATAAGGATCTTCTTGA

+1  GlyAlaGluValAspIleThrGlyMetThrMetLeuLeuGlnAsnLeuGlyTyrSerVal
      ------------------------------------------------------------
 541  GGAGCTGAGGTTGACATCACAGGCATGACAATGCTGCTACAAAATCTGGGGTACAGCGTA
      CCTCGACTCCAACTGTAGTGTCCGTACTGTTACGACGATGTTTTAGACCCCATGTCGCAT

+1  AspValLysLysAsnLeuThrAlaSerAspMetThrThrGluLeuGluAlaPheAlaHis
      ------------------------------------------------------------
 601  GATGTGAAAAAAAATCTCACTGCTTCGGACATGACTACAGAGCTGGAGGCATTTGCACAC
      CTACACTTTTTTTTAGAGTGACGAAGCCTGTACTGATGTCTCGACCTCCGTAAACGTGTG
```

Fig. 11B

CASPASE 1

```
   +1  ArgProGluHisLysThrSerAspSerThrPheLeuValPheMetSerHisGlyIleArg
       ------------------------------------------------------------
  661  CGCCCAGAGCACAAGACCTCTGACAGCACGTTCCTGGTGTTCATGTCTCATGGTATTCGG
       GCGGGTCTCGTGTTCTGGAGACTGTCGTGCAAGGACCACAAGTACAGAGTACCATAAGCC

+1  GluGlyIleCysGlyLysLysHisSerGluGlnValProAspIleLeuGlnLeuAsnAla
       ------------------------------------------------------------
  721  GAAGGCATTTGTGGGAAGAAACACTCTGAGCAAGTCCCAGATATACTACAACTCAATGCA
       CTTCCGTAAACACCCTTCTTTGTGAGACTCGTTCAGGGTCTATATGATGTTGAGTTACGT

+1  IlePheAsnMetLeuAsnThrLysAsnCysProSerLeuLysAspLysProLysValIle
       ------------------------------------------------------------
  781  ATCTTTAACATGTTGAATACCAAGAACTGCCCAAGTTTGAAGGACAAACCGAAGGTGATC
       TAGAAATTGTACAACTTATGGTTCTTGACGGGTTCAAACTTCCTGTTTGGCTTCCACTAG

+1  IleIleGlnAlaCysArgGlyAspSerProGlyValValTrpPheLysAspSerValGly
       ------------------------------------------------------------
  841  ATCATCCAGGCCTGCCGTGGTGACAGCCCTGGTGTGGTGTGGTTTAAAGATTCAGTAGGA
       TAGTAGGTCCGGACGGCACCACTGTCGGGACCACACCACACCAAATTTCTAAGTCATCCT

+1  ValSerGlyAsnLeuSerLeuProThrThrGluGluPheGluAspAspAlaIleLysLys
       ------------------------------------------------------------
  901  GTTTCTGGAAACCTATCTTTACCAACTACAGAAGAGTTTGAGGATGATGCTATTAAGAAA
       CAAAGACCTTTGGATAGAAATGGTTGATGTCTTCTCAAACTCCTACTACGATAATTCTTT

+1  AlaHisIleGluLysAspPheIleAlaPheCysSerSerThrProAspAsnValSerTrp
       ------------------------------------------------------------
  961  GCCCACATAGAAAGGATTTTATCGCTTTCTGCTCTTCCACACCAGATAATGTTTCTTGG
       CGGGTGTATCTCTTCCTAAAATAGCGAAAGACGAGAAGGTGTGGTCTATTACAAAGAACC

+1  ArgHisProThrMetGlySerValPheIleGlyArgLeuIleGluHisMetGlnGluTyr
       ------------------------------------------------------------
 1021  AGACATCCCACAATGGGCTCTGTTTTTATTGGAAGACTCATTGAACATATGCAAGAATAT
       TCTGTAGGGTGTTACCCGAGACAAAATAACCTTCTGAGTAACTTGTATACGTTCTTATA

+1  AlaCysSerCysAspValGluGluIlePheArgLysValArgPheSerPheGluGlnPro
       ------------------------------------------------------------
 1081  GCCTGTTCCTGTGATGTGGAGGAAATTTTCCGCAAGGTTCGATTTTCATTTGAGCAGCCA
       CGGACAAGGACACTACACCTCCTTTAAAAGGCGTTCCAAGCTAAAAGTAAACTCGTCGGT

+1  AspGlyArgAlaGlnMetProThrThrGluArgValThrLeuThrArgCysPheTyrLeu
       ------------------------------------------------------------
 1141  GATGGTAGAGCGCAGATGCCCACCACTGAAAGAGTGACTTTGACAAGATGTTTCTACCTC
       CTACCATCTCGCGTCTACGGGTGGTGACTTTCTCACTGAAACTGTTCTACAAAGATGGAG

+1  PheProGlyHis
       ----------->
 1201  TTCCCAGGACATTAA
       AAGGGTCCTGTAATT
```

Fig. 12A

CASPASE 2

```
 +1  MetAlaAlaAspArgGlyArgArgIleLeuGlyValCysGlyMetHisProHisHisGln
     ]------------------------------------------------------------
  1  ATGGCCGCTGACAGGGGACGCAGGATATTGGGAGTGTGTGGCATGCATCCTCATCATCAG
     TACCGGCGACTGTCCCCTGCGTCCTATAACCCTCACACACCGTACGTAGGAGTAGTAGTC
 +1  GluThrLeuLysLysAsnArgValValLeuAlaLysGlnLeuLeuLeuSerGluLeuLeu
     ------------------------------------------------------------
 61  GAAACTCTAAAAAAGAACCGAGTGGTGCTAGCCAAACAGCTGTTGTTGAGCGAATTGTTA
     CTTTGAGATTTTTTCTTGGCTCACCACGATCGGTTTGTCGACAACAACTCGCTTAACAAT
 +1  GluHisLeuLeuGluLysAspIleIleThrLeuGluMetArgGluLeuIleGlnAlaLys
     ------------------------------------------------------------
121  GAACATCTTCTGGAGAAGGACATCATCACCTTGGAAATGAGGGAGCTCATCCAGGCCAAA
     CTTGTAGAAGACCTCTTCCTGTAGTAGTGGAACCTTTACTCCCTCGAGTAGGTCCGGTTT
 +1  ValGlySerPheSerGlnAsnValGluLeuLeuAsnLeuLeuProLysArgGlyProGln
     ------------------------------------------------------------
181  GTGGGCAGTTTCAGCCAGAATGTGGAACTCCTCAACTTGCTGCCTAAGAGGGGTCCCCAA
     CACCCGTCAAAGTCGGTCTTACACCTTGAGGAGTTGAACGACGGATTCTCCCCAGGGGTT
 +1  AlaPheAspAlaPheCysGluAlaLeuArgGluThrLysGlnGlyHisLeuGluAspMet
     ------------------------------------------------------------
241  GCTTTTGATGCCTTCTGTGAAGCACTGAGGGAGACCAAGCAAGGCCACCTGGAGGATATG
     CGAAAACTACGGAAGACACTTCGTGACTCCCTCTGGTTCGTTCCGGTGGACCTCCTATAC
 +1  LeuLeuThrThrLeuSerGlyLeuGlnHisValLeuProProLeuSerCysAspTyrAsp
     ------------------------------------------------------------
301  TTGCTCACCACCCTTTCTGGGCTTCAGCATGTACTCCCACCGTTGAGCTGTGACTACGAC
     AACGAGTGGTGGGAAAGACCCGAAGTCGTACATGAGGGTGGCAACTCGACACTGATGCTG
 +1  LeuSerLeuProPheProValCysGluSerCysProLeuTyrLysLysLeuArgLeuSer
     ------------------------------------------------------------
361  TTGAGTCTCCCTTTTCCGGTGTGTGAGTCCTGTCCCCTTTACAAGAAGCTCCGCCTGTCG
     AACTCAGAGGGAAAAGGCCACACACTCAGGACAGGGGAAATGTTCTTCGAGGCGGACAGC
 +1  ThrAspThrValGluHisSerLeuAspAsnLysAspGlyProValCysLeuGlnValLys
     ------------------------------------------------------------
421  ACAGATACTGTGGAACACTCCCTAGACAATAAAGATGGTCCTGTCTGCCTTCAGGTGAAG
     TGTCTATGACACCTTGTGAGGGATCTGTTATTTCTACCAGGACAGACGGAAGTCCACTTC
 +1  ProCysThrProGluPheTyrGlnThrHisPheGlnLeuAlaTyrArgLeuGlnSerArg
     ------------------------------------------------------------
481  CCTTGCACTCCTGAATTTTATCAAACACACTTCCAGCTGGCATATAGGTTGCAGTCTCGG
     GGAACGTGAGGACTTAAAATAGTTTGTGTGAAGGTCGACCGTATATCCAACGTCAGAGCC
 +1  ProArgGlyLeuAlaLeuValLeuSerAsnValHisPheThrGlyGluLysGluLeuGlu
     ------------------------------------------------------------
541  CCTCGTGGCCTAGCACTGGTGTTGAGCAATGTGCACTTCACTGGAGAGAAAGAACTGGAA
     GGAGCACCGGATCGTGACCACAACTCGTTACACGTGAAGTGACCTCTCTTTCTTGACCTT
 +1  PheArgSerGlyGlyAspValAspHisSerThrLeuValThrLeuPheLysLeuLeuGly
     ------------------------------------------------------------
601  TTTCGCTCTGGAGGGGATGTGGACCACAGTACTCTAGTCACCCTCTTCAAGCTTTTGGGC
     AAAGCGAGACCTCCCCTACACCTGGTGTCATGAGATCAGTGGGAGAAGTTCGAAAACCCG
```

Fig. 12B

CASPASE 2

```
  +1  TyrAspValHisValLeuCysAspGlnThrAlaGlnGluMetGlnGluLysLeuGlnAsn
      ------------------------------------------------------------
 661  TATGACGTCCATGTTCTATGTGACCAGACTGCACAGGAAATGCAAGAGAAACTGCAGAAT
      ATACTGCAGGTACAAGATACACTGGTCTGACGTGTCCTTTACGTTCTCTTTGACGTCTTA
  +1  PheAlaGlnLeuProAlaHisArgValThrAspSerCysIleValAlaLeuLeuSerHis
      ------------------------------------------------------------
 721  TTTGCACAGTTACCTGCACACCGAGTCACGGACTCCTGCATCGTGGCACTCCTCTCGCAT
      AAACGTGTCAATGGACGTGTGGCTCAGTGCCTGAGGACGTAGCACCGTGAGGAGAGCGTA
  +1  GlyValGluGlyAlaIleTyrGlyValAspGlyLysLeuLeuGlnLeuGlnGluValPhe
      ------------------------------------------------------------
 781  GGTGTGGAGGGCGCCATCTATGGTGTGGATGGGAAACTGCTCCAGCTCCAAGAGGTTTTT
      CCACACCTCCCGCGGTAGATACCACACCTACCCTTTGACGAGGTCGAGGTTCTCCAAAAA
  +1  GlnLeuPheAspAsnAlaAsnCysProSerLeuGlnAsnLysProLysMetPhePheIle
      ------------------------------------------------------------
 841  CAGCTCTTTGACAACGCCAACTGCCCAAGCCTACAGAACAAACCAAAAATGTTCTTCATC
      GTCGAGAAACTGTTGCGGTTGACGGGTTCGGATGTCTTGTTTGGTTTTTACAAGAAGTAG
  +1  GlnAlaCysArgGlyAspGluThrAspArgGlyValAspGlnGlnAspGlyLysAsnHis
      ------------------------------------------------------------
 901  CAGGCCTGCCGTGGAGATGAGACTGATCGTGGGGTTGACCAACAAGATGGAAAGAACCAC
      GTCCGGACGGCACCTCTACTCTGACTAGCACCCCAACTGGTTGTTCTACCTTTCTTGGTG
  +1  AlaGlySerProGlyCysGluGluSerAspAlaGlyLysGluLysLeuProLysMetArg
      ------------------------------------------------------------
 961  GCAGGATCCCCTGGGTGCGAGGAGAGTGATGCCGGTAAAGAAAAGTTGCCGAAGATGAGA
      CGTCCTAGGGGACCCACGCTCCTCTCACTACGGCCATTTCTTTTCAACGGCTTCTACTCT
  +1  LeuProThrArgSerAspMetIleCysGlyTyrAlaCysLeuLysGlyThrAlaAlaMet
      ------------------------------------------------------------
1021  CTGCCCACGCGCTCAGACATGATATGCGGCTATGCCTGCCTCAAAGGGACTGCCGCCATG
      GACGGGTGCGCGAGTCTGTACTATACGCCGATACGGACGGAGTTTCCCTGACGGCGGTAC
  +1  ArgAsnThrLysArgGlySerTrpTyrIleGluAlaLeuAlaGlnValPheSerGluArg
      ------------------------------------------------------------
1081  CGGAACACCAAACGAGGTTCCTGGTACATCGAGGCTCTTGCTCAAGTGTTTTCTGAGCGG
      GCCTTGTGGTTTGCTCCAAGGACCATGTAGCTCCGAGAACGAGTTCACAAAAGACTCGCC
  +1  AlaCysAspMetHisValAlaAspMetLeuValLysValAsnAlaLeuIleLysAspArg
      ------------------------------------------------------------
1141  GCTTGTGATATGCACGTGGCCGACATGCTGGTTAAGGTGAACGCACTTATCAAGGATCGG
      CGAACACTATACGTGCACCGGCTGTACGACCAATTCCACTTGCGTGAATAGTTCCTAGCC
  +1  GluGlyTyrAlaProGlyThrGluPheHisArgCysLysGluMetSerGluTyrCysSer
      ------------------------------------------------------------
1201  GAAGGTTATGCTCCTGGCACAGAATTCCACCGGTGCAAGGAAATGTCTGAATACTGCAGC
      CTTCCAATACGAGGACCGTGTCTTAAGGTGGCCACGTTCCTTTACAGACTTATGACGTCG
  +1  ThrLeuCysArgHisLeuTyrLeuPheProGlyHisProProThr
      --------------------------------------------->
1261  ACTCTGTGCCGCCACCTCTACCTGTTCCCAGGACACCCTCCCACATGA
      TGAGACACGGCGGTGGAGATGGACAAGGGTCCTGTGGGAGGGTGTACT
```

Fig. 13A

CASPASE 3

```
  +1  MetGluAsnThrGluAsnSerValAspSerLysSerIleLysAsnLeuGluProLysIle
      ]-------------------------------------------------------------
   1  ATGGAGAACACTGAAAACTCAGTGGATTCAAAATCCATTAAAAATTTGGAACCAAAGATC
      TACCTCTTGTGACTTTTGAGTCACCTAAGTTTTAGGTAATTTTTAAACCTTGGTTTCTAG

+1  IleHisGlySerGluSerMetAspSerGlyIleSerLeuAspAsnSerTyrLysMetAsp
      -------------------------------------------------------------
  61  ATACATGGAAGCGAATCAATGGACTCTGGAATATCCCTGGACAACAGTTATAAAATGGAT
      TATGTACCTTCGCTTAGTTACCTGAGACCTTATAGGGACCTGTTGTCAATATTTTACCTA

+1  TyrProGluMetGlyLeuCysIleIleIleAsnAsnLysAsnPheHisLysSerThrGly
      -------------------------------------------------------------
 121  TATCCTGAGATGGGTTTATGTATAATAATTAATAATAAGAATTTTCATAAAAGCACTGGA
      ATAGGACTCTACCCAAATACATATTATTAATTATTATTCTTAAAAGTATTTTCGTGACCT

+1  MetThrSerArgSerGlyThrAspValAspAlaAlaAsnLeuArgGluThrPheArgAsn
      -------------------------------------------------------------
 181  ATGACATCTCGGTCTGGTACAGATGTCGATGCAGCAAACCTCAGGGAAACATTCAGAAAC
      TACTGTAGAGCCAGACCATGTCTACAGCTACGTCGTTTGGAGTCCCTTTGTAAGTCTTTG

+1  LeuLysTyrGluValArgAsnLysAsnAspLeuThrArgGluGluIleValGluLeuMet
      -------------------------------------------------------------
 241  TTGAAATATGAAGTCAGGAATAAAAATGATCTTACACGTGAAGAAATTGTGGAATTGATG
      AACTTTATACTTCAGTCCTTATTTTTACTAGAATGTGCACTTCTTTAACACCTTAACTAC

+1  ArgAspValSerLysGluAspHisSerLysArgSerSerPheValCysValLeuLeuSer
      -------------------------------------------------------------
 301  CGTGATGTTTCTAAAGAAGATCACAGCAAAAGGAGCAGTTTTGTTTGTGTGCTTCTGAGC
      GCACTACAAAGATTTCTTCTAGTGTCGTTTTCCTCGTCAAAACAAACACACGAAGACTCG

+1  HisGlyGluGluGlyIleIlePheGlyThrAsnGlyProValAspLeuLysLysIleThr
      -------------------------------------------------------------
 361  CATGGTGAAGAAGGAATAATTTTTGGAACAAATGGACCTGTTGACCTGAAAAAAATAACA
      GTACCACTTCTTCCTTATTAAAAACCTTGTTTACCTGGACAACTGGACTTTTTTTATTGT

+1  AsnPhePheArgGlyAspArgCysArgSerLeuThrGlyLysProLysLeuPheIleIle
      -------------------------------------------------------------
 421  AACTTTTTCAGAGGGGATCGTTGTAGAAGTCTAACTGGAAAACCCAAACTTTTCATTATT
      TTGAAAAAGTCTCCCCTAGCAACATCTTCAGATTGACCTTTTGGGTTTGAAAAGTAATAA

+1  GlnAlaCysArgGlyThrGluLeuAspCysGlyIleGluThrAspSerGlyValAspAsp
      -------------------------------------------------------------
 481  CAGGCCTGCCGTGGTACAGAACTGGACTGTGGCATTGAGACAGACAGTGGTGTTGATGAT
      GTCCGGACGGCACCATGTCTTGACCTGACACCGTAACTCTGTCTGTCACCACAACTACTA

+1  AspMetAlaCysHisLysIleProValAspAlaAspPheLeuTyrAlaTyrSerThrAla
      -------------------------------------------------------------
 541  GACATGGCGTGTCATAAAATACCAGTGGATGCCGACTTCTTGTATGCATACTCCACAGCA
      CTGTACCGCACAGTATTTTATGGTCACCTACGGCTGAAGAACATACGTATGAGGTGTCGT

+1  ProGlyTyrTyrSerTrpArgAsnSerLysAspGlySerTrpPheIleGlnSerLeuCys
      -------------------------------------------------------------
 601  CCTGGTTATTATTCTTGGCGAAATTCAAAGGATGGCTCCTGGTTCATCCAGTCGCTTTGT
      GGACCAATAATAAGAACCGCTTTAAGTTTCCTACCGAGGACCAAGTAGGTCAGCGAAACA
```

Fig. 13B

CASPASE 3

```
    +1  AlaMetLeuLysGlnTyrAlaAspLysLeuGluPheMetHisIleLeuThrArgValAsn
        ------------------------------------------------------------
   661  GCCATGCTGAAACAGTATGCCGACAAGCTTGAATTTATGCACATTCTTACCCGGGTTAAC
        CGGTACGACTTTGTCATACGGCTGTTCGAACTTAAATACGTGTAAGAATGGGCCCAATTG
    +1  ArgLysValAlaThrGluPheGluSerPheSerPheAspAlaThrPheHisAlaLysLys
        ------------------------------------------------------------
   721  CGAAAGGTGGCAACAGAATTTGAGTCCTTTTCCTTTGACGCTACTTTTCATGCAAAGAAA
        GCTTTCCACCGTTGTCTTAAACTCAGGAAAAGGAAACTGCGATGAAAAGTACGTTTCTTT
    +1  GlnIleProCysIleValSerMetLeuThrLysGluLeuTyrPheTyrHis
        --------------------------------------------------->
   781  CAGATTCCATGTATTGTTTCCATGCTCACAAAAGAACTCTATTTTTATCACTAAN
        GTCTAAGGTACATAACAAAGGTACGAGTGTTTCTTGAGATAAAAATAGTGATTN
```

Fig. 14A

CASPASE 4

```
 +1  MetAlaGluGlyAsnHisArgLysLysProLeuLysValLeuGluSerLeuGlyLysAsp
     ]------------------------------------------------------------
  1  ATGGCAGAAGGCAACCACAGAAAAAAGCCACTTAAGGTGTTGGAATCCCTGGGCAAAGAT
     TACCGTCTTCCGTTGGTGTCTTTTTTCGGTGAATTCCACAACCTTAGGGACCCGTTTCTA

+1  PheLeuThrGlyValLeuAspAsnLeuValGluGlnAsnValLeuAsnTrpLysGluGlu
     ------------------------------------------------------------
 61  TTCCTCACTGGTGTTTTGGATAACTTGGTGGAACAAAATGTACTGAACTGGAAGGAAGAG
     AAGGAGTGACCACAAAACCTATTGAACCACCTTGTTTTACATGACTTGACCTTCCTTCTC

+1  GluLysLysLysTyrTyrAspAlaLysThrGluAspLysValArgValMetAlaAspSer
     ------------------------------------------------------------
121  GAAAAAAGAAATATTACGATGCTAAAACTGAAGACAAAGTTCGGGTCATGGCAGACTCT
     CTTTTTTTCTTTATAATGCTACGATTTTGACTTCTGTTTCAAGCCCAGTACCGTCTGAGA

+1  MetGlnGluLysGlnArgMetAlaGlyGlnMetLeuLeuGlnThrPhePheAsnIleAsp
     ------------------------------------------------------------
181  ATGCAAGAGAAGCAACGTATGGCAGGACAAATGCTTCTTCAAACCTTTTTTAACATAGAC
     TACGTTCTCTTCGTTGCATACCGTCCTGTTTACGAAGAAGTTTGGAAAAAATTGTATCTG

+1  GlnIleSerProAsnLysLysAlaHisProAsnMetGluAlaGlyProProGluSerGly
     ------------------------------------------------------------
241  CAAATATCCCCCAATAAAAAAGCTCATCCGAATATGGAGGCTGGACCACCTGAGTCAGGA
     GTTTATAGGGGGTTATTTTTTCGAGTAGGCTTATACCTCCGACCTGGTGGACTCAGTCCT

+1  GluSerThrAspAlaLeuLysLeuCysProHisGluGluPheLeuArgLeuCysLysGlu
     ------------------------------------------------------------
301  GAATCTACAGATGCCCTCAAGCTTTGTCCTCATGAAGAATTCCTGAGACTATGTAAAGAA
     CTTAGATGTCTACGGGAGTTCGAAACAGGAGTACTTCTTAAGGACTCTGATACATTTCTT

+1  ArgAlaGluGluIleTyrProIleLysGluArgAsnAsnArgThrArgLeuAlaLeuIle
     ------------------------------------------------------------
361  AGAGCTGAAGAGATCTATCCAATAAAGGAGAGAAACAACCGCACACGCCTGGCTCTCATC
     TCTCGACTTCTCTAGATAGGTTATTTCCTCTCTTGTTGGCGTGTGCGGACCGAGAGTAG

+1  IleCysAsnThrGluPheAspHisLeuProProArgAsnGlyAlaAspPheAspIleThr
     ------------------------------------------------------------
421  ATATGCAATACAGAGTTTGACCATCTGCCTCCGAGGAATGGAGCTGACTTTGACATCACA
     TATACGTTATGTCTCAAACTGGTAGACGGAGGCTCCTTACCTCGACTGAAACTGTAGTGT

+1  GlyMetLysGluLeuLeuGluGlyLeuAspTyrSerValAspValGluGluAsnLeuThr
     ------------------------------------------------------------
481  GGGATGAAGGAGCTACTTGAGGGTCTGGACTATAGTGTAGATGTAGAAGAGAATCTGACA
     CCCTACTTCCTCGATGAACTCCCAGACCTGATATCACATCTACATCTTCTCTTAGACTGT

+1  AlaArgAspMetGluSerAlaLeuArgAlaPheAlaThrArgProGluHisLysSerSer
     ------------------------------------------------------------
541  GCCAGGGATATGGAGTCAGCGCTGAGGGCATTTGCTACCAGACCAGAGCACAAGTCCTCT
     CGGTCCCTATACCTCAGTCGCGACTCCCGTAAACGATGGTCTGGTCTCGTGTTCAGGAGA

+1  AspSerThrPheLeuValLeuMetSerHisGlyIleLeuGluGlyIleCysGlyThrVal
     ------------------------------------------------------------
601  GACAGCACATTCTTGGTACTCATGTCTCATGGCATCCTGGAGGGAATCTGCGGAACTGTG
     CTGTCGTGTAAGAACCATGAGTACAGAGTACCGTAGGACCTCCCTTAGACGCCTTGACAC
```

Fig. 14B

CASPASE 4

```
   +1  HisAspGluLysLysProAspValLeuLeuTyrAspThrIlePheGlnIlePheAsnAsn
       ------------------------------------------------------------
  661  CATGATGAGAAAAAACCAGATGTGCTGCTTTATGACACCATCTTCCAGATATTCAACAAC
       GTACTACTCTTTTTTGGTCTACACGACGAAATACTGTGGTAGAAGGTCTATAAGTTGTTG

+1  ArgAsnCysLeuSerLeuLysAspLysProLysValIleIleValGlnAlaCysArgGly
       ------------------------------------------------------------
  721  CGCAACTGCCTCAGTCTGAAGGACAAACCCAAGGTCATCATTGTCCAGGCCTGCAGAGGT
       GCGTTGACGGAGTCAGACTTCCTGTTTGGGTTCCAGTAGTAACAGGTCCGGACGTCTCCA

+1  AlaAsnArgGlyGluLeuTrpValArgAspSerProAlaSerLeuGluValAlaSerSer
       ------------------------------------------------------------
  781  GCAAACCGTGGGGAACTGTGGGTCAGAGACTCTCCAGCATCCTTGGAAGTGGCCTCTTCA
       CGTTTGGCACCCCTTGACACCCAGTCTCTGAGAGGTCGTAGGAACCTTCACCGGAGAAGT

+1  GlnSerSerGluAsnLeuGluGluAspAlaValTyrLysThrHisValGluLysAspPhe
       ------------------------------------------------------------
  841  CAGTCATCTGAGAACCTGGAGGAAGATGCTGTTTACAAGACCCACGTGGAGAAGGACTTC
       GTCAGTAGACTCTTGGACCTCCTTCTACGACAAATGTTCTGGGTGCACCTCTTCCTGAAG

+1  IleAlaPheCysSerSerThrProHisAsnValSerTrpArgAspSerThrMetGlySer
       ------------------------------------------------------------
  901  ATTGCTTTCTGCTCTTCAACGCCACACAACGTGTCCTGGAGAGACAGCACAATGGGCTCT
       TAACGAAAGACGAGAAGTTGCGGTGTGTTGCACAGGACCTCTCTGTCGTGTTACCCGAGA

+1  IlePheIleThrGlnLeuIleThrCysPheGlnLysTyrSerTrpCysCysHisLeuGlu
       ------------------------------------------------------------
  961  ATCTTCATCACACAACTCATCACATGCTTCCAGAAATATTCTTGGTGCTGCCACCTAGAG
       TAGAAGTAGTGTGTTGAGTAGTGTACGAAGGTCTTTATAAGAACCACGACGGTGGATCTC

+1  GluValPheArgLysValGlnGlnSerPheGluThrProArgAlaLysAlaGlnMetPro
       ------------------------------------------------------------
 1021  GAAGTATTTCGGAAGGTACAGCAATCATTTGAAACTCCAAGGGCCAAAGCTCAAATGCCC
       CTTCATAAAGCCTTCCATGTCGTTAGTAAACTTTGAGGTTCCCGGTTTCGAGTTTACGGG

+1  ThrIleGluArgLeuSerMetThrArgTyrPheTyrLeuPheProGlyAsn
       --------------------------------------------------->
 1081  ACCATAGAACGACTGTCCATGACAAGATATTTCTACCTCTTTCCTGGCAATTGA
       TGGTATCTTGCTGACAGGTACTGTTCTATAAAGATGGAGAAAGGACCGTTAACT
```

Fig. 15A

CASPASE 5

```
 +1 MetPheLysGlyIleLeuGlnSerGlyLeuAspAsnPheValIleAsnHisMetLeuLys
    ]------------------------------------------------------------
  1 ATGTTCAAAGGTATCCTTCAGAGTGGATTGGATAACTTCGTGATAAACCACATGCTAAAG
    TACAAGTTTCCATAGGAAGTCTCACCTAACCTATTGAAGCACTATTTGGTGTACGATTTC
 +1 AsnAsnValAlaGlyGlnThrSerIleGlnThrLeuValProAsnThrAspGlnLysSer
    ------------------------------------------------------------
 61 AACAACGTGGCTGGACAAACATCTATCCAGACCCTAGTACCTAATACGGATCAAAAGTCG
    TTGTTGCACCGACCTGTTTGTAGATAGGTCTGGGATCATGGATTATGCCTAGTTTTCAGC
 +1 ThrSerValLysLysAspAsnHisLysLysLysThrValLysMetLeuGluTyrLeuGly
    ------------------------------------------------------------
121 ACCAGTGTAAAAAAAGACAACCACAAAAAAAAAACAGTTAAGATGTTGGAATACCTGGGC
    TGGTCACATTTTTTTCTGTTGGTGTTTTTTTTTGTCAATTCTACAACCTTATGGACCCG
 +1 LysAspValLeuHisGlyValPheAsnTyrLeuAlaLysHisAspValLeuThrLeuLys
    ------------------------------------------------------------
181 AAAGATGTTCTTCATGGTGTTTTTAATTATTTGGCAAAACACGATGTTCTGACATTGAAG
    TTTCTACAAGAAGTACCACAAAAATTAATAAACCGTTTTGTGCTACAAGACTGTAACTTC
 +1 GluGluGluLysLysLysTyrTyrAspAlaLysIleGluAspLysAlaLeuIleLeuVal
    ------------------------------------------------------------
241 GAAGAGGAAAAGAAAAAATATTATGATGCCAAAATTGAAGACAAGGCCCTGATCTTGGTA
    CTTCTCCTTTTCTTTTTATAATACTACGGTTTTAACTTCTGTTCCGGGACTAGAACCAT
 +1 AspSerLeuArgLysAsnArgValAlaHisGlnMetPheThrGlnThrLeuLeuAsnMet
    ------------------------------------------------------------
301 GACTCTTTGCGAAAGAATCGCGTGGCTCATCAAATGTTTACCCAAACACTTCTCAATATG
    CTGAGAAACGCTTTCTTAGCGCACCGAGTAGTTTACAAATGGGTTTGTGAAGAGTTATAC
 +1 AspGlnLysIleThrSerValLysProLeuLeuGlnIleGluAlaGlyProProGluSer
    ------------------------------------------------------------
361 GACCAAAAGATCACCAGTGTAAAACCTCTTCTGCAAATCGAGGCTGGACCACCTGAGTCA
    CTGGTTTTCTAGTGGTCACATTTTGGAGAAGACGTTTAGCTCCGACCTGGTGGACTCAGT
 +1 AlaGluSerThrAsnIleLeuLysLeuCysProArgGluGluPheLeuArgLeuCysLys
    ------------------------------------------------------------
421 GCAGAATCTACAAATATACTCAAACTTTGTCCTCGTGAAGAATTCCTGAGACTGTGTAAA
    CGTCTTAGATGTTTATATGAGTTTGAAACAGGAGCACTTCTTAAGGACTCTGACACATTT
 +1 LysAsnHisAspGluIleTyrProIleLysLysArgGluAspArgArgArgLeuAlaLeu
    ------------------------------------------------------------
481 AAAAATCATGATGAGATCTATCCAATAAAAAAGAGAGAGGACCGCAGACGCCTGGCTCTC
    TTTTTAGTACTACTCTAGATAGGTTATTTTTTCTCTCTCCTGGCGTCTGCGGACCGAGAG
 +1 IleIleCysAsnThrLysPheAspHisLeuProAlaArgAsnGlyAlaHisTyrAspIle
    ------------------------------------------------------------
541 ATCATATGCAATACAAAGTTTGATCACCTGCCTGCAAGGAATGGGGCTCACTATGACATC
    TAGTATACGTTATGTTTCAAACTAGTGGACGGACGTTCCTTACCCCGAGTGATACTGTAG
 +1 ValGlyMetLysArgLeuLeuGlnGlyLeuGlyTyrThrValValAspGluLysAsnLeu
    ------------------------------------------------------------
601 GTGGGGATGAAAAGGCTGCTTCAAGGCCTGGGCTACACTGTGGTTGACGAAAAGAATCTC
    CACCCCTACTTTTCCGACGAAGTTCCGGACCCGATGTGACACCAACTGCTTTTCTTAGAG
```

Fig. 15B

CASPASE 5

```
 +1  ThrAlaArgAspMetGluSerValLeuArgAlaPheAlaAlaArgProGluHisLysSer
     ------------------------------------------------------------
661  ACAGCCAGGGATATGGAGTCAGTGCTGAGGGCATTTGCTGCCAGACCAGAGCACAAGTCC
     TGTCGGTCCCTATACCTCAGTCACGACTCCCGTAAACGACGGTCTGGTCTCGTGTTCAGG

+1  SerAspSerThrPheLeuValLeuMetSerHisGlyIleLeuGluGlyIleCysGlyThr
     ------------------------------------------------------------
721  TCTGACAGCACGTTCTTGGTACTCATGTCTCATGGCATCCTAGAGGGAATCTGCGGAACT
     AGACTGTCGTGCAAGAACCATGAGTACAGAGTACCGTAGGATCTCCCTTAGACGCCTTGA

+1  AlaHisLysLysLysLysProAspValLeuLeuTyrAspThrIlePheGlnIlePheAsn
     ------------------------------------------------------------
781  GCGCATAAAAAGAAAAAACCGGATGTGCTGCTTTATGACACCATCTTCCAGATATTCAAC
     CGCGTATTTTTCTTTTTTGGCCTACACGACGAAATACTGTGGTAGAAGGTCTATAAGTTG

+1  AsnArgAsnCysLeuSerLeuLysAspLysProLysValIleIleValGlnAlaCysArg
     ------------------------------------------------------------
841  AACCGCAACTGCCTCAGTCTAAAGGACAAACCCAAGGTCATCATTGTCCAGGCCTGCAGA
     TTGGCGTTGACGGAGTCAGATTTCCTGTTTGGGTTCCAGTAGTAACAGGTCCGGACGTCT

+1  GlyGluLysHisGlyGluLeuTrpValArgAspSerProAlaSerLeuAlaValIleSer
     ------------------------------------------------------------
901  GGTGAAAAACATGGGGAACTCTGGGTCAGAGACTCTCCAGCATCCTTGGCAGTCATCTCT
     CCACTTTTTGTACCCCTTGAGACCCAGTCTCTGAGAGGTCGTAGGAACCGTCAGTAGAGA

+1  SerGlnSerSerGluAsnLeuGluAlaAspSerValCysLysIleHisGluGluLysAsp
     ------------------------------------------------------------
961  TCACAGTCATCTGAGAACCTGGAGGCAGATTCTGTTTGCAAGATCCACGAGGAGAAGGAC
     AGTGTCAGTAGACTCTTGGACCTCCGTCTAAGACAAACGTTCTAGGTGCTCCTCTTCCTG

+1  PheIleAlaPheCysSerSerThrProHisAsnValSerTrpArgAspArgThrArgGly
     ------------------------------------------------------------
1021 TTCATTGCTTTCTGTTCTTCAACACCACATAACGTGTCCTGGAGAGACCGCACAAGGGGC
     AAGTAACGAAAGACAAGAAGTTGTGGTGTATTGCACAGGACCTCTCTGGCGTGTTCCCCG

+1  SerIlePheIleThrGluLeuIleThrCysPheGlnLysTyrSerCysCysCysHisLeu
     ------------------------------------------------------------
1081 TCCATCTTCATTACGGAACTCATCACATGCTTCCAGAAATATTCTTGCTGCTGCCACCTA
     AGGTAGAAGTAATGCCTTGAGTAGTGTACGAAGGTCTTTATAAGAACGACGACGGTGGAT

+1  MetGluIlePheArgLysValGlnLysSerPheGluValProGlnAlaLysAlaGlnMet
     ------------------------------------------------------------
1141 ATGGAAATATTTCGGAAGGTACAGAAATCATTTGAAGTTCCACAGGCTAAAGCCCAGATG
     TACCTTTATAAAGCCTTCCATGTCTTTAGTAAACTTCAAGGTGTCCGATTTCGGGTCTAC

+1  ProThrIleGluArgAlaThrLeuThrArgAspPheTyrLeuPheProGlyAsn
     --------------------------------------------------------->
1201 CCCACCATAGAACGAGCAACCTTGACAAGAGATTTCTACCTCTTTCCTGGCAATTGAN
     GGGTGGTATCTTGCTCGTTGGAACTGTTCTCTAAAGATGGAGAAAGGACCGTTAACTN
```

Fig. 16A

CASPASE 6

```
  +1  MetSerSerAlaSerGlyLeuArgArgGlyHisProAlaGlyGlyGluGluAsnMetThr
      ]------------------------------------------------------------
   1  ATGAGCTCGGCCTCGGGGCTCCGCAGGGGGCACCCGGCAGGTGGGGAAGAAAACATGACA
      TACTCGAGCCGGAGCCCCGAGGCGTCCCCCGTGGGCCGTCCACCCCTTCTTTTGTACTGT
  +1  GluThrAspAlaPheTyrLysArgGluMetPheAspProAlaGluLysTyrLysMetAsp
      ------------------------------------------------------------
  61  GAAACAGATGCCTTCTATAAAGAGAAATGTTTGATCCGGCAGAAAAGTACAAAATGGAC
      CTTTGTCTACGGAAGATATTTTCTCTTTACAAACTAGGCCGTCTTTTCATGTTTTACCTG
  +1  HisArgArgArgGlyIleAlaLeuIlePheAsnHisGluArgPhePheTrpHisLeuThr
      ------------------------------------------------------------
 121  CACAGGAGGAGAGGAATTGCTTTAATCTTCAATCATGAGAGGTTCTTTTGGCACTTAACA
      GTGTCCTCCTCTCCTTAACGAAATTAGAAGTTAGTACTCTCCAAGAAAACCGTGAATTGT
  +1  LeuProGluArgArgGlyThrCysAlaAspArgAspAsnLeuThrArgArgPheSerAsp
      ------------------------------------------------------------
 181  CTGCCAGAAAGGCGGGGCACCTGCGCAGATAGAGACAATCTTACCCGCAGGTTTTCAGAT
      GACGGTCTTTCCGCCCCGTGGACGCGTCTATCTCTGTTAGAATGGGCGTCCAAAAGTCTA
  +1  LeuGlyPheGluValLysCysPheAsnAspLeuLysAlaGluGluLeuLeuLeuLysIle
      ------------------------------------------------------------
 241  CTAGGATTTGAAGTGAAATGCTTTAATGATCTTAAAGCAGAAGAACTACTGCTCAAAATT
      GATCCTAAACTTCACTTTACGAAATTACTAGAATTTCGTCTTCTTGATGACGAGTTTTAA
  +1  HisGluValSerThrValSerHisAlaAspAlaAspCysPheValCysValPheLeuSer
      ------------------------------------------------------------
 301  CATGAGGTGTCAACTGTTAGCCACGCAGATGCCGATTGCTTTGTGTGTGTCTTCCTGAGC
      GTACTCCACAGTTGACAATCGGTGCGTCTACGGCTAACGAAACACACAGAAGGACTCG
  +1  HisGlyGluGlyAsnHisIleTyrAlaTyrAspAlaLysIleGluIleGlnThrLeuThr
      ------------------------------------------------------------
 361  CATGGCGAAGGCAATCACATTTATGCATATGATGCTAAAATCGAAATTCAGACATTAACT
      GTACCGCTTCCGTTAGTGTAAATACGTATACTACGATTTTAGCTTTAAGTCTGTAATTGA
  +1  GlyLeuPheLysGlyAspLysCysHisSerLeuValGlyLysProLysIlePheIleIle
      ------------------------------------------------------------
 421  GGCTTGTTCAAAGGAGACAAGTGTCACAGCCTGGTTGGAAAACCCAAGATATTTATCATC
      CCGAACAAGTTTCCTCTGTTCACAGTGTCGGACCAACCTTTTGGGTTCTATAAATAGTAG
  +1  GlnAlaCysArgGlyAsnGlnHisAspValProValIleProLeuAspValValAspAsn
      ------------------------------------------------------------
 481  CAGGCATGTCGGGGAAACCAGCACGATGTGCCAGTCATTCCTTTGGATGTAGTAGATAAT
      GTCCGTACAGCCCCTTTGGTCGTGCTACACGGTCAGTAAGGAAACCTACATCATCTATTA
  +1  GlnThrGluLysLeuAspThrAsnIleThrGluValAspAlaAlaSerValTyrThrLeu
      ------------------------------------------------------------
 541  CAGACAGAGAAGTTGGACACCAACATAACTGAGGTGGATGCAGCCTCCGTTTACACGCTG
      GTCTGTCTCTTCAACCTGTGGTTGTATTGACTCCACCTACGTCGGAGGCAAATGTGCGAC
  +1  ProAlaGlyAlaAspPheLeuMetCysTyrSerValAlaGluGlyTyrTyrSerHisArg
      ------------------------------------------------------------
 601  CCTGCTGGAGCTGACTTCCTCATGTGTTACTCTGTTGCAGAAGGATATTATTCTCACCGG
      GGACGACCTCGACTGAAGGAGTACACAATGAGACAACGTCTTCCTATAATAAGAGTGGCC
```

Fig. 16B

CASPASE 6

```
 +1  GluThrValAsnGlySerTrpTyrIleGlnAspLeuCysGluMetLeuGlyLysTyrGly
     ----------------------------------------------------------
661  GAAACTGTGAACGGCTCATGGTACATTCAAGATTTGTGTGAGATGTTGGGAAAATATGGC
     CTTTGACACTTGCCGAGTACCATGTAAGTTCTAAACACACTCTACAACCCTTTTATACCG
 +1  SerSerLeuGluPheThrGluLeuLeuThrLeuValAsnArgLysValSerGlnArgArg
     ----------------------------------------------------------
721  TCCTCCTTAGAGTTCACAGAACTCCTCACACTGGTGAACAGGAAAGTTTCTCAGCGCCGA
     AGGAGGAATCTCAAGTGTCTTGAGGAGTGTGACCACTTGTCCTTTCAAAGAGTCGCGGCT
 +1  ValAspPheCysLysAspProSerAlaIleGlyLysLysGlnValProCysPheAlaSer
     ----------------------------------------------------------
781  GTGGACTTTTGCAAAGACCCAAGTGCAATTGGAAAGAAGCAGGTTCCCTGTTTTGCCTCA
     CACCTGAAAACGTTTCTGGGTTCACGTTAACCTTTCTTCGTCCAAGGGACAAAACGGAGT
 +1  MetLeuThrLysLysLeuHisPhePheProLysSerAsn
     -------------------------------------->
841  ATGCTAACTAAAAAGCTGCATTTCTTTCCAAAATCTAATTAAN
     TACGATTGATTTTTCGACGTAAAGAAAGGTTTTAGATTAATTN
```

Fig. 17A

CASPASE 7

```
 +1  MetAlaAspAspGlnGlyCysIleGluGluGlnGlyValGluAspSerAlaAsnGluAsp
     ]------------------------------------------------------------
  1  ATGGCAGATGATCAGGGCTGTATTGAAGAGCAGGGGGTTGAGGATTCAGCAAATGAAGAT
     TACCGTCTACTAGTCCCGACATAACTTCTCGTCCCCCAACTCCTAAGTCGTTTACTTCTA

+1  SerValAspAlaLysProAspArgSerSerPheValProSerLeuPheSerLysLysLys
     ------------------------------------------------------------
 61  TCAGTGGATGCTAAGCCAGACCGGTCCTCGTTTGTACCGTCCCTCTTCAGTAAGAAGAAG
     AGTCACCTACGATTCGGTCTGGCCAGGAGCAAACATGGCAGGGAGAAGTCATTCTTCTTC

+1  LysAsnValThrMetArgSerIleLysThrThrArgAspArgValProThrTyrGlnTyr
     ------------------------------------------------------------
121  AAAAATGTCACCATGCGATCCATCAAGACCACCCGGGACCGAGTGCCTACATATCAGTAC
     TTTTTACAGTGGTACGCTAGGTAGTTCTGGTGGGCCCTGGCTCACGGATGTATAGTCATG

+1  AsnMetAsnPheGluLysLeuGlyLysCysIleIleIleAsnAsnLysAsnPheAspLys
     ------------------------------------------------------------
181  AACATGAATTTTGAAAAGCTGGGCAAATGCATCATAATAAACAACAAGAACTTTGATAAA
     TTGTACTTAAAACTTTTCGACCCGTTTACGTAGTATTATTTGTTGTTCTTGAAACTATTT

+1  ValThrGlyMetGlyValArgAsnGlyThrAspLysAspAlaGluAlaLeuPheLysCys
     ------------------------------------------------------------
241  GTGACAGGTATGGGCGTTCGAAACGGAACAGACAAAGATGCCGAGGCGCTCTTCAAGTGC
     CACTGTCCATACCCGCAAGCTTTGCCTTGTCTGTTTCTACGGCTCCGCGAGAAGTTCACG

+1  PheArgSerLeuGlyPheAspValIleValTyrAsnAspCysSerCysAlaLysMetGln
     ------------------------------------------------------------
301  TTCCGAAGCCTGGGTTTTGACGTGATTGTCTATAATGACTGCTCTTGTGCCAAGATGCAA
     AAGGCTTCGGACCCAAAACTGCACTAACAGATATTACTGACGAGAACACGGTTCTACGTT

+1  AspLeuLeuLysLysAlaSerGluGluAspHisThrAsnAlaAlaCysPheAlaCysIle
     ------------------------------------------------------------
361  GATCTGCTTAAAAAAGCTTCTGAAGAGGACCATACAAATGCCGCCTGCTTCGCCTGCATC
     CTAGACGAATTTTTTCGAAGACTTCTCCTGGTATGTTTACGGCGGACGAAGCGGACGTAG

+1  LeuLeuSerHisGlyGluGluAsnValIleTyrGlyLysAspGlyValThrProIleLys
     ------------------------------------------------------------
421  CTCTTAAGCCATGGAGAAGAAAATGTAATTTATGGGAAAGATGGTGTCACACCAATAAAG
     GAGAATTCGGTACCTCTTCTTTTACATTAAATACCCTTTCTACCACAGTGTGGTTATTTC

+1  AspLeuThrAlaHisPheArgGlyAspArgCysLysThrLeuLeuGluLysProLysLeu
     ------------------------------------------------------------
481  GATTTGACAGCCCACTTTAGGGGGGATAGATGCAAAACCCTTTTAGAGAAACCCAAACTC
     CTAAACTGTCGGGTGAAATCCCCCCTATCTACGTTTTGGGAAAATCTCTTTGGGTTTGAG

+1  PhePheIleGlnAlaCysArgGlyThrGluLeuAspAspGlyIleGlnAlaAspSerGly
     ------------------------------------------------------------
541  TTCTTCATTCAGGCTTGCCGAGGGACCGAGCTTGATGATGGCATCCAGGCCGACTCGGGG
     AAGAAGTAAGTCCGAACGGCTCCCTGGCTCGAACTACTACCGTAGGTCCGGCTGAGCCCC

+1  ProIleAsnAspThrAspAlaAsnProArgTyrLysIleProValGluAlaAspPheLeu
     ------------------------------------------------------------
601  CCCATCAATGACACAGATGCTAATCCTCGATACAAGATCCCAGTGGAAGCTGACTTCCTC
     GGGTAGTTACTGTGTCTACGATTAGGAGCTATGTTCTAGGGTCACCTTCGACTGAAGGAG
```

Fig. 17B

CASPASE 7

```
  +1  PheAlaTyrSerThrValProGlyTyrTyrSerTrpArgSerProGlyArgGlySerTrp
      ------------------------------------------------------------
 661  TTCGCCTATTCCACGGTTCCAGGCTATTACTCGTGGAGGAGCCCAGGAAGAGGCTCCTGG
      AAGCGGATAAGGTGCCAAGGTCCGATAATGAGCACCTCCTCGGGTCCTTCTCCGAGGACC
  +1  PheValGlnAlaLeuCysSerIleLeuGluGluHisGlyLysAspLeuGluIleMetGln
      ------------------------------------------------------------
 721  TTTGTGCAAGCCCTCTGCTCCATCCTGGAGGAGCACGGAAAAGACCTGGAAATCATGCAG
      AAACACGTTCGGGAGACGAGGTAGGACCTCCTCGTGCCTTTTCTGGACCTTTAGTACGTC
  +1  IleLeuThrArgValAsnAspArgValAlaArgHisPheGluSerGlnSerAspAspPro
      ------------------------------------------------------------
 781  ATCCTCACCAGGGTGAATGACAGAGTTGCCAGGCACTTTGAGTCTCAGTCTGATGACCCA
      TAGGAGTGGTCCCACTTACTGTCTCAACGGTCCGTGAAACTCAGAGTCAGACTACTGGGT
  +1  HisPheHisGluLysLysGlnIleProCysValValSerMetLeuThrLysGluLeuTyr
      ------------------------------------------------------------
 841  CACTTCCATGAGAAGAAGCAGATCCCCTGTGTGGTCTCCATGCTCACCAAGGAACTCTAC
      GTGAAGGTACTCTTCTTCGTCTAGGGGACACACCAGAGGTACGAGTGGTTCCTTGAGATG
  +1  PheSerGln
      -------->
 901  TTCAGTCAATAGN
      AAGTCAGTTATCN
```

Fig. 18A

CASPASE 8

```
 +1  MetAspPheSerArgAsnLeuTyrAspIleGlyGluGlnLeuAspSerGluAspLeuAla
     ]-----------------------------------------------------------
  1  ATGGACTTCAGCAGAAATCTTTATGATATTGGGGAACAACTGGACAGTGAAGATCTGGCC
     TACCTGAAGTCGTCTTTAGAAATACTATAACCCCTTGTTGACCTGTCACTTCTAGACCGG

+1  SerLeuLysPheLeuSerLeuAspTyrIleProGlnArgLysGlnGluProIleLysAsp
     ------------------------------------------------------------
 61  TCCCTCAAGTTCCTGAGCCTGGACTACATTCCGCAAAGGAAGCAAGAACCCATCAAGGAT
     AGGGAGTTCAAGGACTCGGACCTGATGTAAGGCGTTTCCTTCGTTCTTGGGTAGTTCCTA

+1  AlaLeuMetLeuPheGlnArgLeuGlnGluLysArgMetLeuGluGluSerAsnLeuSer
     ------------------------------------------------------------
121  GCCTTGATGTTATTCCAGAGACTCCAGGAAAAGAGAATGTTGGAGGAAAGCAATCTGTCC
     CGGAACTACAATAAGGTCTCTGAGGTCCTTTTCTCTTACAACCTCCTTTCGTTAGACAGG

+1  PheLeuLysGluLeuLeuPheArgIleAsnArgLeuAspLeuLeuIleThrTyrLeuAsn
     ------------------------------------------------------------
181  TTCCTGAAGGAGCTGCTCTTCCGAATTAATAGACTGGATTTGCTGATTACCTACCTAAAC
     AAGGACTTCCTCGACGAGAAGGCTTAATTATCTGACCTAAACGACTAATGGATGGATTTG

+1  ThrArgLysGluGluMetGluArgGluLeuGlnThrProGlyArgAlaGlnIleSerAla
     ------------------------------------------------------------
241  ACTAGAAAGGAGGAGATGGAAAGGGAACTTCAGACACCAGGCAGGGCTCAAATTTCTGCC
     TGATCTTTCCTCCTCTACCTTTCCCTTGAAGTCTGTGGTCCGTCCCGAGTTTAAAGACGG

+1  TyrArgPheHisPheCysArgMetSerTrpAlaGluAlaAsnSerGlnCysGlnThrGln
     ------------------------------------------------------------
301  TACAGGTTCCACTTCTGCCGCATGAGCTGGGCTGAAGCAAACAGCCAGTGCCAGACACAG
     ATGTCCAAGGTGAAGACGGCGTACTCGACCCGACTTCGTTTGTCGGTCACGGTCTGTGTC

+1  SerValProPheTrpArgArgValAspHisLeuLeuIleArgValMetLeuTyrGlnIle
     ------------------------------------------------------------
361  TCTGTACCTTTCTGGCGGAGGGTCGATCATCTATTAATAAGGGTCATGCTCTATCAGATT
     AGACATGGAAAGACCGCCTCCCAGCTAGTAGATAATTATTCCCAGTACGAGATAGTCTAA

+1  SerGluGluValSerArgSerGluLeuArgSerPheLysPheLeuLeuGlnGluGluIle
     ------------------------------------------------------------
421  TCAGAAGAAGTGAGCAGATCAGAATTGAGGTCTTTTAAGTTTCTTTTGCAAGAGGAAATC
     AGTCTTCTTCACTCGTCTAGTCTTAACTCCAGAAAATTCAAAGAAAACGTTCTCCTTTAG

+1  SerLysCysLysLeuAspAspAspMetAsnLeuLeuAspIlePheIleGluMetGluLys
     ------------------------------------------------------------
481  TCCAAATGCAAACTGGATGATGACATGAACCTGCTGGATATTTTCATAGAGATGGAGAAG
     AGGTTTACGTTTGACCTACTACTGTACTTGGACGACCTATAAAAGTATCTCTACCTCTTC

+1  ArgValIleLeuGlyGluGlyLysLeuAspIleLeuLysArgValCysAlaGlnIleAsn
     ------------------------------------------------------------
541  AGGGTCATCCTGGGAGAAGGAAAGTTGGACATCCTGAAAAGAGTCTGTGCCCAAATCAAC
     TCCCAGTAGGACCCTCTTCCTTTCAACCTGTAGGACTTTTCTCAGACACGGGTTTAGTTG

+1  LysSerLeuLeuLysIleIleAsnAspTyrGluGluPheSerLysGlyGluGluLeuCys
     ------------------------------------------------------------
601  AAGAGCCTGCTGAAGATAATCAACGACTATGAAGAATTCAGCAAAGGGGAGGAGTTGTGT
     TTCTCGGACGACTTCTATTAGTTGCTGATACTTCTTAAGTCGTTTCCCCTCCTCAACACA
```

Fig. 18B

CASPASE 8

```
   +1  GlyValMetThrIleSerAspSerProArgGluGlnAspSerGluSerGlnThrLeuAsp
        ------------------------------------------------------------
  661  GGGGTAATGACAATCTCGGACTCTCCAAGAGAACAGGATAGTGAATCACAGACTTTGGAC
       CCCCATTACTGTTAGAGCCTGAGAGGTTCTCTTGTCCTATCACTTAGTGTCTGAAACCTG
   +1  LysValTyrGlnMetLysSerLysProArgGlyTyrCysLeuIleIleAsnAsnHisAsn
        ------------------------------------------------------------
  721  AAAGTTTACCAAATGAAAAGCAAACCTCGGGGATACTGTCTGATCATCAACAATCACAAT
       TTTCAAATGGTTTACTTTTCGTTTGGAGCCCCTATGACAGACTAGTAGTTGTTAGTGTTA
   +1  PheAlaLysAlaArgGluLysValProLysLeuHisSerIleArgAspArgAsnGlyThr
        ------------------------------------------------------------
  781  TTTGCAAAAGCACGGGAGAAAGTGCCCAAACTTCACAGCATTAGGGACAGGAATGGAACA
       AAACGTTTTCGTGCCCTCTTTCACGGGTTTGAAGTGTCGTAATCCCTGTCCTTACCTTGT
   +1  HisLeuAspAlaGlyAlaLeuThrThrThrPheGluGluLeuHisPheGluIleLysPro
        ------------------------------------------------------------
  841  CACTTGGATGCAGGGGCTTTGACCACGACCTTTGAAGAGCTTCATTTTGAGATCAAGCCC
       GTGAACCTACGTCCCCGAAACTGGTGCTGGAAACTTCTCGAAGTAAAACTCTAGTTCGGG
   +1  HisHisAspCysThrValGluGlnIleTyrGluIleLeuLysIleTyrGlnLeuMetAsp
        ------------------------------------------------------------
  901  CACCATGACTGCACAGTAGAGCAAATCTATGAGATTTTGAAAATCTACCAACTCATGGAC
       GTGGTACTGACGTGTCATCTCGTTTAGATACTCTAAAACTTTTAGATGGTTGAGTACCTG
   +1  HisSerAsnMetAspCysPheIleCysCysIleLeuSerHisGlyAspLysGlyIleIle
        ------------------------------------------------------------
  961  CACAGTAACATGGACTGCTTCATCTGCTGTATCCTCTCCCATGGAGACAAGGGCATCATC
       GTGTCATTGTACCTGACGAAGTAGACGACATAGGAGAGGGTACCTCTGTTCCCGTAGTAG
   +1  TyrGlyThrAspGlyGlnGluAlaProIleTyrGluLeuThrSerGlnPheThrGlyLeu
        ------------------------------------------------------------
 1021  TATGGCACTGATGGACAGGAGGCCCCCATCTATGAGCTGACATCTCAGTTCACTGGTTTG
       ATACCGTGACTACCTGTCCTCCGGGGGTAGATACTCGACTGTAGAGTCAAGTGACCAAAC
   +1  LysCysProSerLeuAlaGlyLysProLysValPhePheIleGlnAlaCysGlnGlyAsp
        ------------------------------------------------------------
 1081  AAGTGCCCTTCCCTTGCTGGAAAACCCAAAGTGTTTTTTATTCAGGCTTGTCAGGGGGAT
       TTCACGGGAAGGGAACGACCTTTTGGGTTTCACAAAAAATAAGTCCGAACAGTCCCCCTA
   +1  AsnTyrGlnLysGlyIleProValGluThrAspSerGluGluGlnProTyrLeuGluMet
        ------------------------------------------------------------
 1141  AACTACCAGAAAGGTATACCTGTTGAGACTGATTCAGAGGAGCAACCCTATTTAGAAATG
       TTGATGGTCTTTCCATATGGACAACTCTGACTAAGTCTCCTCGTTGGGATAAATCTTTAC
   +1  AspLeuSerSerProGlnThrArgTyrIleProAspGluAlaAspPheLeuLeuGlyMet
        ------------------------------------------------------------
 1201  GATTTATCATCACCTCAAACGAGATATATCCCGGATGAGGCTGACTTTCTGCTGGGGATG
       CTAAATAGTAGTGGAGTTTGCTCTATATAGGGCCTACTCCGACTGAAAGACGACCCCTAC
   +1  AlaThrValAsnAsnCysValSerTyrArgAsnProAlaGluGlyThrTrpTyrIleGln
        ------------------------------------------------------------
 1261  GCCACTGTGAATAACTGTGTTTCCTACCGAAACCCTGCAGAGGGAACCTGGTACATCCAG
       CGGTGACACTTATTGACACAAAGGATGGCTTTGGGACGTCTCCCTTGGACCATGTAGGTC
```

Fig. 18C

CASPASE 8

```
    +1  SerLeuCysGlnSerLeuArgGluArgCysProArgGlyAspAspIleLeuThrIleLeu
        ------------------------------------------------------------
  1321  TCACTTTGCCAGAGCCTGAGAGAGCGATGTCCTCGAGGCGATGATATTCTCACCATCCTG
        AGTGAAACGGTCTCGGACTCTCTCGCTACAGGAGCTCCGCTACTATAAGAGTGGTAGGAC
    +1  ThrGluValAsnTyrGluValSerAsnLysAspAspLysLysAsnMetGlyLysGlnMet
        ------------------------------------------------------------
  1381  ACTGAAGTGAACTATGAAGTAAGCAACAAGGATGACAAGAAAAACATGGGGAAACAGATG
        TGACTTCACTTGATACTTCATTCGTTGTTCCTACTGTTCTTTTTGTACCCCTTTGTCTAC
    +1  ProGlnProThrPheThrLeuArgLysLysLeuValPheProSerAsp
        -------------------------------------------->
  1441  CCTCAGCCTACTTTCACACTAAGAAAAAAACTTGTCTTCCCTTCTGATTGANN
        GGAGTCGGATGAAAGTGTGATTCTTTTTTTGAACAGAAGGGAAGACTAACTNN
```

Fig. 19A-1

CASPASE 9

```
 +1  MetAspGluAlaAspArgArgLeuLeuArgArgCysArgLeuArgLeuValGluGluLeu
      ]-----------------------------------------------------------
  1  ATGGACGAAGCGGATCGGCGGCTCCTGCGGCGGTGCCGGCTGCGGCTGGTGGAAGAGCTG
     TACCTGCTTCGCCTAGCCGCCGAGGACGCCGCCACGGCCGACGCCGACCACCTTCTCGAC

+1  GlnValAspGlnLeuTrpAspAlaLeuLeuSerSerGluLeuPheArgProHisMetIle
     -------------------------------------------------------------
 61  CAGGTGGACCAGCTCTGGGACGCCCTGCTGAGCAGCGAGCTGTTCAGGCCCCATATGATC
     GTCCACCTGGTCGAGACCCTGCGGGACGACTCGTCGCTCGACAAGTCCGGGGTATACTAG

+1  GluAspIleGlnArgAlaGlySerGlySerArgArgAspGlnAlaArgGlnLeuIleIle
     -------------------------------------------------------------
121  GAGGACATCCAGCGGGCAGGCTCTGGATCTCGGCGGGATCAGGCCAGGCAGCTGATCATA
     CTCCTGTAGGTCGCCCGTCCGAGACCTAGAGCCGCCCTAGTCCGGTCCGTCGACTAGTAT

+1  AspLeuGluThrArgGlySerGlnAlaLeuProLeuPheIleSerCysLeuGluAspThr
     -------------------------------------------------------------
181  GATCTGGAGACTCGAGGGAGTCAGGCTCTTCCTTTGTTCATCTCCTGCTTAGAGGACACA
     CTAGACCTCTGAGCTCCCTCAGTCCGAGAAGGAAACAAGTAGAGGACGAATCTCCTGTGT

+1  GlyGlnAspMetLeuAlaSerPheLeuArgThrAsnArgGlnAlaAlaLysLeuSerLys
     -------------------------------------------------------------
241  GGCCAGGACATGCTGGCTTCGTTTCTGCGAACTAACAGGCAAGCAGCAAAGTTGTCGAAG
     CCGGTCCTGTACGACCGAAGCAAAGACGCTTGATTGTCCGTTCGTCGTTTCAACAGCTTC

+1  ProThrLeuGluAsnLeuThrProValValLeuArgProGluIleArgLysProGluVal
     -------------------------------------------------------------
301  CCAACCCTAGAAAACCTTACCCCAGTGGTGCTCAGACCAGAGATTCGCAAACCAGAGGTT
     GGTTGGGATCTTTTGGAATGGGGTCACCACGAGTCTGGTCTCTAAGCGTTTGGTCTCCAA

+1  LeuArgProGluThrProArgProValAspIleGlySerGlyGlyPheGlyAspValGly
     -------------------------------------------------------------
361  CTCAGACCGGAAACACCCAGACCAGTGGACATTGGTTCTGGAGGATTTGGTGATGTCGGT
     GAGTCTGGCCTTTGTGGGTCTGGTCACCTGTAACCAAGACCTCCTAAACCACTACAGCCA

+1  AlaLeuGluSerLeuArgGlyAsnAlaAspLeuAlaTyrIleLeuSerMetGluProCys
     -------------------------------------------------------------
421  GCTCTTGAGAGTTTGAGGGGAAATGCAGATTTGGCTTACATCCTGAGCATGGAGCCCTGT
     CGAGAACTCTCAAACTCCCCTTTACGTCTAAACCGAATGTAGGACTCGTACCTCGGGACA

+1  GlyHisCysLeuIleIleAsnAsnValAsnPheCysArgGluSerGlyLeuArgThrArg
     -------------------------------------------------------------
481  GGCCACTGCCTCATTATCAACAATGTGAACTTCTGCCGTGAGTCCGGGCTCCGCACCCGC
     CCGGTGACGGAGTAATAGTTGTTACACTTGAAGACGGCACTCAGGCCCGAGGCGTGGGCG

+1  ThrGlySerAsnIleAspCysGluLysLeuArgArgArgPheSerSerProHisPheMet
     -------------------------------------------------------------
```

Fig. 19A-2

```
541  ACTGGCTCCAACATCGACTGTGAGAAGTTGCGGCGTCGCTTCTCCTCGCCGCATTTCATG
     TGACCGAGGTTGTAGCTGACACTCTTCAACGCCGCAGCGAAGAGGAGCGGCGTAAAGTAC
  +1 ValGluValLysGlyAspLeuThrAlaLysLysMetValLeuAlaLeuLeuGluLeuAla
     ------------------------------------------------------------
601  GTGGAGGTGAAGGGCGACCTGACTGCCAAGAAAATGGTGCTGGCTTTGCTGGAGCTGGCG
     CACCTCCACTTCCCGCTGGACTGACGGTTCTTTTACCACGACCGAAACGACCTCGACCGC
```

Fig. 19B

CASPASE 9

```
  +1  ArgGlnAspHisGlyAlaLeuAspCysCysValValValIleLeuSerHisGlyCysGln
      ------------------------------------------------------------
 661  CGGCAGGACCACGGTGCTCTGGACTGCTGCGTGGTGGTCATTCTCTCTCACGGCTGTCAG
      GCCGTCCTGGTGCCACGAGACCTGACGACGCACCACCAGTAAGAGAGAGTGCCGACAGTC
  +1  AlaSerHisLeuGlnPheProGlyAlaValTyrGlyThrAspGlyCysProValSerVal
      ------------------------------------------------------------
 721  GCCAGCCACCTGCAGTTCCCAGGGGCTGTCTACGGCACAGATGGATGCCCTGTGTCGGTC
      CGGTCGGTGGACGTCAAGGGTCCCCGACAGATGCCGTGTCTACCTACGGGACACAGCCAG
  +1  GluLysIleValAsnIlePheAsnGlyThrSerCysProSerLeuGlyGlyLysProLys
      ------------------------------------------------------------
 781  GAGAAGATTGTGAACATCTTCAATGGGACCAGCTGCCCCAGCCTGGGAGGAAAGCCCAAG
      CTCTTCTAACACTTGTAGAAGTTACCCTGGTCGACGGGGTCGGACCCTCCTTTCGGGTTC
  +1  LeuPhePheIleGlnAlaCysGlyGlyGluGlnLysAspHisGlyPheGluValAlaSer
      ------------------------------------------------------------
 841  CTCTTTTTCATCCAGGCCTGTGGTGGGGAGCAGAAAGACCATGGGTTTGAGGTGGCCTCC
      GAGAAAAAGTAGGTCCGGACACCACCCCTCGTCTTTCTGGTACCCAAACTCCACCGGAGG
  +1  ThrSerProGluAspGluSerProGlySerAsnProGluProAspAlaThrProPheGln
      ------------------------------------------------------------
 901  ACTTCCCCTGAAGACGAGTCCCCTGGCAGTAACCCCGAGCCAGATGCCACCCCGTTCCAG
      TGAAGGGGACTTCTGCTCAGGGGACCGTCATTGGGGCTCGGTCTACGGTGGGGCAAGGTC
  +1  GluGlyLeuArgThrPheAspGlnLeuAspAlaIleSerSerLeuProThrProSerAsp
      ------------------------------------------------------------
 961  GAAGGTTTGAGGACCTTCGACCAGCTGGACGCCATATCTAGTTTGCCCACACCCAGTGAC
      CTTCCAAACTCCTGGAAGCTGGTCGACCTGCGGTATAGATCAAACGGGTGTGGGTCACTG
  +1  IlePheValSerTyrSerThrPheProGlyPheValSerTrpArgAspProLysSerGly
      ------------------------------------------------------------
1021  ATCTTTGTGTCCTACTCTACTTTCCCAGGTTTTGTTTCCTGGAGGGACCCCAAGAGTGGC
      TAGAAACACAGGATGAGATGAAAGGGTCCAAAACAAAGGACCTCCCTGGGGTTCTCACCG
  +1  SerTrpTyrValGluThrLeuAspAspIlePheGluGlnTrpAlaHisSerGluAspLeu
      ------------------------------------------------------------
1081  TCCTGGTACGTTGAGACCCTGGACGACATCTTTGAGCAGTGGGCTCACTCTGAAGACCTG
      AGGACCATGCAACTCTGGGACCTGCTGTAGAAACTCGTCACCCGAGTGAGACTTCTGGAC
  +1  GlnSerLeuLeuLeuArgValAlaAsnAlaValSerValLysGlyIleTyrLysGlnMet
      ------------------------------------------------------------
1141  CAGTCCCTCCTGCTTAGGGTCGCTAATGCTGTTTCGGTGAAAGGGATTTATAAACAGATG
      GTCAGGGAGGACGAATCCCAGCGATTACGACAAAGCCACTTTCCCTAAATATTTGTCTAC
  +1  ProGlyCysPheAsnPheLeuArgLysLysLeuPhePheLysThrSer
      ----------------------------------------------->
1201  CCTGGTTGCTTTAATTTCCTCCGGAAAAAACTTTTCTTTAAAACATCATAAN
      GGACCAACGAAATTAAAGGAGGCCTTTTTTGAAAAGAAATTTTGTAGTATTN
```

Fig. 20A

CASPASE 10

```
  +1  MetLysSerGlnGlyGlnHisTrpTyrSerSerSerAspLysAsnCysLysValSerPhe
   1  ATGAAATCTCAAGGTCAACATTGGTATTCCAGTTCAGATAAAAACTGTAAAGTGAGCTTT
      TACTTTAGAGTTCCAGTTGTAACCATAAGGTCAAGTCTATTTTTGACATTTCACTCGAAA
  +1  ArgGluLysLeuLeuIleIleAspSerAsnLeuGlyValGlnAspValGluAsnLeuLys
  61  CGTGAGAAGCTTCTGATTATTGATTCAAACCTGGGGGTCCAAGATGTGGAGAACCTCAAG
      GCACTCTTCGAAGACTAATAACTAAGTTTGGACCCCCAGGTTCTACACCTCTTGGAGTTC
  +1  PheLeuCysIleGlyLeuValProAsnLysLysLeuGluLysSerSerSerAlaSerAsp
 121  TTTCTCTGCATAGGATTGGTCCCCAACAAGAAGCTGGAGAAGTCCAGCTCAGCCTCAGAT
      AAAGAGACGTATCCTAACCAGGGGTTGTTCTTCGACCTCTTCAGGTCGAGTCGGAGTCTA
  +1  ValPheGluHisLeuLeuAlaGluAspLeuLeuSerGluGluAspProPhePheLeuAla
 181  GTTTTTGAACATCTCTTGGCAGAGGATCTGCTGAGTGAGGAAGACCCTTTCTTCCTGGCA
      CAAAAACTTGTAGAGAACCGTCTCCTAGACGACTCACTCCTTCTGGGAAAGAAGGACCGT
  +1  GluLeuLeuTyrIleIleArgGlnLysLysLeuLeuGlnHisLeuAsnCysThrLysGlu
 241  GAACTCCTCTATATCATACGGCAGAAGAAGCTGCTGCAGCACCTCAACTGTACCAAAGAG
      CTTGAGGAGATATAGTATGCCGTCTTCTTCGACGACGTCGTGGAGTTGACATGGTTTCTC
  +1  GluValGluArgLeuLeuProThrArgGlnArgValSerLeuPheArgAsnLeuLeuTyr
 301  GAAGTGGAGCGACTGCTGCCCACCCGACAAAGGGTTTCTCTGTTTAGAAACCTGCTCTAC
      CTTCACCTCGCTGACGACGGGTGGGCTGTTTCCCAAAGAGACAAATCTTTGGACGAGATG
  +1  GluLeuSerGluGlyIleAspSerGluAsnLeuLysAspMetIlePheLeuLeuLysAsp
 361  GAACTGTCAGAAGGCATTGACTCAGAGAACTTAAAGGACATGATCTTCCTTCTGAAAGAC
      CTTGACAGTCTTCCGTAACTGAGTCTCTTGAATTTCCTGTACTAGAAGGAAGACTTTCTG
  +1  SerLeuProLysThrGluMetThrSerLeuSerPheLeuAlaPheLeuGluLysGlnGly
 421  TCGCTTCCCAAAACTGAAATGACCTCCCTAAGTTTCCTGGCATTTCTAGAGAAACAAGGT
      AGCGAAGGGTTTTGACTTTACTGGAGGGATTCAAAGGACCGTAAAGATCTCTTTGTTCCA
  +1  LysIleAspGluAspAsnLeuThrCysLeuGluAspLeuCysLysThrValValProLys
 481  AAAATAGATGAAGATAATCTGACATGCCTGGAGGACCTCTGCAAAACAGTTGTACCTAAA
      TTTTATCTACTTCTATTAGACTGTACGGACCTCCTGGAGACGTTTTGTCAACATGGATTT
  +1  LeuLeuArgAsnIleGluLysTyrLysArgGluLysAlaIleGlnIleValThrProPro
 541  CTTTTGAGAAACATAGAGAAATACAAAAGAGAGAAAGCTATCCAGATAGTGACACCTCCT
      GAAAACTCTTTGTATCTCTTTATGTTTTCTCTCTTTCGATAGGTCTATCACTGTGGAGGA
  +1  ValAspLysGluAlaGluSerTyrGlnGlyGluGluGluLeuValSerGlnThrAspVal
 601  GTAGACAAGGAAGCCGAGTCGTATCAAGGAGAGGAAGAACTAGTTTCCCAAACAGATGTT
      CATCTGTTCCTTCGGCTCAGCATAGTTCCTCTCCTTCTTGATCAAAGGGTTTGTCTACAA
```

Fig. 20B-1

CASPASE 10

```
  +1  LysThrPheLeuGluAlaLeuProArgAlaAlaValTyrArgMetAsnArgAsnHisArg
      ------------------------------------------------------------
 661  AAGACATTCTTGGAAGCCTTACCGAGGGCAGCTGTGTACAGGATGAATCGGAACCACAGA
      TTCTGTAAGAACCTTCGGAATGGCTCCCGTCGACACATGTCCTACTTAGCCTTGGTGTCT
  +1  GlyLeuCysValIleValAsnAsnHisSerPheThrSerLeuLysAspArgGlnGlyThr
      ------------------------------------------------------------
 721  GGCCTCTGTGTCATTGTCAACAACCACAGCTTTACCTCCCTGAAGGACAGACAAGGAACC
      CCGGAGACACAGTAACAGTTGTTGGTGTCGAAATGGAGGGACTTCCTGTCTGTTCCTTGG
  +1  HisLysAspAlaGluIleLeuSerHisValPheGlnTrpLeuGlyPheThrValHisIle
      ------------------------------------------------------------
 781  CATAAAGATGCTGAGATCCTGAGTCATGTGTTCCAGTGGCTTGGGTTCACAGTGCATATA
      GTATTTCTACGACTCTAGGACTCAGTACACAAGGTCACCGAACCCAAGTGTCACGTATAT
  +1  HisAsnAsnValThrLysValGluMetGluMetValLeuGlnLysGlnLysCysAsnPro
      ------------------------------------------------------------
 841  CACAATAATGTGACGAAAGTGGAAATGGAGATGGTCCTGCAGAAGCAGAAGTGCAATCCA
      GTGTTATTACACTGCTTTCACCTTTACCTCTACCAGGACGTCTTCGTCTTCACGTTAGGT
  +1  AlaHisAlaAspGlyAspCysPheValPheCysIleLeuThrHisGlyArgPheGlyAla
      ------------------------------------------------------------
 901  GCCCATGCCGACGGGGACTGCTTCGTGTTCTGTATTCTGACCCATGGGAGATTTGGAGCT
      CGGGTACGGCTGCCCCTGACGAAGCACAAGACATAAGACTGGGTACCCTCTAAACCTCGA
  +1  ValTyrSerSerAspGluAlaLeuIleProIleArgGluIleMetSerHisPheThrAla
      ------------------------------------------------------------
 961  GTCTACTCTTCGGATGAGGCCCTCATTCCCATTCGGGAGATCATGTCTCACTTCACAGCC
      CAGATGAGAAGCCTACTCCGGGAGTAAGGGTAAGCCCTCTAGTACAGAGTGAAGTGTCGG
  +1  LeuGlnCysProArgLeuAlaGluLysProLysLeuPhePheIleGlnAlaCysGlnGly
      ------------------------------------------------------------
1021  CTGCAGTGCCCTAGACTGGCTGAAAAACCTAAACTCTTTTTCATCCAGGCCTGCCAAGGT
      GACGTCACGGGATCTGACCGACTTTTTGGATTTGAGAAAAAGTAGGTCCGGACGGTTCCA
  +1  GluGluIleGlnProSerValSerIleGluAlaAspAlaLeuAsnProGluGlnAlaPro
      ------------------------------------------------------------
1081  GAAGAGATACAGCCTTCCGTATCCATCGAAGCAGATGCTCTGAACCCTGAGCAGGCACCC
      CTTCTCTATGTCGGAAGGCATAGGTAGCTTCGTCTACGAGACTTGGGACTCGTCCGTGGG
  +1  ThrSerLeuGlnAspSerIleProAlaGluAlaAspPheLeuLeuGlyLeuAlaThrVal
      ------------------------------------------------------------
1141  ACTTCCCTGCAGGACAGTATTCCTGCCGAGGCTGACTTCCTACTTGGTCTGGCCACTGTC
      TGAAGGGACGTCCTGTCATAAGGACGGCTCCGACTGAAGGATGAACCAGACCGGTGACAG
  +1  ProGlyTyrValSerPheArgHisValGluGluGlySerTrpTyrIleGlnSerLeuCys
      ------------------------------------------------------------
1201  CCAGGCTATGTATCCTTTCGGCATGTGGAGGAAGGCAGCTGGTATATTCAGTCTCTGTGT
      GGTCCGATACATAGGAAAGCCGTACACCTCCTTCCGTCGACCATATAAGTCAGAGACACA
  +1  AsnHisLeuLysLysLeuValProArgHisGluAspIleLeuSerIleLeuThrAlaVal
      ------------------------------------------------------------
1261  AATCATCTGAAGAAATTGGTCCCAAGACATGAAGACATCTTATCCATCCTCACTGCTGTC
      TTAGTAGACTTCTTTAACCAGGGTTCTGTACTTCTGTAGAATAGGTAGGAGTGACGACAG
```

Fig. 20B-2

CASPASE 10

```
  +1 AsnAspAspValSerArgArgValAspLysGlnGlyThrLysLysGlnMetProGlnPro
     ---------------------------------------------------------------
1321 AACGATGATGTGAGTCGAAGAGTGGACAAACAGGGAACAAAGAAACAGATGCCCCAGCCT
     TTGCTACTACACTCAGCTTCTCACCTGTTTGTCCCTTGTTTCTTTGTCTACGGGGTCGGA
  +1 AlaPheThrLeuArgLysLysLeuValPheProValProLeuAspAlaLeuSerIle
     ---------------------------------------------------------->
1381 GCTTTCACACTAAGGAAAAAACTAGTATTCCCTGTGCCCCTGGATGCACTTTCAATATAG
     CGAAAGTGTGATTCCTTTTTTGATCATAAGGGACACGGGGACCTACGTGAAAGTTATATC
```

Fig. 21A

Rev-caspase-3

```
Met Ile Glu Thr Asp Ser Gly Val Asp Asp Met Ala Cys His Lys Ile
Pro Val Glu Ala Asp Phe Leu Tyr Ala Tyr Ser Thr Ala Pro Gly Tyr Tyr
Ser Trp Arg Asn Ser Lys Asp Gly Ser Trp Phe Ile Gln Ser Leu Cys Ala
Met Leu Lys Gln Tyr Ala Asp Lys Leu Glu Phe Met His Ile Leu Thr Arg
Val Asn Arg Lys Val Ala Thr Glu Phe Glu Ser Phe Ser Phe Asp Ala Thr
Phe His Ala Lys Lys Gln Ile Pro Cys Ile Val Ser Met Leu Thr Lys Glu
Leu Tyr Phe Tyr His Asp Glu Val Asp Gly Gly Ser Pro Met Glu Asn Thr
Glu Asn Ser Val Asp Ser Lys Ser Ile Lys Asn Leu Glu Pro Lys Ile Ile
His Gly Ser Glu Ser Met Asp Ser Gly Ile Ser Leu Asp Asn Ser Tyr Lys
Met Asp Tyr Pro Glu Met Gly Leu Cys Ile Ile Asn Asn Lys Asn Phe
His Lys Ser Thr Gly Met Thr Ser Arg Ser Gly Thr Asp Val Asp Ala Ala
Asn Leu Arg Glu Thr Phe Arg Asn Leu Lys Tyr Glu Val Arg Asn Lys Asn
Asp Leu Thr Arg Glu Glu Ile Val Glu Leu Met Arg Asp Val Ser Lys Glu
Asp His Ser Lys Arg Ser Ser Phe Val Cys Val Leu Leu Ser His Gly Glu
Glu Gly Ile Ile Phe Gly Thr Asn Gly Pro Val Asp Leu Lys Lys Ile Thr
Asn Phe Phe Arg Gly Asp Arg Cys Arg Ser Leu Thr Gly Lys Pro Lys Leu
Phe Ile Ile Gln Ala Cys Arg Gly Thr Glu Leu Asp Cys Gly Ile Glu Thr
Asp
```

Fig. 21B

Uncleavable Rev-caspase-3

```
Met Ile Glu Thr Asp Ser Gly Val Asp Asp Met Ala Cys His Lys Ile
Pro Val Glu Ala Asp Phe Leu Tyr Ala Tyr Ser Thr Ala Pro Gly Tyr Tyr
Ser Trp Arg Asn Ser Lys Asp Gly Ser Trp Phe Ile Gln Ser Leu Cys Ala
Met Leu Lys Gln Tyr Ala Asp Lys Leu Glu Phe Met His Ile Leu Thr Arg
Val Asn Arg Lys Val Ala Thr Glu Phe Glu Ser Phe Ser Phe Asp Ala Thr
Phe His Ala Lys Lys Gln Ile Pro Cys Ile Val Ser Met Leu Thr Lys Glu
Leu Tyr Phe Tyr His Gly Ser Pro Met Glu Asn Thr Glu Asn Ser Val Ala
Ser Lys Ser Ile Lys Asn Leu Glu Pro Lys Ile Ile His Gly Ser Glu Ser
Met Ala Ser Gly Ile Ser Leu Asp Asn Ser Tyr Lys Met Asp Tyr Pro Glu
Met Gly Leu Cys Ile Ile Ile Asn Asn Lys Asn Phe His Lys Ser Thr Gly
Met Thr Ser Arg Ser Gly Thr Asp Val Asp Ala Ala Asn Leu Arg Glu Thr
Phe Arg Asn Leu Lys Tyr Glu Val Arg Asn Lys Asn Asp Leu Thr Arg Glu
Glu Ile Val Glu Leu Met Arg Asp Val Ser Lys Glu Asp His Ser Lys Arg
Ser Ser Phe Val Cys Val Leu Leu Ser His Gly Glu Glu Gly Ile Ile Phe
Gly Thr Asn Gly Pro Val Asp Leu Lys Lys Ile Thr Asn Phe Phe Arg Gly
Asp Arg Cys Arg Ser Leu Thr Gly Lys Pro Lys Leu Phe Ile Ile Gln Ala
Cys Arg Gly Thr Glu Leu Asp Cys Gly Ile Glu Thr Asp
```

Fig. 21C

> Rev-caspase-6

```
Met Val Glu Ile Asp Ala Ala Ser Val Tyr Thr Leu Pro Ala Gly Ala Asp
Phe Leu Met Cys Tyr Ser Val Ala Glu Gly Tyr Tyr Ser His Arg Glu Thr
Val Asn Gly Ser Trp Tyr Ile Gln Asp Leu Cys Glu Met Leu Gly Lys Tyr
Gly Ser Ser Leu Glu Phe Thr Glu Leu Leu Thr Leu Val Asn Arg Lys Val
Ser Gln Arg Arg Val Asp Phe Cys Lys Asp Pro Ser Ala Ile Gly Lys Lys
Gln Val Pro Cys Phe Ala Ser Met Leu Thr Lys Lys Leu His Phe Phe Pro
Lys Ser Asn Leu Glu His His His His His His Val Glu Ile Asp Gly Gly
Ser Pro Met Ser Ser Ala Ser Gly Leu Arg Arg Gly His Pro Ala Gly Gly
Glu Glu Asn Met Thr Glu Thr Asp Ala Phe Tyr Lys Arg Glu Met Phe Asp
Pro Ala Glu Lys Tyr Lys Met Asp His Arg Arg Arg Gly Ile Ala Leu Ile
Phe Asn His Glu Arg Phe Phe Trp His Leu Thr Leu Pro Glu Arg Arg Gly
Thr Cys Ala Asp Arg Asp Asn Leu Thr Arg Arg Phe Ser Asp Leu Gly Phe
Glu Val Lys Cys Phe Asn Asp Leu Lys Ala Glu Glu Leu Leu Leu Lys Ile
His Glu Val Ser Thr Val Ser His Ala Asp Ala Asp Cys Phe Val Cys Val
Phe Leu Ser His Gly Glu Gly Asn His Ile Tyr Ala Tyr Asp Ala Lys Ile
Glu Ile Gln Thr Leu Thr Gly Leu Phe Lys Gly Asp Lys Cys His Ser Leu
Val Gly Lys Pro Lys Ile Phe Ile Ile Gln Ala Cys Arg Gly Asn Gln His
Asp Val Pro Val Ile Pro Leu Asp Val Val Asp
```

RECOMBINANT, ACTIVE CASPASES AND USES THEREOF

CROSS REFERENCE TO RELATED APPLICATION

The present application is a divisional of U.S. application Ser. No. 09/227,721, filed Jan. 8, 1999; now U.S. Pat. No. 6,379,950 which application claims the benefit of priority from U.S. Provisional Application Serial No. 60/070,987, filed Jan. 9, 1998, now abandoned; all prior applications are hereby incorporated herein by reference.

TECHNICAL FIELD

The present invention relates generally to regulating apoptosis, and more particularly to the novel aspartate-specific cysteine proteases known as caspases, their coding regions, mutant forms thereof, and their use in screening assays and as pharmaceutical compositions for the controlled death of targeted cells to treat human disease.

BACKGROUND OF THE INVENTION

Tissue homeostasis is maintained by the process of apoptosis—that is, the normal physiological process of programmed cell death. Changes to the apoptotic pathway that prevent or delay normal cell turnover can be just as important in the pathogenesis of diseases as are abnormalities in the regulation of the cell cycle. Like cell division, which is controlled through complex interactions between cell cycle regulatory proteins, apoptosis is similarly regulated under normal circumstances by the interaction of gene products that either prevent or induce cell death.

Since apoptosis functions in maintaining tissue homeostasis in a range of physiological processes such as embryonic development, immune cell regulation and normal cellular turnover, the dysfunction or loss of regulated apoptosis can lead to a variety of pathological disease states. For example, the loss of apoptosis can lead to the pathological accumulation of self-reactive lymphocytes that occurs with many autoimmune diseases. Inappropriate loss or inhibition of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can alter the natural progression of many of these diseases.

Although apoptosis is mediated by diverse signals and complex interactions of cellular gene products, the results of these interactions ultimately feed into a cell death pathway that is evolutionarily conserved between humans and invertebrates. The pathway, itself, is a cascade of proteolytic events analogous to that of the blood coagulation cascade.

Several gene families and products that modulate the apoptotic process have now been identified. One family is the aspartate-specific cysteine proteases ("caspases"). The caspase Ced-3, identified in *C. elegans*, is required for programmed cell death during development of the roundworm *C. elegans*. Ced-3 homologues as well as other caspases have been characterized. The human caspase family includes, for example, human ICE (interleukin-1-β converting enzyme) (caspase-1), $ICE_{rel}II$ (caspase-4), $ICE_{rel}III$ (caspase-5), Mch5 (caspase-8), Mch4 (caspase-10), ICE-LAP6 (caspase-9), Mch2 (caspase-6), CPP32 (caspase-3), ICE-LAP3 (casepase-7), ICH-1 (caspase-2), Caspase 11–14, and others.

The caspases share many features. In this regard, caspases are cysteine proteases (named for a cysteine residue in the active site) that cleave substrates at Asp-X bonds. Furthermore, the primary caspase product is a zymogen that requires proteolytic cleavage at specific internal aspartate residues for activation. The primary gene product is arranged such that the N-terminal peptide (prodomain) precedes a large subunit domain, which precedes a small subunit domain. Cleavage of a caspase yields two subunits, a large (generally approximately 20 kD) and a small (generally approximately 10 kD) subunit that associate non-covalently: to form a heterodimer, and, in some caspases, an N-terminal peptide of varying length (see FIG. 1). The heterodimer may combine non-covalently to form a tetramer.

Caspase zymogens are themselves substrates for caspases. Inspection of the interdomain linkages in each zymogen reveals target sites (i.e. protease sites) that indicate a hierarchical relationship of caspase activation. By analyzing such pathways, it has been demonstrated that caspases are required for apoptosis to occur. Moreover, caspases appear to be necessary for the accurate and limited proteolytic events which are the hallmark of classic apoptosis (see Salvesen and Dixit, *Cell*, 91: 443–446, 1997). However, when overexpressed in mammalian cells, the short prodomain caspases-3 and -6 cells are unable to undergo autocatalytic processing/activation and do not induce apoptosis. Thus, no cellular model system has been developed in which to test inhibitors of these caspases nor is gene delivery of a caspase commonplace.

Therefore, there exists a need in the art for methods of assaying compounds for their ability to affect caspase activity as well as for methods of regulating caspases in order to treat diseases and syndromes. The present invention provides recombinant caspase constructs that are active in cells, allowing the regulation of apoptosis for the treatment of pathology as well as providing methods and compositions for assaying compounds for caspase inhibitory and, thus, anti-apoptotic effects, while further providing other related advantages.

SUMMARY OF THE INVENTION

The present invention generally provides rev-caspases. In one aspect, the invention provides an isolated nucleic acid molecule encoding a rev-caspase. In certain embodiments, the rev-caspase is selected from the group consisting of rev-caspase-1, rev-caspase-2, rev-caspase-3, rev-caspase-4, rev-caspase-5, rev-caspase-6, rev-caspase-7, rev-caspase-8, rev-caspase-9, rev-caspase-10, rev-caspase-11, rev-caspase-12, rev-caspase-13, and rev-caspase-14. In other preferred embodiments, the rev-caspase is a human rev-caspase. Nucleic acid and amino acid sequences of rev-caspases are provided. The invention also provides rev-caspase proteins.

In another aspect, an expression vector comprising the nucleic acid molecule encoding rev-caspase is provided, wherein the sequence encoding rev-caspase is operatively linked to a promoter. In certain embodiments, the promoter is inducible, such as HIV LTR. Host cells transfected with the expression vectors are also provided.

In the present invention, methods of identifying an inhibitor or enhancer of caspase processing activity are provided, comprising: (a) contacting a sample containing an in vitro translated rev-caspase with a candidate inhibitor or candidate enhancer; and (b) detecting the presence of large and small subunits of rev-caspase, and therefrom determining the level of caspase processing activity, wherein a decrease in processing indicates the presence of a caspase inhibitor, and wherein an increase in processing indicates the presence of a caspase enhancer, wherein processed rev-caspase yields large and small subunits.

In other aspects, methods are provided for identifying an inhibitor or enhancer of caspase processing activity, comprising: (a) contacting a cell transfected with the vector expressing rev-caspase with a candidate inhibitor or candidate enhancer; and (b) detecting the presence of large and small subunits of rev-caspase, and therefrom determining the level of caspase processing activity, wherein a decrease in processing indicates the presence of a caspase inhibitor, and wherein an increase in processing indicates the presence of a caspase enhancer, wherein processed rev-caspase yields large and small subunits.

Methods are also provided for identifying an inhibitor or enhancer of caspase-mediated apoptosis, comprising: (a) contacting a cell transfected with the vector expressing rev-caspase with a candidate inhibitor or candidate enhancer or with a reference compound; and (b) detecting cell viability, wherein viability of cells contacted with a candidate is increased in the presence of an inhibitor and is decreased in the presence of an enhancer compared to cells contacted with a reference compound.

In other aspects, gene delivery vehicles, comprising the nucleic acid molecule encoding a rev-caspase are provided, wherein the rev-caspase sequence is operatively linked to a promoter. In preferred embodiments, the gene delivery vehicle is a retrovirus or adenovirus or the nucleic acid molecule is associated with a polycation. The gene delivery vehicle may further comprise a ligand that binds a cell surface receptor.

The invention also provides methods of treating cancer or autoimmune diseases, comprising administering to a patient the gene delivery vehicles disclosed herein.

These and other aspects of the present invention will become evident upon reference to the following detailed description and attached drawings. In addition, the various references set forth below that describe in more detail certain procedures or compositions (e.g., plasmids, etc.), and are therefore incorporated by reference in their entirety.

BRIEF DESCRIPTION OF THE DRAWINGS

FIG. 1A is a schematic representation of the processing and folding of human caspase-3 into the mature zymogen represented by bar and ribbon diagrams and is representative of other caspases. α helices are shown as spirals and the β strands are represented by arrows. The N- and the C-termini of the LS are labeled N-LS and C-LS, respectively, and the termini of the SS are similarly labeled N-SS and C-SS.

FIGS. 1B and C are schematic representations of rev-caspase-3 and -6, respectively. In both FIG. 1B and C the N-terminus of the SS and the C-terminus of the LS are labeled as in FIG. 1A and the linker region between the C-SS and the N-LS which includes the caspase-3 or -6 prodomain is represented by a thin line. Solid arrows indicate the cleavage sites (DEVDG (SEQ ID NO:38), Asp9 and Asp28—for rev-caspase-3 and VEIDA (SEQ ID NO:116), and Asp23—for rev-caspase-6) within the linker region. The hatched boxes represent a 15 residue-long T7-tag on the N-termini of the wild-type and the rev-caspases. All aspartate processing sites are indicated on the bar diagrams. FIG. 1B further depicts a schematic representation of the spontaneous folding of rev-caspase-3 into the mature zymogen represented a ribbon diagram. The ribbon diagram of rev-caspase-3 is based on the published crystal structure of caspase-3.

FIGS. 2B and C are scanned images of autoradiograms representing SDS-PAGE analysis of the autoprocessing of rev-caspase-3 and -6, respectively in the presence of varying levels of selected caspase inhibitors. Rev-caspase-3 (FIG. 2B) or rev-caspase-6 (FIG. 2C) were in vitro translated in the presence of increasing concentrations of DEVD-CHO (0.04 μM); (SEQ ID NO:52), or zVAD-fmk (0–5 μM). The translation products were then analyzed as in FIG. 2A. WT, wild-type.

In FIG. 3A purified human PARP was incubated with buffer (lane 1) or BL-21 bacterial extracts prepared from bacteria transformed with caspase-3 (lane 2), rev-caspase-3 (lane 3), caspase-6 (lane 4), rev-caspase-6 (lane 5) constructs or empty pET28a vector (lane 6) for 2 h at 37° C. The reaction products were then analyzed by SDS-PAGE and Western blotting with anti-human PARP antibody.

FIG. 5A is a scanned image of an autoradiogram representing SDS-PAGE analysis of the enzymatic activity of uncleavable rev-caspase-3. Uncleavable rev-caspase-3 was in vitro translated in the absence or the presence of increasing concentrations of DEVD-CHO (SEQ ID NO:52),. The translation product contains a cleavable 35 residues-long His6-T7-tag at its N-terminus. The active site mutant rev-caspase-3 (Rev C/A) was used as a control. The p32 cleavage product without the His6-T7-tag is indicated to the right.

FIG. 5B is a plot of an activity assay of bacterially expressed uncleavable rev-caspase-3. The plot measures the ability of the uncleavable rev-caspase-3 to cleave the DEVD-AMC (SEQ ID NO:52), substrate. Rev, rev-caspase-3; Rev-mod, uncleavable rev-caspase-3; Rev-C/A, rev-caspase-3 with an active site mutation.

FIG. 6 is a multiple amino acid sequence alignment of the relatively conserved regions of the caspases (SEQ ID NOs:54–115). In the bottom line, "c" refers to residues involved in catalysis, "b" refers to residues that bind the substrate-carboxylate of P1 Asp, "a" refers to residues adjacent to the substrate P2-P4 recognition responsible amino acids, "DX" indicates known and potential processing sites between the small and large subunits of the caspases. The roman numerals at the left of the figure indicate the caspase subfamilies: Ced-like (I), ICE-like (II), and the Nedd2/Ich-1-like (III). The asterisk represents the non-conservative substitution in the active site pentapeptide sequences of Mch4 (caspase-10), Mch5 (caspase-8), and Mch6 (caspase-9)

FIG. 7 depicts a nucleotide sequence of Rev-caspase-3 (SEQ ID NO:1).

FIG. 8 depicts a nucleotide sequence of uncleavable Rev-caspase-3 (SEQ ID NO:2).

FIG. 9 depicts a nucleotide sequence of Rev-caspase-6 (SEQ ID NO:3).

FIG. 10 depicts a schematic of some possible rev-caspases. 1, intervening sequence; SS, small subunit; P, prodomain; LS, large subunit; X, linker.

FIGS. 11A and 11B depict a nucleotide (SEQ ID NOs:4 and 5) and predicted amino acid sequence of caspase-1 (SEQ ID NO:6).

FIGS. 12A and 12B depict a nucleotide (SEQ ID NOs:7 and 8) and predicted amino acid sequence of caspase-2 (SEQ ID NO:9).

FIGS. 13A and 13B depict a nucleotide (SEQ ID NOs:10 and 11) and predicted amino acid sequence of caspase-3 (SEQ ID NO:12).

FIGS. 14A and 14B depict a nucleotide (SEQ ID NOs:13 and 14) and predicted amino acid sequence of caspase-4 (SEQ ID NO:15).

FIGS. 15A and 15B depict a nucleotide (SEQ ID NOs:16 and 17) and predicted amino acid sequence of caspase-5 (SEQ ID NO:18).

FIGS. 16A and 16B depict a nucleotide (SEQ ID NOs:19 and 20) and predicted amino acid sequence of caspase-6 (SEQ ID NO:21).

FIGS. 17A and 17B depict a nucleotide (SEQ ID NOs:22 and 23) and predicted amino acid sequence of caspase-7 (SEQ ID NO:24).

FIGS. 18A-18C depict a nucleotide (SEQ ID NOs:25 and 26) and predicted amino acid sequence of caspase-8 (SEQ ID NO:27).

FIGS. 19A and 19B depict a nucleotide (SEQ ID NOs:28 and 29) and predicted amino acid sequence of caspase-9 (SEQ ID NO:30).

FIGS. 20A and 20B depict a nucleotide (SEQ ID NOs:31 and 32) and predicted amino acid sequence of caspase-10 (SEQ ID NO:33).

FIGS. 21A, 21B, and 21C depict predicted amino acid sequences of Rev-caspase-3 (A; SEQ ID NO:34), uncleavable rev-caspase-3 (B; SEQ ID NO:35), and rev-caspase-6 (C; SEQ ID NO:36).

DETAILED DESCRIPTION OF THE INVENTION

Figure 2A:
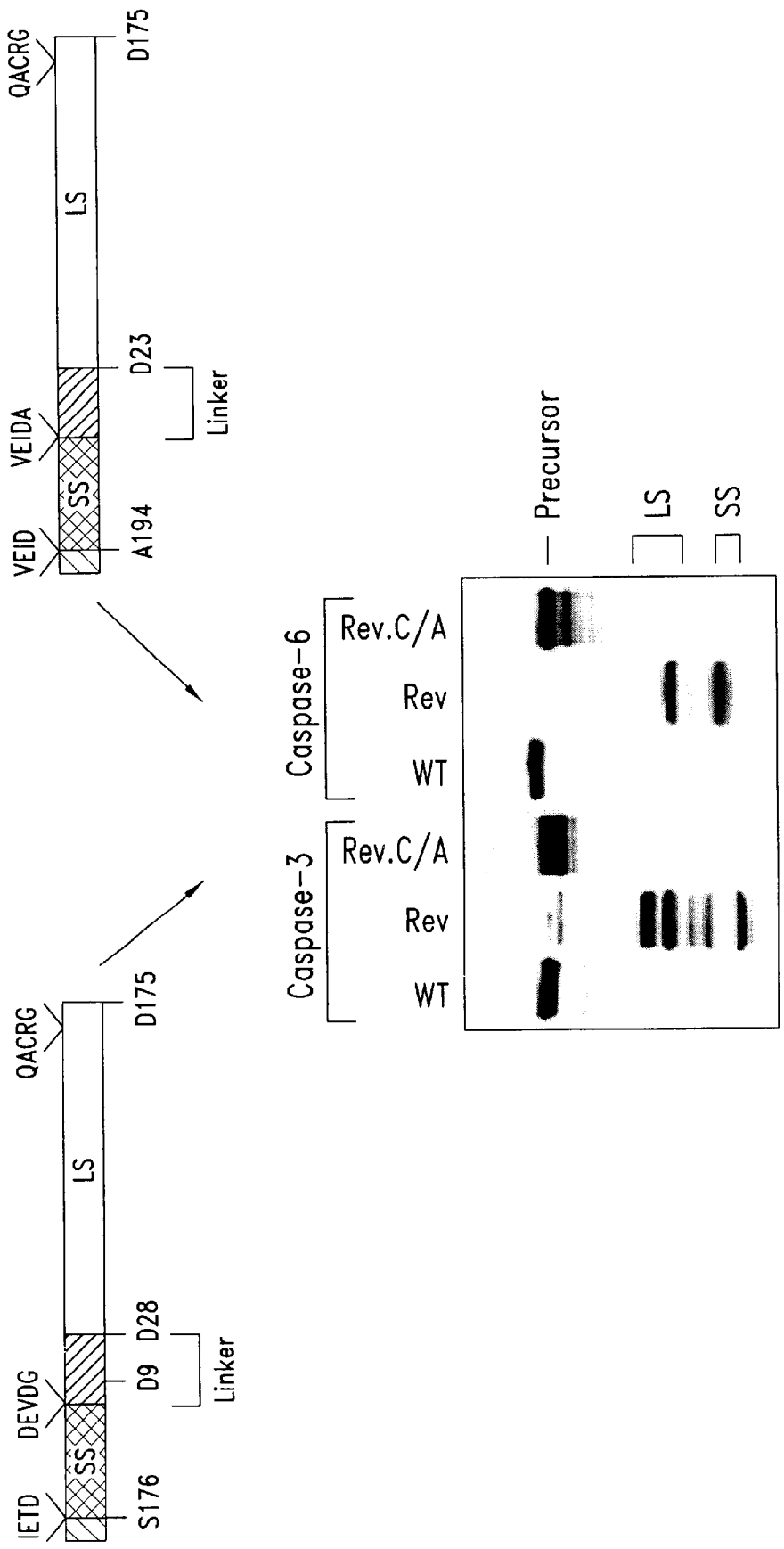
FIG. 2A is a scanned image of an autoradiogram representing SDS-PAGE analysis of rev-caspase autoprocessing. Caspase-3 and -6 or their rev-versions (Rev) including active site Cys to Ala mutants (Rev C/A) in pRSC-lacZ constructs were in vitro translated in the presence of $^{35}$S-methionine. The translation products were then analyzed by SDS-PAGE and autoradiography. The LS and the SS are indicated.

Prior to setting forth the invention, it may be helpful to an understanding thereof to set forth definitions of certain terms that will be used hereinafter.

As used herein, a caspase refers to a cysteine protease that specifically cleaves proteins after Asp residues. Caspases are initially expressed as zymogens, in which a large subunit is N-terminal to a small subunit. Caspases are generally activated by cleavage at internal Asp residues (FIG. 1A). These proteins have been identified in many eukaryotes, including C. elegans, Drosophila, mouse, and humans. Currently, there are at least 14 known caspase genes, named caspase-1 through caspase-14. Caspases are found in myriad organisms, including human, mouse, insect (e.g., Drosophila), and other invertebrates (e.g., C. elegans). In Table 1, ten human caspases are listed along with their alternative names. The nucleotide and amino acid sequences of representative human caspase gene products are presented in SEQ ID NOs:4–33 and FIGS. 11–20.

| Caspase | Alternative name |
| --- | --- |
| Caspase-1 | ICE |
| Caspase-2 | ICH-1 |
| Caspase-3 | CPP32, Yama, apopain |
| Caspase-4 | $ICE_{rel}II$; TX, ICH-2 |
| Caspase-5 | $ICE_{rel}III$; TY |
| Caspase-6 | Mch2 |
| Caspase-7 | Mch3, ICE-LAP3, CMH-1 |
| Caspase-8 | FLICE; MACH; Mch5 |
| Caspase-9 | ICE-LAP6; Mch6 |
| Caspase-10 | Mch4, FLICE-2 |

As used herein, "rev-caspase" refers to a cysteine protease that specifically cleaves proteins after Asp residues and is expressed as a zymogen, in which a small subunit is N-terminal to a large subunit.

Within the context of this invention, it should be understood that a caspase or rev-caspase includes wild-type protein sequences, as well as other variants (including alleles) of the native protein sequence. Briefly, such variants may result from natural polymorphisms or may be synthesized by recombinant methodology, and differ from wild-type protein by one or more amino acid substitutions, insertions, deletions, or the like. Typically, when engineered, amino acid substitutions will be conservative, i.e., substitution of amino acids within groups of polar, non-polar, aromatic, charged, etc. amino acids. In the region of homology to the native sequence, variants should preferably have at least 90% amino acid sequence identity, and within certain embodiments, greater than 92%, 95%, or 97% identity.

As will be appreciated by those skilled in the art, a nucleotide sequence encoding a caspase, rev-caspase or variant may differ from the known native sequences, due to codon degeneracies, nucleotide polymorphisms, or amino acid differences. In other embodiments, variants should preferably hybridize to the native nucleotide sequence at conditions of normal stringency, which is approximately 25–30° C. below Tm of the native duplex (e.g., 5×SSPE, 0.5% SDS, 5×Denhardt's solution, 50% formamide, at 42° C. or equivalent conditions; see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987). Low stringency hybridizations utilize conditions approximately 40° C. below Tm, and high stringency hybridizations utilize conditions approximately 10° C. below Tm. Variants preferably have at least 75% nucleotide identity to native sequence, preferably at least 80%, 85%, and most preferably at least 90% nucleotide identity.

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

A. Caspase and Rev-caspase Genes and Gene Products

As noted above, the invention provides compositions relating to caspase and rev-caspase genes and gene products, and methods for the use of the genes and gene products. In particular, the invention provides rev-caspase constructs that are active when expressed in cells. Given the disclosure provided herein, a caspase gene can be isolated from a variety of cell types and engineered to produce a rev-caspase.

1. Isolation of Caspase Genes

The present invention, as described herein, provides rev-caspase genes, which are constructed from caspase genes. Caspase genes may be isolated from either genomic DNA or preferably cDNA. Isolation of caspase genes from genomic DNA or cDNA typically can proceed by, first, generating an appropriate DNA library through techniques for constructing libraries that are known in the art (see Sambrook et al., *Molecular Cloning: A Laboratory Manual,* Cold Spring Harbor Press, 1989) or purchased from commercial sources (e.g., Clontech, Palo Alto, Calif.). Briefly, cDNA libraries can be constructed in bacteriophage vectors (e.g., λZAPII), plasmids, or others, which are suitable for screening, while genomic DNA libraries can be constructed in chromosomal vectors, such as YACs (yeast artificial chromosomes), bacteriophage vectors, such as λEMBL3, λgt10, cosmids, or plasmids.

In one embodiment known caspase sequences may be utilized to design an oligonucleotide hybridization probe suitable for screening genomic or cDNA libraries. Preferably, such oligonucleotide probes are 20–30 bases in length. To facilitate hybridization detection, the oligonucleotide may be conveniently labeled, generally at the 5' end, with a reporter molecule, such as a radionuclide, (e.g., $^{32}P$), enzymatic label, protein label, fluorescent label, or biotin. Such libraries are then generally plated as phage or colonies, depending upon the vector used. Subsequently, a nitrocellulose or nylon membrane, to which the colonies or phage have been transferred, is probed to identify candidate clones which contain the caspase gene. Such candidates may be verified as containing caspase DNA by any of various means including, for example, DNA sequence analysis or hybridization with a second, non-overlapping probe.

Once a library is identified as containing a caspase gene, the gene can be isolated by amplification. Briefly, when using cDNA library DNA as a template amplification primers are designed based upon known caspase gene sequences (see GenBank Accession Nos. X65019 (caspase-1), U13021 (caspase-2), U13737 (caspase-3), U25804 (caspase-4), U28015 (caspase-5), U20536 (caspase-6), U37448 (caspase-7), U60520 (caspase-8), U56390 (caspase-9), U60519 (caspase-10) Y13089 (caspase-11), Y13090 (caspase-12), AF078533 (caspase-13), AF092997 (caspase-14), and sequences provided herein). Amplification of cDNA libraries made from cells with high caspase activity is preferred. Primers for amplification are preferably derived from sequences in the 5' and 3' untranslated region in order to isolate a full-length cDNA. The primers preferably have a GC content of about 50% and contain restriction sites to facilitate cloning and do not have self-complementary sequences nor do they contain complementary sequences at their 3' end (to prevent primer-dimer formation). The primers are annealed to cDNA or genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment is obtained by DNA sequence analysis or indirectly through amino acid sequencing of the encoded protein.

Other methods may also be used to obtain a caspase encoding nucleic acid molecule. For example, a nucleic acid molecule encoding caspase may be obtained from an expression library by screening with an antibody or antibodies reactive to caspase (see, Sambrook, et al. *Molecular Cloning: A Laboratory Manual,* 2nd Ed., Cold Spring Harbor Laboratory Press, NY, 1987; Ausubel, et al. *Current Protocols in Molecular Biology,* Greene Publishing Associates and Wiley-Interscience, NY, 1995).

Caspase genes from a variety of species may be isolated using the compositions provided herein. For closely related species, the human sequence or portion thereof may be utilized as a probe on a genomic or cDNA library. For example, a fragment of caspase that encompasses the catalytic site may be labeled and used as a probe on a library constructed from mouse, primate, rat, dog, or other vertebrate, warm-blooded or mammalian species. An initial hybridization at normal stringency may yield candidate clones or fragments. If no hybridization is initially observed, varying degrees of stringency may be used. (see Sambrook et al. supra, and other well-known sources for stringency conditions) While such probes may also be used to probe libraries from evolutionarily diverse species, such as Drosophila, hybridization conditions will likely be more relaxed.

While relaxed hybridization conditions using probes designed from human sequences may identify caspase genes of evolutionarily diverse species it may be more beneficial to attempt to directly isolate these genes from a library using methods which do not require the human sequence per se. These methods include, but are not limited to, amplification using primers derived from conserved areas, amplification using degenerate primers from various regions, antibody probing of expression libraries, and the like. For example, random-primed amplification (e.g., polymerase chain reaction) may be employed (see, e.g., *Methods Enzymol.* 254: 275, 1995; *Trends Genet.* 11: 242, 1995; Liang and Pardee, *Science* 257: 967, 1992; Welsh et al., *Nucl. Acids Res.* 20: 4965, 1992). In addition, variations of random-primed PCR may also be used, especially when a particular gene or gene family is desired. In such a method, one of the amplification primers is an "anchored oligo(dT) (oligo(dT) dN)" and the other primer is a degenerate primer based upon amino acid or nucleotide sequence of a related gene. A gene sequence is identified as a caspase by amino acid similarity and/or nucleic acid similarity. Generally, amino acid similarity is preferred. Candidate caspase genes are examined for enzyme activity by one of the functional assays described herein or other equivalent assays.

Variants of caspase and rev-caspase genes provided herein may be engineered from natural variants (e.g., polymorphisms, splice variants, mutants), synthesized or constructed. Many methods have been developed for generating mutants (see, generally, Sambrook et al., supra; Ausubel, et al., supra, and the discussion above). Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically *E.* coli, but alternatively, other prokaryotes, yeast or other eukaryotes. Standard screening and vector growth protocols are used to identify mutant sequences and obtain high yields.

Similarly, deletions and/or insertions of the caspase or rev-caspase genes may be constructed by any of a variety of known methods as discussed supra. For example, the gene can be digested with restriction enzymes and religated such that a sequence is deleted or religated with additional sequences such that an insertion or large substitution is made. Other means of generating variant sequences may be employed with methods known in the art, for example those described in Sambrook et al. (supra) and Ausubel et al. (supra). Verification of variant sequences is typically accomplished by restriction enzyme mapping, sequence analysis, or probe hybridization. Variants which catalyze Asp-specific cleavages are useful in the context of this invention.

B. Rev-Caspases

The caspases of the present invention are generated by rearranging the gene sequence of the caspase gene such that the nucleic acid sequence encoding the small subunit precedes (is 5' to) the nucleic acid sequence encoding the large subunit. These rearranged caspases are called rev-caspases.

1. Structure of Rev-caspases

Figure 10:
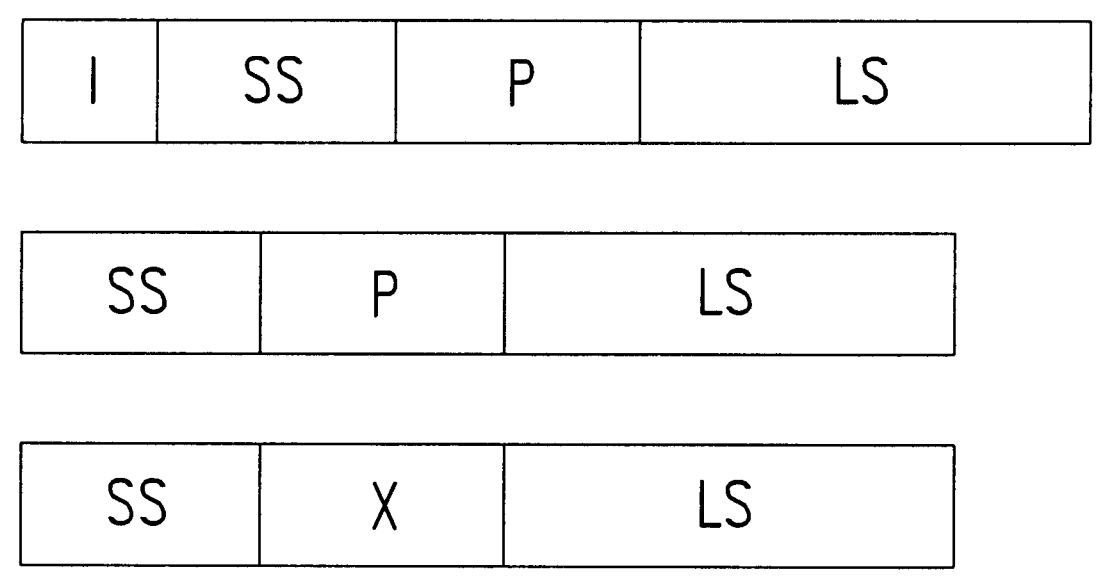

The rev-caspases of the present invention comprise at least a portion of the small subunit and at least a portion of the large subunit. In preferred embodiments, the prodomain or a portion thereof (see FIGS. 1, 10) and/or an intervening sequence or a portion thereof (see FIG. 10) are also present in rev-caspase. In other preferred embodiments, a "linker" region is located between the small and large subunits.

The boundaries of the small subunit and large subunit are identified either experimentally by amino acid sequence analysis of the mature caspase or by inspection of structural homology (e.g., the conserved Asp-X cleavage site). For exemplary purposes, the Table below presents the boundaries of the prodomain (P), large subunit (LS), intervening sequence (I), and small subunit (SS) of human caspase-1 through -10. The nucleotide numbers refer to the nucleotides in SEQ ID NOs:4–33 and in FIGS. 11–20.

| Caspase | Prodomain | Large Subunit | Intervening sequence | Small Subunit |
|---------|-----------|---------------|---------------------|---------------|
| Caspase-1 | 1–357 | 358–891 | 892–948 | 949–1212 |
| Caspase-2 | 1–456 | 457–948 | 949–990 | 991–1305 |
| Caspase-3 | 1–84 | 85–525 | | 526–831 |
| Caspase-4 | 1–240 | 241–810 | 811–867 | 868–1131 |
| Caspase-5 | 1–363 | 364–933 | | 934–1254 |
| Caspase-6 | 1–69 | 70–537 | 538–579 | 580–879 |
| Caspase-7 | 1–69 | 70–594 | | 595–909 |
| Caspase-8 | 1–681 | 682–1173 | | 1174–1488 |
| Caspase-9 | 1–390 | 391–945 | 946–990 | 991–1248 |
| Caspase-10 | 1–657 | 658–1116 | | 1117–1437 |

As noted above, a portion of the large subunit and small subunit may be used in rev-caspase constructs. When designing rev-caspases that contain a portion of these subunits, the active site (e.g., QACXG, where X is Arg, Gln, or Gly); (SEQ ID NO:51), which is located near the C-terminus of the large subunit should not be deleted if protease activity is desired. Preferably, the 3-dimensional structure as determined by X-ray crystallography (see Mittl et al., *J. Biol. Chem.*, 272: 6539–6547, 1997; Rotondu et al., *Nat. Struct. Biol.*, 3: 619–625, 1996; Walker et al., *Cell*, 78: 343–352, 1994; Wilson et al., *Nature*, 370: 270–275, 1994) is maintained. For example, from the x-ray crystallographic structures of caspases, the amino acids, that are important in binding substrates have been identified. Likewise, substitutions of amino acids in the active site may be detrimental to maintaining activity. Although it is preferred that both subunits are derived from the same caspase, combinations of subunits from different caspases and/or from different species may be used.

The prodomain (sometimes called an N-terminal peptide) is generally not required for enzyme activity and is normally released in vivo. Rev-caspases of the present invention optionally have a prodomain or portion thereof. Similarly, the intervening sequence, which is present in certain caspases, is optional for inclusion in rev-caspases.

In certain embodiments, a linker region is engineered between the small and large subunits. A "linker region", as used herein, refers to a peptide of from about 5 to about 50 amino acids. In preferred embodiments, the linker may contain a protease sensitive or cleavage site. Any site recognized by an intracellular protease may be used. In addition, multiple protease sensitive sites may be tandemly arranged in the same linker. Preferred protease sensitive sites are susceptible to cleavage by caspases or by viral proteases. Preferred caspase sensitive sites include, but are not limited to DXXDG (wherein X is any amino acid; SEQ ID NO:37); DEVDG (SEQ ID NO:38), IETDG (SEQ ID NO:39), YVADG (SEQ ID NO:40), YVHDG (SEQ ID NO:41), and WEHDG (SEQ ID NO:42). Furthermore, the Gly residue may be Ala or another small amino acid. The latter three sites are specifically cleaved by caspases-1, -4, and -5. Other sites specifically cleaved by only one or a few caspases are preferred in certain embodiments. Viral proteases cleavage sites include, but are not limited to, those recognized and cleaved by HIV protease, HCV (hepatitis C virus) protease, HBV (hepatitis B virus) protease, and rhinovirus protease.

2. Construction of Rev-caspases

Rev-caspases may be constructed from caspase sequences by a variety of methods known in the art. A preferred method is amplification (e.g., polymerase chain reaction (PCR)) to selectively amplify the individual subunits and place these in cloning vectors such as pUC such as described in Example 1. Moreover, such PCR reactions can be performed in a variety of ways such that the primers used for amplification contain specific restriction endonuclease sites to facilitate insertion into a vector.

Further, a variety of other methodologies besides PCR may be used to attain the desired rearrangement. For example, one skilled in the art may employ isothermal methods to amplify the nucleotide sequence of interest, using existing restriction endonuclease sites present in the nucleotide sequence to excise and insert sequences, or by the introduction of distinct restriction endonuclease sites by site-directed mutagenesis followed by excision and insertion. These and other methods are described in Sambrook et al., supra; Ausubel, et al., supra. Briefly, one methodology is to generate single-stranded cDNA of the caspase of interest, followed by annealing a primer, which is complementary except for the desired alteration (e.g., a small insertion, deletion, or mutation such that a unique restriction site is created between the large and small subunits and/or at the 5' and 3' ends of both subunits). Bacterial cells are transformed and screened for those which contain desired construct. This construct is then digested to liberate the subunit sequences, which can then be purified and religated into the appropriate orientation.

As indicated above, rev-caspase genes may be manipulated to contain insertions, deletions or substitutions. Moreover, such variant rev-caspase genes useful in the context of this invention include those which facilitate Asp-specific cleavages indicative of caspase activity.

Further, variants which are incapable of being cleaved into separate subunits are encompassed within the context of this invention, if those variants are able to facilitate Asp-specific cleavages by way of a cysteine-containing active site. By way of guidance, amino acids involved in catalysis, Asp recognition in substrate, and P2-P4 substrate recognition are provided in FIG. 6.

C. Vectors, Host Cells and Means of Expressing and Producing Protein

Caspase may be expressed in a variety of host organisms. In certain embodiments, caspase is produced in bacteria, such as E. coli, or mammalian cells (e.g., CHO and COS-7), for which many expression vectors have been developed and are available. Other suitable host organisms include other bacterial species, and eukaryotes, such as yeast (e.g., Saccharomyces cerevisiae), and insect cells (e.g., Sf9).

A DNA sequence encoding rev-caspase is introduced into an expression vector appropriate for the host. In certain embodiments, rev-caspase is inserted into a vector such that a fusion protein is produced. The rev-caspase sequence is derived as described herein. As discussed above, the sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At minimum, the vector must contain a promoter sequence. As used herein, a "promoter" refers to a nucleotide sequence that contains elements that direct the transcription of a linked gene. At minimum, a promoter contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked".

Other regulatory sequences may be included. Such sequences include a transcription termination signal sequence, secretion signal sequence, origin of replication, selectable marker, and the like. The regulatory sequences are operationally associated with one another to allow transcription or translation.

The expression vectors used herein include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009) and the like.

The promoter controlling transcription of rev-caspase may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the E. coli lacI repressor responsive to IPTG induction, the temperature sensitive λc1857 repressor, and the like. The E. coli lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in the host cells. Thus, when the host cell is a bacterium, the vector preferably contains a bacterial origin of replication. Preferred bacterial origins of replication include the fl-ori and col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk-hosts). However, drug markers are also available (e.g., G418 resistance and hygromycin resistance).

The sequence of nucleotides encoding rev-caspase may also include a secretion signal, whereby the resulting peptide is a precursor protein processed and secreted. The resulting processed protein may be recovered from the periplasmic space or the fermentation medium. Secretion signals suitable for use are widely available and are well known in the art (von Heijne, J. Mol. Biol. 184: 99–105, 1985). Prokaryotic and eukaryotic secretion signals that are functional in E. coli (or other host) may be employed. The presently preferred secretion signals include, but are not limited to, those encoded by the following E. coli genes: pelB (Lei et al., J. Bacteriol. 169: 4379, 1987), phoA, ompA, ompT, ompF, ompC, beta-lactamase, and alkaline phosphatase.

One skilled in the art appreciates that there are a wide variety of suitable vectors for expression in bacterial cells and which are readily obtainable. Vectors such as the pET series (Novagen, Madison, Wis.), the tac and trc series (Pharmacia, Uppsala, Sweden), pTTQ18 (Amersham International plc, England), pACYC 177, pGEX series, and the like are suitable for expression of a rev-caspase. Baculovirus vectors, such as pBlueBac (see, e.g., U.S. Pat. Nos. 5,278, 050, 5,244,805, 5,243,041, 5,242,687, 5,266,317, 4,745,051, and 5,169,784; available from Invitrogen, San Diego) may be used for expression in insect cells, such as Spodoptera frugiperda sf9 cells (see, U.S. Pat. No. 4,745,051). The choice of a bacterial host for the expression of a rev-caspase is dictated in part by the vector. Commercially available vectors are paired with suitable hosts.

A wide variety of suitable vectors for expression in eukaryotic cells are available. Such vectors include pCMVLacI, pXT1 (Stratagene Cloning Systems, La Jolla, Calif.); pCDNA series, pREP series, pEBVHis (Invitrogen, Carlsbad, Calif.). In certain embodiments, rev-caspase gene is cloned into a gene targeting vector, such as pMClneo, a pOG series vector (Stratagene Cloning Systems).

Rev-caspase is isolated by standard methods, such as affinity chromatography, size exclusion chromatography, metal ion chromatography, ionic exchange chromatography, HPLC, and other known protein isolation methods. (see generally Ausubel et al. supra; Sambrook et al. supra). An isolated purified protein gives a single band on SDS-PAGE when stained with Coomassie blue.

Rev-caspase may be expressed as a hexa-his fusion protein and isolated by metal-containing chromatography, such as nickel-coupled beads. Briefly, a sequence encoding $His_6$ is linked to a DNA sequence encoding a rev-caspase. Although the $His_6$ sequence can be positioned anywhere in the molecule, preferably it is linked at the 3' end immediately preceding the termination codon. The fusion may be constructed by any of a variety of methods. A convenient method is amplification of the rev-caspase gene using a downstream primer that contains the codons for $His_6$.

Purified rev-caspase protein may be used in assays to screen for inhibitory drugs. These assays may be performed in vitro or in vivo and utilize any of the methods described herein or that are known in the art. The protein may also be crystallized and subjected to X-ray analysis to determine its 3-dimensional structure or used to raise antibodies.

D. Uses of Rev-caspase Gene and Gene Product

1. Inhibitors and Enhancers of Caspase Activity

Candidate inhibitors and enhancers may be isolated or procured from a variety of sources, such as bacteria, fungi, plants, parasites, libraries of chemicals, peptides or peptide derivatives and the like. Inhibitors and enhancers may be also be rationally designed, based on the protein structure determined from X-ray crystallography (see, Mittl et al., *J. Biol. Chem.*, 272: 6539–6547, 1997). In certain preferred embodiments, the inhibitor targets a specific caspase (e.g., caspase-3 and not any other caspases).

Without being held to a particular mechanism, the inhibitor may act by preventing processing of caspase or by preventing enzymatic activity, or by other mechanism. The inhibitor may act directly or indirectly. In preferred embodiments, inhibitors interfere in the processing of the caspase protein. In other preferred embodiments, the inhibitors are small molecules. In a most preferred embodiment, the inhibitors prevent apoptosis. Inhibitors should have a minimum of side effects and are preferably non-toxic. Inhibitors that can penetrate cells are preferred.

In addition, enhancers of caspase activity or expression are desirable in certain circumstances. At times, increasing apoptosis will have a therapeutic effect. For example, tumors or cells that mediate autoimmune diseases are appropriate cells for destruction. Enhancers may increase the rate or efficiency of caspase processing, increase transcription or translation, or act through other mechanisms. As is apparent to one skilled in the art, many of the guidelines presented above apply to the design of enhancers as well.

Screening assays for inhibitors and enhancers will vary according to the type of inhibitor or enhancer and the nature of the activity that is being affected. Assays may be performed in vitro or in vivo. In general, in vitro assays are designed to evaluate caspase protein processing or caspase enzymatic activity, and in vivo assays are designed to evaluate caspase protein processing, caspase enzymatic activity, apoptosis, or caspase cleavage of substrate. In any of the assays, a statistically significant increase or decrease compared to a proper control is indicative of enhancement or inhibition.

One in vitro assay can be performed by examining the effect of a candidate compound on processing of rev-caspase into two subunits. Briefly, a cleavable form of rev-caspase, that is a primary translation product, is obtained from an in vitro translation system. The cleavable form of rev-caspase is preferably constructed to be auto-cleaved, but can be constructed to be cleaved by other protease components present or added to the reaction. This primary product is contacted with or without or translated in the presence or absence of a candidate compound and assessed for appearance of the two subunits to facilitate detection, typically, the primary product of rev-caspase is labeled during translation, cell viability, and the like. The two subunits may be readily detected by autoradiography after gel electrophoresis. One skilled in the art will recognize that other methods of labeling and detection may be used alternatively.

An alternative in vitro assay is designed to measure cleavage of a caspase substrate (e.g., Acetyl DEVD-aminomethyl coumarin (amc) (SEQ ID NO:52), lamin, PRPP, and the like). Substrate turnover may be assayed using either cleavable or noncleavable rev-caspase. Briefly, in this method, rev-caspase is translated and allowed sufficient time to be processed, if a cleavable rev-caspase is being used. The caspase substrate along with the candidate compound is added to the reaction. Detection of cleaved substrate is performed by any one of a variety of standard methods. Generally, the substrate will be labeled and followed by an appropriate detection means.

Moreover, any known enzymatic analysis can be used to follow the inhibitory or enhancing ability of a candidate compound with regard to a rev-caspase of this invention. For example, one could express the rev-caspase of interest in a cell line be it bacterial, insect, mammalian or other, either in cleavable or noncleavable form and purify the rev-caspase. The purified rev-caspase could then be used in a variety of assays to follow its catalytic ability in the presence of candidate compounds, as noted above. Such methods of expressing and purifying recombinant proteins are known in the art and examples can be found in Sambrook et al., *Molecular Cloning: A Laboratory Manual,* Cold Spring Harbor Press, 1989 as well as in a number of other sources.

In vivo assays are typically performed in cells transfected either transiently or stably with an expression vector containing a rev-caspase gene, such as those described herein. These cells are used to measure rev-caspase processing, substrate turnover, or apoptosis in the presence or absence of a candidate compound. When assaying apoptosis, a variety of cell analyses may be used including, for example, dye staining and microscopy to examine nucleic acid fragmentation and porosity of the cells. Further, in vivo assaying for the ability of the transfected rev-caspase to cleave known substrates that are co-transfected or placed in the cell culture media in the presence of the candidate compound can be performed thereby allowing for the detection and determination of substrate turnover.

The assays briefly described herein may be used to identify an enhance or inhibitor that is specific for an individual caspase. In a preferred embodiment candidate compounds would be analyzed using a variety of rev-caspases (e.g., rev-caspase-1 through rev-caspase-14) to identify specific for individual caspases.

A variety of methodologies exist can be used to investigate the effect of a candidate compound. Such methodologies are those commonly used to analyze enzymatic reactions and include, for example, SDS-PAGE, spectroscopy, HPLC analysis, autoradiography, chemiluminescence, chromogenic reactions, and immunochemistry (e.g., blotting, precipitating, etc.).

Inhibitors and enhancers may be used in the context of this invention to exert control over the cell death process or cytokine activation (e.g., IL-1, which is activated by caspase-1). Thus, these inhibitors and enhancers will have utility in diseases characterized by either excessive or insufficient levels of apoptosis. Inhibitors of proteases have potential to treat the major neurodegenerative diseases: stroke, Parkinson's Disease, Alzheimer's Disease, and ALS. As well, caspase protease inhibitors may be used to inhibit apoptosis in the heart following myocardial infarction, in the kidney following acute ischemia, and in diseases of the liver. In other embodiments, inhibitors of caspase-1 can be used to inhibit the release of the pro-inflammatory IL-1β, and thus may provide therapeutic benefit in treating inflammation and/or autoimmune disorders. Enhancers of caspase activity may be used in contexts when apoptosis or cytokine activation are desired. For example, inducing or increasing apoptosis in cancer cells or aberrantly proliferating cells may be effected by delivery of a caspase enhancer.

The inhibitors and enhancers may be further coupled with a targeting moiety that binds a cell surface receptor specific to the cells. Administration of inhibitors or enhancers will generally follow established protocols. The compounds of the present invention may be administered either alone, or as a pharmaceutical composition. Briefly, pharmaceutical compositions of the present invention may comprise one or more of the inhibitors or enhancers as described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

2. Gene Therapy

As noted above, rev-caspases may be delivered to cells as part of gene delivery vehicles. In many diseases and syndromes, too little apoptosis is an important feature in their development. Treatment of many autoimmune diseases and tumors would benefit from increased apoptosis. One means to increase apoptosis is to provide target cells with caspase genes in an expressible form. This may be accomplished by delivery of DNA or cDNA capable of in vivo transcription of the rev-caspase. More specifically, in order to produce rev-caspases in vivo, a nucleic acid sequence coding for the rev-caspase is placed under the control of a eukaryotic promoter (e.g., a pol III promoter, CMV or SV40 promoter). Where it is desired to more specifically control transcription, the rev-caspase may be placed under the control of a tissue or cell specific promoter (e.g., to target cells in the liver), or an inducible promoter, such as metallothionein.

Many techniques for introduction of nucleic acids into cells are known. Such methods include retroviral vectors and subsequent retrovirus infection, adenoviral or adeno-associated viral vectors and subsequent infection, and complexes of nucleic acid with a condensing agent (e.g., polylysine). These complexes or viral vectors may be targeted to particular cell types by way of a ligand incorporated into the vehicle. Many ligands specific for tumor cells and other cells are well known in the art.

A wide variety of vectors may be utilized within the context of the present invention, including for example, plasmids, viruses, retrotransposons and cosmids. Representative examples include adenoviral vectors (e.g., WO 94/26914, WO 93/9191; Yei et al., *Gene Therapy* 1: 192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218.

Within certain aspects of the invention, nucleic acid molecules that encode the rev-caspase may be introduced into a host cell utilizing a vehicle, or by various physical methods. Representative examples of such methods include transformation using calcium phosphate precipitation (Dubensky et al., *PNAS* 81: 7529–7533, 1984), direct microinjection of such nucleic acid molecules into intact target cells (Acsadi et al., *Nature* 352: 815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89: 6094, 1990), lipofection (Felgner et al., *Proc. Natl. Acad. Sci. USA* 84: 7413–7417, 1989), microprojectile bombardment (Williams et al., *PNAS* 88: 2726–2730, 1991), polyeation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29: 69, 1985; and Friedmann et al., *Science* 244: 1275, 1989), and DNA ligand (Wu et al, *J. of Biol. Chem.* 264: 16985–16987, 1989), as well as psoralen inactivated viruses such as Sendai or Adenovirus. In one embodiment, the rev-caspase construct is introduced into the host cell using a liposome.

As noted above, pharmaceutical compositions also are provided by this invention. These compositions may contain any of the above described inhibitors, enhancers, DNA molecules, vectors or host cells, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, including for example intraarticularly, intracranially, intradermally, intrahepatically, intramuscularly, intraocularly, intraperitoneally, intrathecally, intravenously, subcutaneously or even directly into a tumor. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition. Pharmaceutical compositions are useful for both diagnostic or therapeutic purposes.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

The following examples are offered by way of illustration, and not by way of limitation.

EXAMPLES

Example 1

Generation of cDNAs Expressing Rev-caspase-3 and 6 Precursors

Generation of cDNAs encoding rev-caspase-3 and 6 precursors were generated by PCR. The large (LS) and small subunits (SS) of caspase-3 were amplified with the following primers using the caspase-3 cDNA as a template:

```
LS-forward,  ATGGAGAACACTGAAAACTCAG          (SEQ ID NO:43);
LS-reverse,  GTCATCATCAACACCTCAGTCT          (SEQ ID NO:44);
SS-forward,  GGATCCATGATTGAGACAGACAGTGG      (SEQ ID NO:45);
SS-reverse,  ATCAACTTCATCGTGATAAAAATAGAGTTC  (SEQ ID NO:46).
```

The PCR products were cloned separately into the Sma I site of pBluescript KS+. The small subunit was then excised from KS+-vector with Bam HI and inserted into the Bam HI site of the second KS+-vector which contains the large subunit. This places the small subunit in-frame 5' to the large subunit. Rev-caspase-6 was amplified and cloned in the KS+-vector in a similar way. The following PCR primers were used with caspase-6-His6 cDNA as a template:

```
LS-forward,  ATGAGCTCGGCCTCGGGG                      (SEQ ID NO:47);
LS-reverse,  TTAATCTACTACATCCAAAGG                   (SEQ ID NO:48);
SS-forward,  GGATCCATGGTAGAAATAGATGCAGCCTCCGTTTAC    (SEQ ID NO:49)
SS-reverse,  ATCAATTTCAACGTGGTGGTGGTGGTGC            (SEQ ID NO:50).
```

The resulting nucleotide sequences were such that the wild type subunit order was reversed thus creating a contiguous nucleotide sequence wherein the coding region for the small subunit preceded that of the large subunit (See FIG. 1). The engineered contiguous caspase-3 and 6 molecules (i.e., rev-caspase molecules) in which the SS was fused in frame N-terminal to the LS, and a cleavage site (DEVDG in the case of caspase-3; VEIDS in the case of caspase-6 (these internal cleavage sites were designed to be specific for the caspase in which it was introduced in order to investigate the autocatalytic activity of the particular caspase)) was introduced between the two subunits and is depicted in FIG. 1B and C.

To express the rev-caspases in bacteria, their cDNAs were excised with Bam HI/Xho I and subcloned into the bacterial expression vector pET28a (Novagen, Inc.) in-frame with the T7-tag of this vector.

Example 2

Expression of Rev-caspase in Mammlian Cells and Assay for Apoptosis

To express the rev-caspases in mammalian cells and assay their apoptotic activity, they were amplified with the T7-tag primer and the LS-reverse primers using the pET28a constructs as templates, and subcloned into the mammalian double expression vector pRSC-LacZ (MacFarlane et al., *J. Biol. Chem.*, 272: 25417–25420, 1997; Tsang et al., *Bio/Technology*, 22: 68, 1997). This vector allows the expression of lacZ under the Rous Sarcoma virus promoter, and the test cDNA under the CMV promoter. To assay for apoptosis, MCF-7 or 293 cells were transfected, using the method commercially available as the Lipofect Amine method (Life Technologies, Inc.), with the pRSC-LacZ constructs in the presence or absence of different apoptosis-inhibitors. 30 h after transfection cells were stained with β-galactosidase and examined for morphological signs of apoptosis. The percentage of round blue apoptotic cells (mean±SD) were represented as a function of total blue cells under each condition (n≧3).

Example 3

In Vitro Translation of Caspases $^{35}$S-labeled caspases (wild-type and rev-caspases) were obtained by in vitro translation in the presence of $^{35}$S-methionine using a coupled transcription/translation system in rabbit reticulocyte lysate using TNT Kit (Promega) according to the manufacturer's recommendations. Unlike the wild-type caspase-3 and 6, FIG. 2A demonstrates that rev-caspase-3 and 6 were able to undergo autocatalytic processing in the in vitro translation reaction. Further, this processing was completely inhibited by mutation of the active site Cys of rev-caspase-3 and 6 (FIG. 2A, lanes 3 and 6) and by selected caspase inhibitors (See Example 4). Because the in vitro translated products are present at very low concentration in the reaction mixture, the observed cleavage must be attributed to an intramolecular processing within the caspase heterotetramer.

Example 4

Effects of Inhibitors on Rev-caspase-3 and 6 Activity

To test the effect of selected caspase inhibitors on the autocatalytic activity of rev-caspase-3 and 6, the rev-caspases were translated as in Example 3, but in the presence of varying amounts of inhibitors. As demonstrated by FIG. 2B, in the presence of increasing amounts of DEVD-CHO (SEQ ID NO:52), a decrease in the amount of cleavage products and a corresponding increase in the amount of the revcaspase-3 precursor was observed. This corresponded to nearly 50–90% inhibition of the autocatalytic activity of rev-caspase-3 at 40–400 nM concentration. However, the same concentrations of this inhibitor had little effect on the autocatalytic activity of rev-caspase-6 (FIG. 2C). This is consistent with earlier observations that caspase-6 is poorly inhibited by DEVD-CHO (SEQ ID NO:52); see Srinivasula et al., *J. Biol. Chem.*, 271: 27099–27106, 1996. On the other hand, as is apparent from inspection of FIGS. 2B and 2C, z-VAD-fmk had nearly an equal inhibitory effect on rev-caspase-3 and 6 autocatalytic activity at the concentration used in this experiment. Nevertheless, nearly 10-fold more of z-VAD-fink than DEVD-CHO (SEQ ID NO:52) was required to obtain complete inhibition of caspase-3 activity. Similarly, baculovirus p35 had nearly an equal inhibitory effect on rev-caspase-3 and 6 autocatalytic activity (data not shown).

Example 5

Caspase-3 and 6 Specificity Retention of Bacterially Expressed Rev-caspase-3 and -6

Figure 3A:
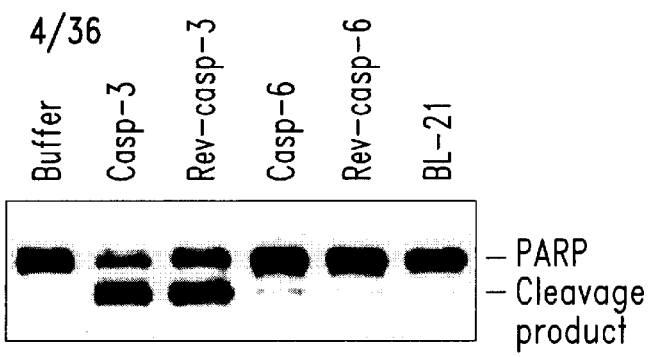
FIGS. 3A and B are scanned images representing the SDS-PAGE analysis of the ability of rev-caspase-3 (imaged by western blot) and -6 (imaged by autoradiogram) to cleave PARP and lamin, respectively.
Figure 3B:
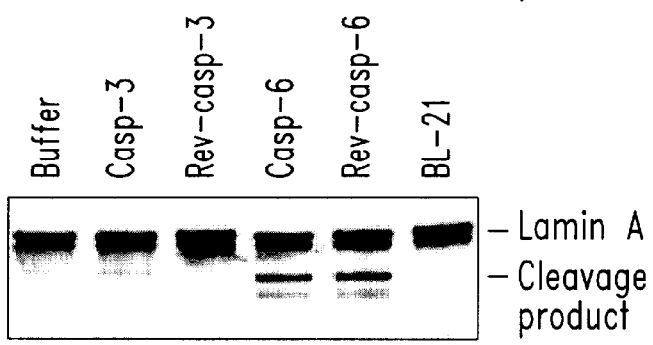
In FIG. 3B a cDNA encoding the C-terminus of lamin A (amino acids) which contain the caspase-6 cleavage site (VEIDA); (SEQ ID NO:116), was amplified by PCR and in vitro translated in the presence of $^{35}$S-methionine. The labeled product was incubated with buffer (lane 1) or the BL-21 bacterial extracts listed above for 2 h at 37° C., and then analyzed by SDS-PAGE and autoradiography. The cleavage products are indicated to the right.

At limited caspase concentrations, poly(ADP) ribose polymerase (PARP) is specifically cleaved by caspase-3 and 7 but not other caspases. Similarly, lamin is specifically cleaved by caspase-6 but not other caspases. To compare the activity of the wild-type and rev-caspase-3 and 6 towards PARP and lamin, rev-caspase-3 and 6 were expressed in bacteria and then incubated with the two substrates PARP and lamin. As shown in FIGS. 3A and B, the activity of the rev-caspases towards these two substrates were indistinguishable from their wild-type counterparts. Both caspase-3 variants (rev and WT), but not caspase-6 variants efficiently cleaved PARP. In contrast, both caspase-6 variants, but not caspase-3 variants efficiently cleaved lamin. These results demonstrate that the mature caspases generated from the rev and the wild type constructs have identical substrate specificity.

Example 6

Induction of Apoptosis in Mammalian Cells by Rev-caspase-3 and -6

Figure 4A:
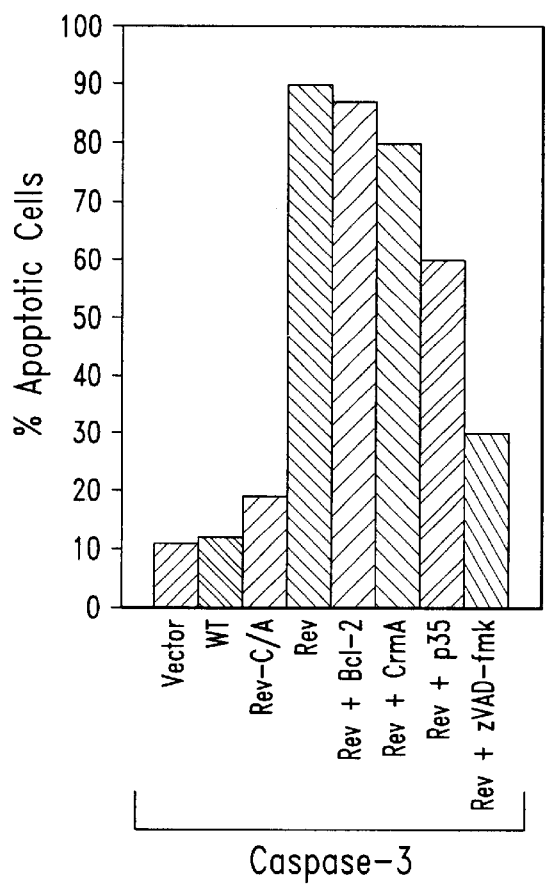
FIGS. 4A and B are bar diagrams representing the ability of rev-caspase-3 and -6 to induce apoptosis in MCF-7 cells. MCF-7 cells were transiently transfected with either rev-caspase-3 (FIG. 4A), or rev-caspase-6 (FIG. 4B) expression constructs in combination with 4-fold of CrmA, p35 or Bcl-2 expression constructs, or 20 μM zVAD-fmk. Cells transfected with an empty vector or the wild-type caspase-3 or -6 were used as controls.
Figure 4B:
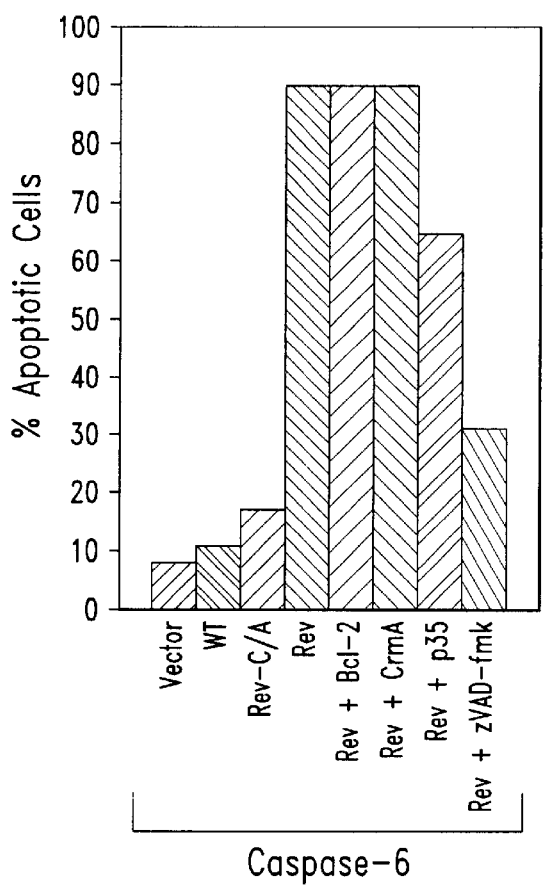

To determine the apoptotic activity of rev-caspase-3 and 6 in vivo, the rev-caspases were expressed in human MCF-7 cells, transfected as explained above in Example 2. As evidenced by FIGS. 4A and B, unlike the wild type caspase-3 and 6, the rev-caspases potently induced apoptosis in nearly 90% of the transfected cells. Overexpression of Bcl-2 or CrmA, which protect against different forms of apoptosis, did not significantly reduce their apoptotic activity. Nevertheless, overexpression of the baculovirus p35, which inhibits the activity of most caspases, partially protected against their apoptotic activity. Also, incubation of the transfected cells in the presence of 100 $\mu$M z-VAD-fmk, dramatically reduced their apoptotic activity to nearly 30%. These data demonstrate directly that the activity of caspase-3 and 6 are downstream of the CrmA and Bcl-2 block in the apoptotic cascade, and can only be inhibited by high concentration of the pancaspase-inhibitor z-VAD-fmk.

Example 7

Activity of Noncleavable Rev-caspase-3

To demonstrate that the rev-caspase molecules are inherently active and do not require separation of the two subunits and that the two subunits are derived from the same contiguous molecule, the DEVD (SEQ ID NO:52) site was removed and Asp9 and 28, that are present between the two subunits of rev-caspase-3, were mutated (see FIG. 2A). However, to follow the activity of this molecule a cleavable 35 residue long His6-T7-tag N-terminal to the IETD (SEQ ID NO:53) site was introduced (see FIG. 1B). FIG. 5 demonstrates that upon in vitro translation of this molecule, as described in Example 3 above, there was no evidence of cleavage between the two subunits. Nevertheless, the translated molecule was active as evident from its ability to cleave its T7-tag to form the p32 species (FIG. 5). In the presence of 400 nM DEVD-CHO (SEQ ID NO:52), processing of the T7-tag was inhibited and only the full length p34 species can be seen. Furthermore, expression of this molecule into MCF-7 cells potently induced apoptosis in these cells. These data demonstrate that when the two subunits of a caspase are rearranged in the reverse order, it is not necessary to separate them from each other to generate an active caspase. Thus by mimicking the mature caspase structure, it is possible to design a contiguous active caspase molecules.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method of identifying an inhibitor or enhancer of caspase processing activity, comprising:

(a) contacting a sample containing an in vitro translated rev-caspase with a candidate inhibitor or candidate enhancer; and (b) detecting the presence of large and small subunits of rev-caspase, and therefrom determining the level of caspase processing activity, wherein a decrease in processing indicates the presence of a caspase inhibitor, and wherein an increase in processing indicates the presence of a caspase enhancer, wherein processed rev-caspase yields large and small subunits.

2. A method of identifying an inhibitor or enhancer of caspase processing activity, comprising:

(a) contacting a cell transfected with a vector expressing rev-caspase with a candidate inhibitor or candidate enhancer; and (b) detecting the presence of large and small subunits of rev-caspase, and therefrom determining the level of caspase processing activity, wherein a decrease in processing indicates the presence of a caspase inhibitor, and wherein an increase in processing indicates the presence of a caspase enhancer, wherein processed rev-caspase yields large and small subunits.

3. A method of identifying an inhibitor or enhancer of caspase-mediated apoptosis, comprising:

(a) contacting a cell transfected with a vector expressing rev-caspase with a candidate inhibitor or candidate enhancer or with a reference compound; and (b) detecting cell viability, wherein viability of cells contacted with a candidate is increased in the presence of an inhibitor and is decreased in the presence of an enhancer compared to cells contacted with a reference compound.

4. The method of any one of claims 1–3, wherein the rev-caspase is selected from the group consisting of rev-caspase-1, rev-caspase-2, rev-caspase-3, rev-caspase-4, rev-caspase-5, rev-caspase-6, rev-caspase-7, rev-caspase-8, rev-caspase-9, rev-caspase-10, rev-caspase-11, rev-caspase-12, rev-caspase-13, and rev-caspase-14.

5. The method of either of claims 1 or 2, wherein detecting comprises gel electrophoresis.

6. The method of claim 1, wherein the in vitro translated rev-caspase is labeled.

7. The method of claim 6, wherein the label is a radioactive label, a peptide tag, an enzyme or biotin.

* * * * *

SEQUENCE LISTING

<160> NUMBER OF SEQ ID NOS: 116

<210> SEQ ID NO 1
<211> LENGTH: 873
<212> TYPE: DNA
<213> ORGANISM: Artificial Sequence
<220> FEATURE:
<223> OTHER INFORMATION: Rev-Caspase-3 contructed from human caspase -3

<400> SEQUENCE: 1

| | | |
|---|---|---|
| atgattgaga cagacagtgg tgttgatgat gacatggcgt gtcataaaat accagtggag | 60 |
| gccgacttct tgtatgcata ctccacagca cctggttatt attcttggcg aaattcaaag | 120 |
| gatggctcct ggttcatcca gtcgctttgt gccatgctga acagtatgc cgacaagctt | 180 |
| gaatttatgc acattcttac ccgggttaac cgaaaggtgg caacagaatt tgagtccttt | 240 |
| tcctttgacg ctacttttca tgcaaagaaa cagattccat gtattgtttc catgctcaca | 300 |
| aaagaactct attttatca cgatgaagtt gatgggggat cccccatgga gaacactgaa | 360 |
| aactcagtgg attcaaaatc cattaaaaat ttggaaccaa agatcataca tggaagcgaa | 420 |
| tcaatggact ctggaatatc cctggacaac agttataaaa tggattatcc tgagatgggt | 480 |
| ttatgtataa taattaataa taagaatttt cataagagca ctggaatgac atctcggtct | 540 |
| ggtacagatg tcgatgcagc aaacctcagg gaaacattca gaaacttgaa atatgaagtc | 600 |
| aggaataaaa atgatcttac acgtgaagaa attgtgaat tgatgcgtga tgtttctaaa | 660 |
| gaagatcaca gcaaaaggag cagttttgtt tgtgtgcttc tgagccatgg tgaagaagga | 720 |
| ataatttttg gaacaaatgg acctgttgac ctgaaaaaaa taacaaactt tttcagaggg | 780 |
| gatcgttgta gaagtctaac tggaaaaccc aaacttttca ttattcaggc ctgccgtggt | 840 |
| acagaactgg actgtggcat tgagacagac tga | 873 |

<210> SEQ ID NO 2
<211> LENGTH: 858
<212> TYPE: DNA
<213> ORGANISM: Artificial Sequence
<220> FEATURE:
<223> OTHER INFORMATION: Uncleavalbe Rev-Caspase-3 contructed from
      human caspase -3

<400> SEQUENCE: 2

| | | |
|---|---|---|
| atgattgaga cagacagtgg tgttgatgat gacatggcgt gtcataaaat accagtggag | 60 |
| gccgacttct tgtatgcata ctccacagca cctggttatt attcttggcg aaattcaaag | 120 |
| gatggctcct ggttcatcca gtcgctttgt gccatgctga acagtatgc cgacaagctt | 180 |
| gaatttatgc acattcttac ccgggttaac cgaaaggtgg caacagaatt tgagtccttt | 240 |
| tcctttgacg ctacttttca tgcaaagaaa cagattccat gtattgtttc catgctcaca | 300 |
| aaagaactct attttatca cggatccccc atggagaaca ctgaaaactc agtggcttca | 360 |
| aaatccatta aaaatttgga accaaagatc atacatggaa gcgaatcaat ggcctctgga | 420 |
| atatccctgg acaacagtta taaaatggat tatcctgaga tgggtttatg tataataatt | 480 |
| aataataaga attttcataa gagcactgga atgacatctc ggtctggtac agatgtcgat | 540 |
| gcagcaaacc tcagggaaac attcagaaac ttgaaatatg aagtcaggaa taaaaatgat | 600 |
| cttacacgtg aagaaattgt ggaattgatg cgtgatgttt ctaaagaaga tcacagcaaa | 660 |
| aggagcagtt ttgtttgtgt gcttctgagc catggtgaag aaggaataat ttttggaaca | 720 |

-continued

```
aatggacctg ttgacctgaa aaaataaca aacttttca gagggatcg ttgtagaagt      780 ctaactggaa aacccaaact tttcattatt caggcctgcc gtggtacaga actggactgt      840
ggcattgaga cagactga                                                    858

<210> SEQ ID NO 3
<211> LENGTH: 903
<212> TYPE: DNA
<213> ORGANISM: Artificial Sequence
<220> FEATURE:
<223> OTHER INFORMATION: Rev-Caspase-6 contructed from human caspase -3

<400> SEQUENCE: 3
atggtagaaa tagatgcagc ctccgtttac acgctgcctg ctggagctga cttcctcatg       60
tgttactctg ttgcagaagg atattattct caccgggaaa ctgtgaacgg ctcatggtac      120
attcaagatt tgtgtgagat gttgggaaaa tatggctcct ccttagagtt cacagaactc      180
ctcacactgg tgaacaggaa agtttctcag cgccagtgg acttttgcaa agacccaagt      240
gcaattggaa agaagcaggt tcctgttttt gcctcaatgc taactaaaaa gctgcatttc      300
tttccaaaat ctaatctcga gcaccaccac caccaccacg ttgaaattga tggggatcc      360 cccatgagct cggcctcggg gctccgcagg gggcacccgg caggtgggga agaaaacatg      420
acagaaacag atgccttcta taaaagagaa atgtttgatc cggcagaaaa gtacaaaatg      480
gaccacagga gggagaggaat tgctttaatc ttcaatcatg agaggttctt ttggcactta      540
acactgccag aaaggcgggg cacctgcgca gatagagaca atcttacccg caggttttca      600
gatctaggat ttgaagtgaa atgctttaat gatcttaaag cagaagaact actgctcaaa      660
attcatgagg tgtcaactgt tagccacgca gatgccgatt gctttgtgtg tgtcttcctg      720
agccatggcg aaggcaatca catttatgca tatgatgcta aaatcgaaat tcagacatta      780
actggcttgt tcaaaggaga caagtgtcac agcctggttg gaaaacccaa gatatttatc      840
atccaggcat gtcggggaaa ccagcacgat gtgccagtca ttcctttgga tgtagtagat      900
taa                                                                    903

<210> SEQ ID NO 4
<211> LENGTH: 1215
<212> TYPE: DNA
<213> ORGANISM: Homo sapien

<400> SEQUENCE: 4
atggccgaca aggtcctgaa ggagaagaga aagctgttta tccgttccat gggtgaaggt       60
acaataaatg gcttactgga tgaattatta cagacaaggg tgctgaacaa ggaagagatg      120
gagaaagtaa aacgtgaaaa tgctacagtt atggataaga cccgagcttt gattgactcc      180
gttattccga aagggcaca ggcatgccaa atttgcatca catacatttg tgaagaagac      240
agttacctgg cagggacgct gggactctca gcagatcaaa catctggaaa ttaccttaat      300
atgcaagact ctcaaggagt actttcttcc tttccagctc ctcaggcagt gcaggacaac      360
ccagctatgc ccacatcctc aggctcagaa gggaatgtca agctttgctc cctagaagaa      420
gctcaaagga tatggaaaca aaagtcggca gagatttatc caataatgga caagtcaagc      480
cgcacacgtc ttgctctcat tatctgcaat gaagaatttg acagtattcc tagaagaact      540
ggagctgagg ttgacatcac aggcatgaca atgctgctac aaaatctggg gtacagcgta      600
gatgtgaaaa aaaatctcac tgcttcggac atgactacag agctggaggc atttgcacac      660
cgcccagagc acaagacctc tgacagcacg ttcctggtgt tcatgtctca tggtattcgg      720
```

-continued

```
gaaggcattt gtgggaagaa acactctgag caagtcccag atatactaca actcaatgca      780
atctttaaca tgttgaatac caagaactgc ccaagtttga aggacaaacc gaaggtgatc      840
atcatccagg cctgccgtgg tgacagccct ggtgtggtgt ggtttaaaga ttcagtagga      900
gtttctggaa acctatcttt accaactaca gaagagtttg aggatgatgc tattaagaaa      960
gcccacatag agaaggattt tatcgctttc tgctcttcca caccagataa tgtttcttgg     1020
agacatccca caatgggctc tgtttttatt ggaagactca ttgaacatat gcaagaatat     1080
gcctgttcct gtgatgtgga ggaaattttc cgcaaggttc gatttttcatt tgagcagcca    1140 gatggtagag cgcagatgcc caccactgaa agagtgactt tgacaagatg tttctacctc     1200
ttcccaggac attaa                                                      1215
```

<210> SEQ ID NO 5
<211> LENGTH: 1215
<212> TYPE: DNA
<213> ORGANISM: Homo sapien

<400> SEQUENCE: 5

```
taccggctgt tccaggactt cctcttctct ttcgacaaat aggcaaggta cccacttcca      60
tgttatttac cgaatgacct acttaataat gtctgttccc acgacttgtt ccttctctac     120
ctctttcatt ttgcactttt acgatgtcaa tacctattct gggctcgaaa ctaactgagg     180
caataaggct ttccccgtgt ccgtacggtt taaacgtagt gtatgtaaac acttcttctg     240
tcaatggacc gtccctgcga ccctgagagt cgtctagttt gtagaccttt aatggaatta     300
tacgttctga gagttcctca tgaaagaagg aaaggtcgag gagtccgtca cgtcctgttg     360
ggtcgatacg ggtgtaggag tccgagtctt cccttacagt tcgaaacgag ggatcttctt     420
cgagtttcct atacctttgt tttcagccgt ctctaaatag gttattacct gttcagttcg     480
gcgtgtgcag aacgagagta atagacgtta cttcttaaac tgtcataagg atcttcttga    540
cctcgactcc aactgtagtg tccgtactgt tacgacgatg ttttagaccc catgtcgcat    600
ctcacttttt ttttagagtg acgaagcctg tactgatgtc tcgacctccg taaacgtgtg    660
gcgggtctcg tgttctggag actgtcgtgc aaggaccaca agtacagagt accataagcc    720
cttccgtaaa caccccttctt tgtgagactc gttcagggtc tatatgatgt tgagttacgt    780
tagaaattgt acaacttatg gttcttgacg ggttcaaact tcctgtttgg cttccactag    840
tagtaggtcc ggacggcacc actgtcggga ccacaccaca ccaaatttct aagtcatcct    900
caaagacctt tggatagaaa tggttgatgt cttctcaaac tcctactacg ataattcttt     960
cgggtgtatc tcttcctaaa atagcgaaag acgagaaggt gtggtctatt acaaagaacc    1020
tctgtagggt gttacccgag acaaaaataa ccttctgagt aacttgtata cgttcttata    1080
cggacaagga cactacacct cctttaaaag gcgttccaag ctaaaagtaa actcgtcggt    1140
ctaccatctc gcgtctacgg gtggtgactt tctcactgaa actgttctac aaagatggag    1200
aagggtcctg taatt                                                     1215
```

<210> SEQ ID NO 6
<211> LENGTH: 404
<212> TYPE: PRT
<213> ORGANISM: Homo sapien

<400> SEQUENCE: 6

```
Met Ala Asp Lys Val Leu Lys Glu Lys Arg Lys Leu Phe Ile Arg Ser
 1               5                  10                  15
```

```
Met Gly Glu Gly Thr Ile Asn Gly Leu Leu Asp Glu Leu Leu Gln Thr
             20                  25                  30

Arg Val Leu Asn Lys Glu Glu Met Glu Lys Val Lys Arg Glu Asn Ala
             35                  40                  45

Thr Val Met Asp Lys Thr Arg Ala Leu Ile Asp Ser Val Ile Pro Lys
             50                  55                  60

Gly Ala Gln Ala Cys Gln Ile Cys Ile Thr Tyr Ile Cys Glu Glu Asp
 65                  70                  75                  80

Ser Tyr Leu Ala Gly Thr Leu Gly Leu Ser Ala Asp Gln Thr Ser Gly
                 85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
            115                 120                 125

Ser Glu Gly Asn Val Lys Leu Cys Ser Leu Glu Glu Ala Gln Arg Ile
            130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Asn Leu Thr Ala
            195                 200                 205

Ser Asp Met Thr Thr Glu Leu Glu Ala Phe Ala His Arg Pro Glu His
            210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Ile Gln Ala Cys Arg Gly Asp
            275                 280                 285

Ser Pro Gly Val Val Trp Phe Lys Asp Ser Val Gly Val Ser Gly Asn
            290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
            355                 360                 365

Ile Phe Arg Lys Val Arg Phe Ser Phe Glu Gln Pro Asp Gly Arg Ala
            370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 7
<211> LENGTH: 1308
<212> TYPE: DNA
```

<213> ORGANISM: Homo sapien

<400> SEQUENCE: 7

| | | | | | |
|---|---|---|---|---|---|
| atggccgctg | acaggggacg | caggatattg | ggagtgtgtg | gcatgcatcc | tcatcatcag | 60 |
| gaaactctaa | aaagaaccg | agtggtgcta | gccaaacagc | tgttgttgag | cgaattgtta | 120 |
| gaacatcttc | tggagaagga | catcatcacc | ttggaaatga | gggagctcat | ccaggccaaa | 180 |
| gtgggcagtt | tcagccagaa | tgtggaactc | ctcaacttgc | tgcctaagag | gggtccccaa | 240 |
| gcttttgatg | ccttctgtga | agcactgagg | gagaccaagc | aaggccacct | ggaggatatg | 300 |
| ttgctcacca | cccttttctgg | gcttcagcat | gtactccac | cgttgagctg | tgactacgac | 360 |
| ttgagtctcc | cttttccggt | gtgtgagtcc | tgtccccttt | acaagaagct | ccgcctgtcg | 420 |
| acagatactg | tggaacactc | cctagacaat | aaagatggtc | ctgtctgcct | tcaggtgaag | 480 |
| ccttgcactc | ctgaattta | tcaaacacac | ttccagctgg | catataggtt | gcagtctcgg | 540 |
| cctcgtggcc | tagcactggt | gttgagcaat | gtgcacttca | ctggagagaa | agaactggaa | 600 |
| tttcgctctg | gagggatgt | ggaccacagt | actctagtca | ccctcttcaa | gcttttgggc | 660 |
| tatgacgtcc | atgttctatg | tgaccagact | gcacaggaaa | tgcaagagaa | actgcagaat | 720 |
| tttgcacagt | tacctgcaca | ccgagtcacg | gactcctgca | tcgtggcact | cctctcgcat | 780 |
| ggtgtggagg | gcgccatcta | tggtgtggat | gggaaactgc | tccagctcca | agaggttttt | 840 |
| cagctctttg | acaacgccaa | ctgcccaagc | ctacagaaca | aaccaaaaat | gttcttcatc | 900 |
| caggcctgcc | gtggagatga | gactgatcgt | ggggttgacc | aacaagatgg | aaagaaccac | 960 |
| gcaggatccc | ctgggtgcga | ggagagtgat | gccggtaaag | aaaagttgcc | gaagatgaga | 1020 |
| ctgcccacgc | gctcagacat | gatatgcggc | tatgcctgcc | tcaaagggac | tgccgccatg | 1080 |
| cggaacacca | aacgaggttc | ctggtacatc | gaggctcttg | ctcaagtgtt | ttctgagcgg | 1140 |
| gcttgtgata | tgcacgtggc | cgacatgctg | gttaaggtga | acgcacttat | caaggatcgg | 1200 |
| gaaggttatg | ctcctggcac | agaattccac | cggtgcaagg | aaatgtctga | atactgcagc | 1260 |
| actctgtgcc | gccacctcta | cctgttccca | ggacaccctc | ccacatga | | 1308 |

<210> SEQ ID NO 8
<211> LENGTH: 1308
<212> TYPE: DNA
<213> ORGANISM: Homo sapien

<400> SEQUENCE: 8

| | | | | | |
|---|---|---|---|---|---|
| taccggcgac | tgtccctgc | gtcctataac | cctcacacac | cgtacgtagg | agtagtagtc | 60 |
| ctttgagatt | ttttcttggc | tcaccacgat | cggtttgtcg | acaacaactc | gcttaacaat | 120 |
| cttgtagaag | acctcttcct | gtagtagtgg | aacctttact | ccctcgagta | ggtccggttt | 180 |
| cacccgtcaa | agtcggtctt | acaccttgag | gagttaacg | acggattctc | cccaggggtt | 240 |
| cgaaaactac | ggaagacact | tcgtgactcc | ctctggttcg | ttccggtgga | cctcctatac | 300 |
| aacgagtggt | gggaaagacc | cgaagtcgta | catgagggtg | gcaactcgac | actgatgctg | 360 |
| aactcagagg | gaaaaggcca | cacactcagg | acaggggaaa | tgttcttcga | ggcggacagc | 420 |
| tgtctatgac | accttgtgag | ggatctgtta | tttctaccag | gacagacgga | agtccacttc | 480 |
| ggaacgtgag | gacttaaaat | agtttgtgtg | aaggtcgacc | gtatatccaa | cgtcagagcc | 540 |
| ggagcaccgg | atcgtgacca | caactcgtta | cacgtgaagt | gacctctctt | tcttgacctt | 600 |
| aaagcgagac | ctcccctaca | cctggtgtca | tgagatcagt | gggagaagtt | cgaaaacccg | 660 |
| atactgcagg | tacaagatac | actggtctga | cgtgtccttt | acgttctctt | tgacgtctta | 720 |

-continued

```
aaacgtgtca atggacgtgt ggctcagtgc ctgaggacgt agcaccgtga ggagagcgta    780
ccacacctcc cgcggtagat accacaccta cccttttgacg aggtcgaggt tctccaaaaa    840
gtcgagaaac tgttgcggtt gacgggttcg gatgtcttgt ttggttttta caagaagtag    900
gtccggacgg cacctctact ctgactagca ccccaactgg ttgttctacc tttcttggtg    960
cgtcctaggg gacccacgct cctctcacta cggccatttc ttttcaacgg cttctactct   1020
gacgggtgcg cgagtctgta ctatacgccg atacggacgg agtttccctg acggcggtac   1080
gccttgtggt ttgctccaag gaccatgtag ctccgagaac gagttcacaa agactcgcc    1140
cgaacactat acgtgcaccg gctgtacgac caattccact tgcgtgaata gttcctagcc   1200
cttccaatac gaggaccgtg tcttaaggtg gccacgttcc tttacagact tatgacgtcg   1260
tgagacacgg cggtggagat ggacaagggt cctgtgggag ggtgtact              1308
```

<210> SEQ ID NO 9
<211> LENGTH: 435
<212> TYPE: PRT
<213> ORGANISM: Homo sapien

<400> SEQUENCE: 9

```
Met Ala Ala Asp Arg Gly Arg Arg Ile Leu Gly Val Cys Gly Met His
  1               5                  10                  15

Pro His His Gln Glu Thr Leu Lys Lys Asn Arg Val Val Leu Ala Lys
                 20                  25                  30

Gln Leu Leu Leu Ser Glu Leu Leu Glu His Leu Leu Glu Lys Asp Ile
             35                  40                  45

Ile Thr Leu Glu Met Arg Glu Leu Ile Gln Ala Lys Val Gly Ser Phe
 50                  55                  60

Ser Gln Asn Val Glu Leu Leu Asn Leu Leu Pro Lys Arg Gly Pro Gln
 65                  70                  75                  80

Ala Phe Asp Ala Phe Cys Glu Ala Leu Arg Glu Thr Lys Gln Gly His
                 85                  90                  95

Leu Glu Asp Met Leu Leu Thr Thr Leu Ser Gly Leu Gln His Val Leu
            100                 105                 110

Pro Pro Leu Ser Cys Asp Tyr Asp Leu Ser Leu Pro Phe Pro Val Cys
        115                 120                 125

Glu Ser Cys Pro Leu Tyr Lys Lys Leu Arg Leu Ser Thr Asp Thr Val
130                 135                 140

Glu His Ser Leu Asp Asn Lys Asp Gly Pro Val Cys Leu Gln Val Lys
145                 150                 155                 160

Pro Cys Thr Pro Glu Phe Tyr Gln Thr His Phe Gln Leu Ala Tyr Arg
                165                 170                 175

Leu Gln Ser Arg Pro Arg Gly Leu Ala Leu Val Leu Ser Asn Val His
            180                 185                 190

Phe Thr Gly Glu Lys Glu Leu Glu Phe Arg Ser Gly Gly Asp Val Asp
        195                 200                 205

His Ser Thr Leu Val Thr Leu Phe Lys Leu Leu Gly Tyr Asp Val His
    210                 215                 220

Val Leu Cys Asp Gln Thr Ala Gln Glu Met Gln Glu Lys Leu Gln Asn
225                 230                 235                 240

Phe Ala Gln Leu Pro Ala His Arg Val Thr Asp Ser Cys Ile Val Ala
                245                 250                 255

Leu Leu Ser His Gly Val Glu Gly Ala Ile Tyr Gly Val Asp Gly Lys
            260                 265                 270
```

```
Leu Leu Gln Leu Gln Glu Val Phe Gln Leu Phe Asp Asn Ala Asn Cys
        275                 280                 285
Pro Ser Leu Gln Asn Lys Pro Lys Met Phe Phe Ile Gln Ala Cys Arg
        290                 295                 300
Gly Asp Glu Thr Asp Arg Gly Val Asp Gln Gln Asp Gly Lys Asn His
305                 310                 315                 320
Ala Gly Ser Pro Gly Cys Glu Ser Asp Ala Gly Lys Glu Lys Leu
                325                 330                 335
Pro Lys Met Arg Leu Pro Thr Ser Asp Met Ile Cys Gly Tyr Ala
            340                 345                 350
Cys Leu Lys Gly Thr Ala Ala Met Arg Asn Thr Lys Arg Gly Ser Trp
        355                 360                 365
Tyr Ile Glu Ala Leu Ala Gln Val Phe Ser Glu Arg Ala Cys Asp Met
370                 375                 380
His Val Ala Asp Met Leu Val Lys Val Asn Ala Leu Ile Lys Asp Arg
385                 390                 395                 400
Glu Gly Tyr Ala Pro Gly Thr Glu Phe His Arg Cys Lys Glu Met Ser
                405                 410                 415
Glu Tyr Cys Ser Thr Leu Cys Arg His Leu Tyr Leu Phe Pro Gly His
            420                 425                 430
Pro Pro Thr
        435

<210> SEQ ID NO 10
<211> LENGTH: 835
<212> TYPE: DNA
<213> ORGANISM: Homo sapien
<220> FEATURE:
<221> NAME/KEY: misc_feature
<222> LOCATION: (1)...(835)
<223> OTHER INFORMATION: n = A,T,C or G

<400> SEQUENCE: 10
atggagaaca ctgaaaactc agtggattca aaatccatta aaaatttgga accaaagatc      60
atacatggaa gcgaatcaat ggactctgga atatccctgg acaacagtta taaatggat     120
tatcctgaga tgggtttatg tataataatt aataataaga attttcataa aagcactgga    180
atgacatctc ggtctggtac agatgtcgat gcagcaaacc tcagggaaac attcagaaac    240
ttgaaatatg aagtcaggaa taaaaatgat cttacacgtg aagaaattgt ggaattgatg    300
cgtgatgttt ctaaagaaga tcacagcaaa aggagcagtt ttgtttgtgt gcttctgagc    360
catggtgaag aaggaataat ttttggaaca aatggacctg ttgacctgaa aaaataaca    420
aacttttca gaggggatcg ttgtagaagt ctaactggaa aacccaaact tttcattatt    480
caggcctgcc gtggtacaga actggactgt ggcattgaga cagacagtgg tgttgatgat    540
gacatggcgt gtcataaaat accagtggat gccgacttct tgtatgcata ctccacagca    600
cctggttatt attcttggcg aaattcaaag gatggctcct ggttcatcca gtcgctttgt    660
gccatgctga aacagtatgc cgacaagctt gaatttatgc acattcttac ccgggttaac    720
cgaaaggtgg caacagaatt tgagtccttt tcctttgacg ctacttttca tgcaaagaaa    780
cagattccat gtattgtttc catgctcaca aagaactct atttttatca ctaan          835

<210> SEQ ID NO 11
<211> LENGTH: 835
<212> TYPE: DNA
<213> ORGANISM: Homo sapien
```

```
<220> FEATURE:
<221> NAME/KEY: misc_feature
<222> LOCATION: (1)...(835)
<223> OTHER INFORMATION: n = A,T,C or G

<400> SEQUENCE: 11
tacctcttgt gacttttgag tcacctaagt tttaggtaat ttttaaacct tggtttctag    60
tatgtacctt cgcttagtta cctgagacct tatagggacc tgttgtcaat attttaccta   120
ataggactct acccaaatac atattattaa ttattattct taaaagtatt ttcgtgacct   180
tactgtagag ccagaccatg tctacagcta cgtcgtttgg agtccctttg taagtctttg   240
aactttatac ttcagtcctt attttttacta gaatgtgcac ttctttaaca ccttaactac   300
gcactacaaa gatttcttct agtgtcgttt tcctcgtcaa aacaaacaca cgaagactcg   360
gtaccacttc ttccttatta aaaaccttgt ttacctggac aactggactt tttttattgt   420
ttgaaaaagt ctccctagc aacatcttca gattgacctt tgggtttga aaagtaataa    480
gtccggacgg caccatgtct tgacctgaca ccgtaactct gtctgtcacc acaactacta   540
ctgtaccgca cagtatttta tggtcaccta cggctgaaga acatacgtat gaggtgtcgt   600
ggaccaataa taagaaccgc tttaagtttc ctaccgagga ccaagtaggt cagcgaaaca   660
cggtacgact ttgtcatacg gctgttcgaa cttaaatacg tgtaagaatg ggcccaattg   720
gctttccacc gttgtcttaa actcaggaaa aggaaactgc gatgaaaagt acgtttcttt   780
gtctaaggta cataacaaag gtacgagtgt tttcttgaga taaaaatagt gattn        835

<210> SEQ ID NO 12
<211> LENGTH: 277
<212> TYPE: PRT
<213> ORGANISM: Homo sapien

<400> SEQUENCE: 12

Met Glu Asn Thr Glu Asn Ser Val Asp Ser Lys Ser Ile Lys Asn Leu
  1               5                  10                  15

Glu Pro Lys Ile Ile His Gly Ser Glu Ser Met Asp Ser Gly Ile Ser
             20                  25                  30

Leu Asp Asn Ser Tyr Lys Met Asp Tyr Pro Glu Met Gly Leu Cys Ile
         35                  40                  45

Ile Ile Asn Asn Lys Asn Phe His Lys Ser Thr Gly Met Thr Ser Arg
     50                  55                  60

Ser Gly Thr Asp Val Asp Ala Ala Asn Leu Arg Glu Thr Phe Arg Asn
 65                  70                  75                  80

Leu Lys Tyr Glu Val Arg Asn Lys Asn Asp Leu Thr Arg Glu Glu Ile
                 85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Asp Ala Asp
            180                 185                 190
```

```
Phe Leu Tyr Ala Tyr Ser Thr Ala Pro Gly Tyr Tyr Ser Trp Arg Asn
            195                 200                 205

Ser Lys Asp Gly Ser Trp Phe Ile Gln Ser Leu Cys Ala Met Leu Lys
        210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 13
<211> LENGTH: 1134
<212> TYPE: DNA
<213> ORGANISM: Homo sapien

<400> SEQUENCE: 13
atggcagaag gcaaccacag aaaaaagcca cttaaggtgt tggaatccct gggcaaagat      60
ttcctcactg gtgttttgga taacttggtg aacaaaatg tactgaactg aaggaagag     120 gaaaaaaaga atattacga tgctaaaact gaagacaaag ttcgggtcat ggcagactct    180
atgcaagaga agcaacgtat ggcaggacaa atgcttcttc aaacctttt taacatagac     240 caaatatccc ccaataaaaa agctcatccg aatatggagc tggaccacc tgagtcagga    300 gaatctacag atgccctcaa gctttgtcct catgaagaat tcctgagact atgtaaagaa    360
agagctgaag agatctatcc aataaaggag agaaacaacc gcacacgcct ggctctcatc    420
atatgcaata cagagtttga ccatctgcct ccgaggaatg gagctgactt tgacatcaca    480
gggatgaagg agctacttga gggtctggac tatagtgtag atgtagaaga gaatctgaca    540
gccagggata tggagtcagc gctgagggca tttgctacca gccagagca aagtcctct     600 gacagcacat tcttggtact catgtctcat ggcatcctgg agggaatctg cggaactgtg    660
catgatgaga aaaaaccaga tgtgctgctt tatgacacca tcttccagat attcaacaac    720
cgcaactgcc tcagtctgaa ggacaaaccc aaggtcatca ttgtccaggc ctgcagaggt    780
gcaaaccgtg gggaactgtg ggtcagagac tctccagcat ccttggaagt ggcctcttca    840
cagtcatctg agaacctgga ggaagatgct gtttacaaga cccacgtgga agaggacttc    900
attgctttct gctcttcaac gccacacaac gtgtcctgga gagacagcac aatgggctct    960
atcttcatca cacaactcat cacatgcttc cagaaatatt cttggtgctg ccacctagag   1020
gaagtatttc ggaaggtaca gcaatcattt gaaactccaa gggccaaagc tcaaatgccc   1080
accatagaac gactgtccat gacaagatat ttctacctct ttcctggcaa ttga         1134

<210> SEQ ID NO 14
<211> LENGTH: 1134
<212> TYPE: DNA
<213> ORGANISM: Homo sapien

<400> SEQUENCE: 14
taccgtcttc cgttggtgtc tttttcggt gaattccaca accttaggga cccgtttcta       60
aaggagtgac cacaaaacct attgaaccac cttgttttac atgacttgac cttccttctc    120 cttttttct ttataatgct acgattttga cttctgtttc aagcccagta ccgtctgaga    180
tacgttctct tcgttgcata ccgtcctgtt tacgaagaag tttggaaaaa attgtatctg    240
```

-continued

```
gtttataggg ggttattttt tcgagtaggc ttatacctcc gacctggtgg actcagtcct    300
cttagatgtc tacgggagtt cgaaacagga gtacttctta aggactctga tacatttctt    360
tctcgacttc tctagatagg ttatttcctc tctttgttgg cgtgtgcgga ccgagagtag    420
tatacgttat gtctcaaact ggtagacgga ggctccttac ctcgactgaa actgtagtgt    480
ccctacttcc tcgatgaact cccagacctg atatcacatc tacatcttct cttagactgt    540
cggtccctat acctcagtcg cgactcccgt aaacgatggt ctggtctcgt gttcaggaga    600
ctgtcgtgta agaaccatga gtacagagta ccgtaggacc tcccttagac gccttgacac    660
gtactactct tttttggtct acacgacgaa atactgtggt agaaggtcta taagttgttg    720
gcgttgacgg agtcagactt cctgtttggg ttccagtagt aacaggtccg dacgtctcca    780
cgtttggcac cccttgacac ccagtctctg agaggtcgta ggaaccttca ccggagaagt    840
gtcagtagac tcttggaccect ccttctacga caaatgttct gggtgcacct cttcctgaag    900
taacgaaaga cgagaagttg cggtgtgttg cacaggacct ctctgtcgtg ttacccgaga    960
tagaagtagt gtgttgagta gtgtacgaag gtctttataa gaaccacgac ggtggatctc   1020
cttcataaag ccttccatgt cgttagtaaa ctttgaggtt cccggtttcg agtttacggg   1080
tggtatcttg ctgacaggta ctgttctata aagatggaga aaggaccgtt aact         1134
```

<210> SEQ ID NO 15
<211> LENGTH: 377
<212> TYPE: PRT
<213> ORGANISM: Homo sapien

<400> SEQUENCE: 15

```
Met Ala Glu Gly Asn His Arg Lys Lys Pro Leu Lys Val Leu Glu Ser
 1               5                  10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
    130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
```

-continued

```
           210                 215                 220
Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
        275                 280                 285

Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
    370                 375
```

<210> SEQ ID NO 16
<211> LENGTH: 1258
<212> TYPE: DNA
<213> ORGANISM: Homo sapien
<220> FEATURE:
<221> NAME/KEY: misc_feature
<222> LOCATION: (1)...(1258)
<223> OTHER INFORMATION: n = A,T,C or G

<400> SEQUENCE: 16

```
atgttcaaag gtatccttca gagtggattg gataacttcg tgataaacca catgctaaag      60
aacaacgtgg ctggacaaac atctatccag accctagtac ctaatacgga tcaaaagtcg     120
accagtgtaa aaaagacaa ccacaaaaaa aaacagtta agatgttgga atacctgggc       180
aaagatgttc ttcatggtgt ttttaattat ttggcaaaac acgatgttct gacattgaag     240
gaagaggaaa agaaaaaata ttatgatgcc aaaattgaag acaaggccct gatcttggta     300
gactctttgc gaaagaatcg cgtggctcat caaatgttta cccaaacact tctcaatatg     360
gaccaaaaga tcaccagtgt aaaacctctt ctgcaaatcg aggctggacc acctgagtca     420
gcagaatcta caaatatact caactttgt cctcgtgaag aattcctgag actgtgtaaa      480
aaaaatcatg atgagatcta ccaataaaa aagagagagg accgcagacg cctggctctc      540
atcatatgca atacaaagtt tgatcacctg cctgcaagga tgggggctca ctatgacatc     600
gtggggatga aaaggctgct tcaaggcctg ggctacactg tggttgacga aaagaatctc     660
acagccaggg atatggagtc agtgctgagg gcatttgctg ccagaccaga gcacaagtcc     720
tctgacagca cgttcttggt actcatgtct catggcatcc tagagggaat ctgcggaact     780
gcgcataaaa agaaaaaacc ggatgtgctg ctttatgaca ccatcttcca gatattcaac     840
aaccgcaact gcctcagtct aaaggacaaa cccaaggtca tcattgtcca ggcctgcaga     900
ggtgaaaaac atgggggaact ctgggtcaga gactctccag catccttggc agtcatctct     960
tcacagtcat ctgagaacct ggaggcagat tctgtttgca agatccacga ggagaaggac    1020
ttcattgctt tctgttcttc aacaccacat aacgtgtcct ggagagaccg cacaagggc     1080
```

-continued

```
tccatcttca ttacggaact catcacatgc ttccagaaat attcttgctg ctgccaccta   1140 atgaaatat ttcggaaggt acagaaatca tttgaagttc cacaggctaa agcccagatg   1200
cccaccatag aacgagcaac cttgacaaga gatttctacc tctttcctgg caattgan   1258
```

<210> SEQ ID NO 17
<211> LENGTH: 1258
<212> TYPE: DNA
<213> ORGANISM: Homo sapien
<220> FEATURE:
<221> NAME/KEY: misc_feature
<222> LOCATION: (1)...(1258)
<223> OTHER INFORMATION: n = A,T,C or G

<400> SEQUENCE: 17

```
tacaagtttc cataggaagt ctcacctaac ctattgaagc actatttggt gtacgatttc     60
ttgttgcacc gacctgtttg tagataggtc tgggatcatg gattatgcct agttttcagc    120
tggtcacatt ttttctgtt ggtgttttt ttttgtcaat tctacaacct tatggacccg    180
tttctacaag aagtaccaca aaattaata aaccgttttg tgctacaaga ctgtaacttc    240
cttctccttt tctttttat aatactacgg ttttaacttc tgttccggga ctagaaccat    300
ctgagaaacg ctttcttagc gcaccgagta gtttacaaat gggtttgtga agagttatac    360
ctggttttct agtggtcaca ttttggagaa gacgtttagc tccgacctgg tggactcagt    420
cgtcttagat gtttatatga gtttgaaaca ggagcacttc ttaaggactc tgacacattt    480
tttttagtac tactctagat aggttatttt ttctctctcc tggcgtctgc ggaccgagag    540
tagtatacgt tatgtttcaa actagtggac ggacgttcct tacccgagt gatactgtag    600 caccctact tttccgacga agttccggac ccgatgtgac accaactgct tttcttagag    660
tgtcggtccc tatacctcag tcacgactcc cgtaaacgac ggtctggtct cgtgttcagg    720
agactgtcgt gcaagaacca tgagtacaga gtaccgtagg atctcccttta gacgccttga    780 cgcgtatttt tctttttgg cctacacgac gaaatactgt ggtagaaggt ctataagttg    840
ttggcgttga cggagtcaga tttcctgttt gggttccagt agtaacaggt ccggacgtct    900
ccactttttg tacccttga gacccagtct ctgagaggtc gtaggaaccg tcagtagaga    960
agtgtcagta gactcttgga cctccgtcta agacaaacgt tctaggtgct cctcttcctg   1020
aagtaacgaa agacaagaag ttgtggtgta ttgcacagga cctctctggc gtgttccccg   1080
aggtagaagt aatgccttga gtagtgtacg aaggtcttta taagaacgac gacggtggat   1140 taccttttata aagccttcca tgtctttagt aaacttcaag gtgtccgatt tcgggtctac   1200
gggtggtatc ttgctcgttg gaactgttct ctaaagatgg agaaaggacc gttaactn    1258
```

<210> SEQ ID NO 18
<211> LENGTH: 418
<212> TYPE: PRT
<213> ORGANISM: Homo sapien

<400> SEQUENCE: 18

```
Met Phe Lys Gly Ile Leu Gln Ser Gly Leu Asp Asn Phe Val Ile Asn
 1               5                  10                  15

His Met Leu Lys Asn Asn Val Ala Gly Gln Thr Ser Ile Gln Thr Leu
            20                  25                  30

Val Pro Asn Thr Asp Gln Lys Ser Thr Ser Val Lys Lys Asp Asn His
        35                  40                  45

Lys Lys Lys Thr Val Lys Met Leu Glu Tyr Leu Gly Lys Asp Val Leu
```

```
                50                      55                      60
His Gly Val Phe Asn Tyr Leu Ala Lys His Asp Val Leu Thr Leu Lys
 65                      70                      75                      80

Glu Glu Glu Lys Lys Tyr Tyr Asp Ala Lys Ile Glu Asp Lys Ala
                 85                      90                      95

Leu Ile Leu Val Asp Ser Leu Arg Lys Asn Arg Val Ala His Gln Met
                100                     105                     110

Phe Thr Gln Thr Leu Leu Asn Met Asp Gln Lys Ile Thr Ser Val Lys
                115                     120                     125

Pro Leu Leu Gln Ile Glu Ala Gly Pro Pro Glu Ser Ala Glu Ser Thr
130                     135                     140

Asn Ile Leu Lys Leu Cys Pro Arg Glu Glu Phe Leu Arg Leu Cys Lys
145                     150                     155                     160

Lys Asn His Asp Glu Ile Tyr Pro Ile Lys Lys Arg Glu Asp Arg Arg
                165                     170                     175

Arg Leu Ala Leu Ile Ile Cys Asn Thr Lys Phe Asp His Leu Pro Ala
                180                     185                     190

Arg Asn Gly Ala His Tyr Asp Ile Val Gly Met Lys Arg Leu Leu Gln
                195                     200                     205

Gly Leu Gly Tyr Thr Val Val Asp Glu Lys Asn Leu Thr Ala Arg Asp
210                     215                     220

Met Glu Ser Val Leu Arg Ala Phe Ala Ala Arg Pro Glu His Lys Ser
225                     230                     235                     240

Ser Asp Ser Thr Phe Leu Val Leu Met Ser His Gly Ile Leu Glu Gly
                245                     250                     255

Ile Cys Gly Thr Ala His Lys Lys Lys Lys Pro Asp Val Leu Leu Tyr
                260                     265                     270

Asp Thr Ile Phe Gln Ile Phe Asn Asn Arg Asn Cys Leu Ser Leu Lys
                275                     280                     285

Asp Lys Pro Lys Val Ile Ile Val Gln Ala Cys Arg Gly Glu Lys His
290                     295                     300

Gly Glu Leu Trp Val Arg Asp Ser Pro Ala Ser Leu Ala Val Ile Ser
305                     310                     315                     320

Ser Gln Ser Ser Glu Asn Leu Glu Ala Asp Ser Val Cys Lys Ile His
                325                     330                     335

Glu Glu Lys Asp Phe Ile Ala Phe Cys Ser Ser Thr Pro His Asn Val
                340                     345                     350

Ser Trp Arg Asp Arg Thr Arg Gly Ser Ile Phe Ile Thr Glu Leu Ile
                355                     360                     365

Thr Cys Phe Gln Lys Tyr Ser Cys Cys His Leu Met Glu Ile Phe
                370                     375                     380

Arg Lys Val Gln Lys Ser Phe Glu Val Pro Gln Ala Lys Ala Gln Met
385                     390                     395                     400

Pro Thr Ile Glu Arg Ala Thr Leu Thr Arg Asp Phe Tyr Leu Phe Pro
                405                     410                     415

Gly Asn

<210> SEQ ID NO 19
<211> LENGTH: 883
<212> TYPE: DNA
<213> ORGANISM: Homo sapien
<220> FEATURE:
<221> NAME/KEY: misc_feature
<222> LOCATION: (1)...(883)
<223> OTHER INFORMATION: n = A,T,C or G
```

<400> SEQUENCE: 19

```
atgagctcgg cctcggggct ccgcagggggg cacccggcag gtggggaaga aacatgaca    60
gaaacagatg ccttctataa agagaaatg tttgatccgg cagaaaagta caaaatggac    120
cacaggagga gaggaattgc tttaatcttc aatcatgaga ggttcttttg gcacttaaca    180
ctgccagaaa ggcggggcac ctgcgcagat agagacaatc ttacccgcag gttttcagat    240
ctaggatttg aagtgaaatg ctttaatgat cttaaagcag aagaactact gctcaaaatt    300
catgaggtgt caactgttag ccacgcagat gccgattgct ttgtgtgtgt cttcctgagc    360
catggcgaag gcaatcacat ttatgcatat gatgctaaaa tcgaaattca gacattaact    420
ggcttgttca aggagacaa gtgtcacagc ctggttggaa acccaagat atttatcatc    480
caggcatgtc ggggaaacca gcacgatgtg ccagtcattc ctttggatgt agtagataat    540
cagacagaga agttggacac caacataact gaggtggatg cagcctccgt ttacacgctg    600
cctgctggag ctgacttcct catgtgttac tctgttgcag aaggatatta ttctcaccgg    660
gaaactgtga acggctcatg gtacattcaa gatttgtgtg agatgttggg aaaatatggc    720
tcctccttag agttcacaga actcctcaca ctggtgaaca ggaaagtttc tcagcgccga    780
gtggactttt gcaaagaccc aagtgcaatt ggaaagaagc aggttccctg ttttgcctca    840
atgctaacta aaaagctgca tttctttcca aaatctaatt aan                     883
```

<210> SEQ ID NO 20
<211> LENGTH: 883
<212> TYPE: DNA
<213> ORGANISM: Homo sapien
<220> FEATURE:
<221> NAME/KEY: misc_feature
<222> LOCATION: (1)...(883)
<223> OTHER INFORMATION: n = A,T,C or G

<400> SEQUENCE: 20

```
tactcgagcc ggagccccga ggcgtccccc gtgggccgtc cacccttct tttgtactgt    60
ctttgtctac ggaagatatt ttctctttac aaactaggcc gtcttttcat gttttacctg    120
gtgtcctcct ctccttaacg aaattagaag ttagtactct ccaagaaaac cgtgaattgt    180
gacggtcttt ccgcccccgtg gacgcgtcta tctctgttag aatgggcgtc caaaagtcta    240
gatcctaaac ttcactttac gaaattacta gaatttcgtc ttcttgatga cgagttttaa    300
gtactccaca gttgacaatc ggtgcgtcta cggctaacga aacacacaca gaaggactcg    360
gtaccgcttc cgttagtgta aatacgtata ctacgatttt agctttaagt ctgtaattga    420
ccgaacaagt ttcctctgtt cacagtgtcg gaccaaccct ttgggttcta taaatagtag    480
gtccgtacag cccctttggt cgtgctacac ggtcagtaag gaaacctaca tcatctatta    540
gtctgtctct tcaacctgtg gttgtattga ctccacctac gtcggaggca aatgtgcgac    600
ggacgacctc gactgaagga gtacacaatg agacaacgtc ttcctataat aagagtggcc    660
ctttgacact tgccgagtac catgtaagtt ctaaacacac tctacaaccc ttttataccg    720
aggaggaatc tcaagtgtct tgaggagtgt gaccacttgt cctttcaaag agtcgcggct    780
cacctgaaaa cgtttctggg ttcacgttaa cctttcttcg tccaagggac aaaacggagt    840
tacgattgat ttttcgacgt aaagaaaggt tttagattaa ttn                     883
```

<210> SEQ ID NO 21
<211> LENGTH: 293
<212> TYPE: PRT

<213> ORGANISM: Homo sapien

<400> SEQUENCE: 21

Met Ser Ser Ala Ser Gly Leu Arg Arg Gly His Pro Ala Gly Gly Glu
1               5                   10                  15

Glu Asn Met Thr Glu Thr Asp Ala Phe Tyr Lys Arg Glu Met Phe Asp
            20                  25                  30

Pro Ala Glu Lys Tyr Lys Met Asp His Arg Arg Gly Ile Ala Leu
        35                  40                  45

Ile Phe Asn His Glu Arg Phe Phe Trp His Leu Thr Leu Pro Glu Arg
    50                  55                  60

Arg Gly Thr Cys Ala Asp Arg Asp Asn Leu Thr Arg Arg Phe Ser Asp
65              70                  75                  80

Leu Gly Phe Glu Val Lys Cys Phe Asn Asp Leu Lys Ala Glu Glu Leu
                85                  90                  95

Leu Leu Lys Ile His Glu Val Ser Thr Val Ser His Ala Asp Ala Asp
            100                 105                 110

Cys Phe Val Cys Val Phe Leu Ser His Gly Glu Gly Asn His Ile Tyr
        115                 120                 125

Ala Tyr Asp Ala Lys Ile Glu Ile Gln Thr Leu Thr Gly Leu Phe Lys
    130                 135                 140

Gly Asp Lys Cys His Ser Leu Val Gly Lys Pro Lys Ile Phe Ile Ile
145             150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225             230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290

<210> SEQ ID NO 22
<211> LENGTH: 913
<212> TYPE: DNA
<213> ORGANISM: Homo sapien
<220> FEATURE:
<221> NAME/KEY: misc_feature
<222> LOCATION: (1)...(913)
<223> OTHER INFORMATION: n = A,T,C or G

<400> SEQUENCE: 22
atggcagatg atcagggctg tattgaagag caggggttg aggattcagc aaatgaagat     60
tcagtggatg ctaagccaga ccggtcctcg tttgtaccgt ccctcttcag taagaagaag    120
aaaaatgtca ccatgcgatc catcaagacc acccgggacc gagtgcctac atatcagtac    180

-continued

```
aacatgaatt tgaaaagct gggcaaatgc atcataataa acaacaagaa ctttgataaa      240
gtgacaggta tgggcgttcg aaacggaaca gacaaagatg ccgaggcgct cttcaagtgc      300
ttccgaagcc tggttttga cgtgattgtc tataatgact gctcttgtgc caagatgcaa      360
gatctgctta aaaagcttc tgaagaggac catacaaatg ccgcctgctt cgcctgcatc      420
ctcttaagcc atgagaaga aaatgtaatt tatgggaaag atggtgtcac accaataaag      480
gatttgacag cccactttag ggggataga tgcaaaaccc ttttagagaa acccaaactc      540
ttcttcattc aggcttgccg agggaccgag cttgatgatg catccaggc cgactcgggg      600 cccatcaatg acacagatgc taatcctcga tacaagatcc cagtggaagc tgacttcctc      660
ttcgcctatt ccacggttcc aggctattac tcgtggagga gcccaggaag aggctcctgg      720
tttgtgcaag ccctctgctc catcctggag gagcacggaa aagacctgga aatcatgcag      780
atcctcacca gggtgaatga cagagttgcc aggcactttg agtctcagtc tgatgaccca      840
cacttccatg agaagaagca gatcccctgt gtggtctcca tgctcaccaa ggaactctac      900
ttcagtcaat agn                                                         913
```

<210> SEQ ID NO 23
<211> LENGTH: 913
<212> TYPE: DNA
<213> ORGANISM: Homo sapien
<220> FEATURE:
<221> NAME/KEY: misc_feature
<222> LOCATION: (1)...(913)
<223> OTHER INFORMATION: n = A,T,C or G

<400> SEQUENCE: 23

```
taccgtctac tagtcccgac ataacttctc gtcccccaac tcctaagtcg tttacttcta       60
agtcacctac gattcggtct ggccaggagc aaacatggca gggagaagtc attcttcttc      120
tttttacagt ggtacgctag gtagttctgg tgggccctgg ctcacggatg tatagtcatg      180
ttgtacttaa aacttttcga cccgtttacg tagtattatt tgttgttctt gaaactattt      240
cactgtccat acccgcaagc tttgccttgt ctgtttctac ggctccgcga gaagttcacg      300
aaggcttcgg acccaaaact gcactaacag atattactga cgagaacacg gttctacgtt      360
ctagacgaat ttttcgaag acttctcctg gtatgtttac ggcggacgaa gcggacgtag      420
gagaattcgg tacctcttct tttacattaa atacccttc taccacagtg tggttatttc      480
ctaaactgtc gggtgaaatc cccctatct acgttttggg aaaatctctt tgggtttgag      540
aagaagtaag tccgaacggc tccctggctc gaactactac cgtaggtccg gctgagcccc      600
gggtagttac tgtgtctacg attaggagct atgttctagg gtcaccttcg actgaaggag      660
aagcggataa ggtgccaagg tccgataatg agcacctcct cgggtccttc tccgaggacc      720
aaacacgttc gggagacgag gtaggacctc ctcgtgcctt ttctggacct ttagtacgtc      780
taggagtggt cccacttact gtctcaacgg tccgtgaaac tcagagtcag actactgggt      840
gtgaaggtac tcttcttcgt ctaggggaca caccagaggt acgagtggtt ccttgagatg      900
aagtcagtta tcn                                                         913
```

<210> SEQ ID NO 24
<211> LENGTH: 303
<212> TYPE: PRT
<213> ORGANISM: Homo sapien

<400> SEQUENCE: 24

Met Ala Asp Asp Gln Gly Cys Ile Glu Glu Gln Gly Val Glu Asp Ser

```
  1               5                    10                   15
Ala Asn Glu Asp Ser Val Asp Ala Lys Pro Asp Arg Ser Ser Phe Val
             20                  25                  30
Pro Ser Leu Phe Ser Lys Lys Lys Asn Val Thr Met Arg Ser Ile
         35                  40                  45
Lys Thr Thr Arg Asp Arg Val Pro Thr Tyr Gln Tyr Asn Met Asn Phe
 50                  55                  60
Glu Lys Leu Gly Lys Cys Ile Ile Asn Asn Lys Asn Phe Asp Lys
 65                  70                  75                  80
Val Thr Gly Met Gly Val Arg Asn Gly Thr Asp Lys Asp Ala Glu Ala
                 85                  90                  95
Leu Phe Lys Cys Phe Arg Ser Leu Gly Phe Asp Val Ile Val Tyr Asn
                 100                 105                 110
Asp Cys Ser Cys Ala Lys Met Gln Asp Leu Leu Lys Lys Ala Ser Glu
             115                 120                 125
Glu Asp His Thr Asn Ala Ala Cys Phe Ala Cys Ile Leu Leu Ser His
 130                 135                 140
Gly Glu Glu Asn Val Ile Tyr Gly Lys Asp Gly Val Thr Pro Ile Lys
 145                 150                 155                 160
Asp Leu Thr Ala His Phe Arg Gly Asp Arg Cys Lys Thr Leu Leu Glu
                 165                 170                 175
Lys Pro Lys Leu Phe Phe Ile Gln Ala Cys Arg Gly Thr Glu Leu Asp
             180                 185                 190
Asp Gly Ile Gln Ala Asp Ser Gly Pro Ile Asn Asp Thr Asp Ala Asn
             195                 200                 205
Pro Arg Tyr Lys Ile Pro Val Glu Ala Asp Phe Leu Phe Ala Tyr Ser
 210                 215                 220
Thr Val Pro Gly Tyr Tyr Ser Trp Arg Ser Pro Gly Arg Gly Ser Trp
 225                 230                 235                 240
Phe Val Gln Ala Leu Cys Ser Ile Leu Glu Glu His Gly Lys Asp Leu
             245                 250                 255
Glu Ile Met Gln Ile Leu Thr Arg Val Asn Asp Arg Val Ala Arg His
             260                 265                 270
Phe Glu Ser Gln Ser Asp Asp Pro His Phe His Glu Lys Lys Gln Ile
             275                 280                 285
Pro Cys Val Val Ser Met Leu Thr Lys Glu Leu Tyr Phe Ser Gln
 290                 295                 300

<210> SEQ ID NO 25
<211> LENGTH: 1493
<212> TYPE: DNA
<213> ORGANISM: Homo sapien
<220> FEATURE:
<221> NAME/KEY: misc_feature
<222> LOCATION: (1)...(1493)
<223> OTHER INFORMATION: n = A,T,C or G

<400> SEQUENCE: 25
atggacttca gcagaaatct ttatgatatt ggggaacaac tggacagtga agatctggcc      60
tccctcaagt tcctgagcct ggactacatt ccgcaaagga agcaagaacc catcaaggat     120
gccttgatgt tattccagag actccaggaa aagagaatgt tggaggaaag caatctgtcc     180
ttcctgaagg agctgctctt ccgaattaat agactggatt tgctgattac ctacctaaac     240
actagaaagg aggagatgga aagggaactt cagacaccag gcagggctca aatttctgcc     300
tacaggttcc acttctgccg catgagctgg gctgaagcaa acagccagtg ccagacacag     360
```

-continued

```
tctgtacctt tctggcggag ggtcgatcat ctattaataa gggtcatgct ctatcagatt      420
tcagaagaag tgagcagatc agaattgagg tcttttaagt ttcttttgca agaggaaatc      480
tccaaatgca aactggatga tgacatgaac ctgctggata ttttcataga gatggagaag      540
agggtcatcc tggagaagg  aaagttggac atcctgaaaa gagtctgtgc ccaaatcaac      600
aagagcctgc tgaagataat caacgactat gaagaattca gcaaagggga ggagttgtgt      660
ggggtaatga caatctcgga ctctccaaga gaacaggata gtgaatcaca gactttggac      720
aaagtttacc aaatgaaaag caaacctcgg ggatactgtc tgatcatcaa caatcacaat      780
tttgcaaaag cacgggagaa agtgcccaaa cttcacagca ttagggacag gaatggaaca      840
cacttggatg caggggcttt gaccacgacc tttgaagagc ttcattttga gatcaagccc      900
caccatgact gcacagtaga gcaaatctat gagattttga aaatctacca actcatggac      960
cacagtaaca tggactgctt catctgctgt atcctctccc atggagacaa gggcatcatc     1020
tatggcactg atgacagga ggcccccatc tatgagctga catctcagtt cactggtttg      1080
aagtgccctt cccttgctgg aaaacccaaa gtgtttttta ttcaggcttg tcagggggat     1140
aactaccaga aaggtatacc tgttgagact gattcagagg agcaaccccta tttagaaatg     1200 gatttatcat cacctcaaac gagatatatc ccggatgagg ctgactttct gctggggatg     1260
gccactgtga ataactgtgt ttcctaccga aaccctgcag agggaacctg gtacatccag     1320
tcactttgcc agagcctgag agagcgatgt cctcgaggcg atgatattct caccatcctg     1380
actgaagtga actatgaagt aagcaacaag gatgacaaga aaaacatggg gaaacagatg     1440
cctcagccta ctttcacact aagaaaaaaa cttgtcttcc cttctgattg ann            1493
```

<210> SEQ ID NO 26
<211> LENGTH: 1493
<212> TYPE: DNA
<213> ORGANISM: Homo sapien
<220> FEATURE:
<221> NAME/KEY: misc_feature
<222> LOCATION: (1)...(1493)
<223> OTHER INFORMATION: n = A,T,C or G

<400> SEQUENCE: 26

```
tacctgaagt cgtctttaga aatactataa ccccttgttg acctgtcact tctagaccgg       60
agggagttca aggactcgga cctgatgtaa ggcgtttcct tcgttcttgg gtagttccta      120
cggaactaca ataaggtctc tgaggtcctt ttctcttaca acctcctttc gttagacagg      180
aaggacttcc tcgacgagaa ggcttaatta tctgacctaa acgactaatg gatgatttg       240 tgatctttcc tcctctacct ttcccttgaa gtctgtggtc cgtcccgagt ttaaagacgg      300
atgtccaagg tgaagacggc gtactcgacc cgacttcgtt tgtcggtcac ggtctgtgtc      360
agacatggaa agaccgcctc ccagctagta gataattatt cccagtacga gatagtctaa      420
agtcttcttc actcgtctag tcttaactcc agaaaattca agaaaacgt tctccttag       480 aggtttacgt tgacctact actgtacttg gacgacctat aaaagtatct ctacctcttc      540
tcccagtagg accctcttcc tttcaacctg taggacttt ctcagacacg ggtttagttg       600
ttctcggacg acttctatta gttgctgata cttcttaagt cgtttcccct cctcaacaca      660
ccccattact gttagagcct gagaggttct cttgtcctat cacttagtgt ctgaaacctg      720
tttcaaatgg tttacttttc gtttggagcc cctatgacag actagtagtt gttagtgtta      780
aaacgttttc gtgccctctt tcacgggttt gaagtgtcgt aatccctgtc cttaccttgt      840
```

-continued

```
gtgaacctac gtccccgaaa ctggtgctgg aaacttctcg aagtaaaact ctagttcggg      900
gtggtactga cgtgtcatct cgtttagata ctctaaaact tttagatggt tgagtacctg      960
gtgtcattgt acctgacgaa gtagacgaca taggagaggg tacctctgtt cccgtagtag     1020
ataccgtgac tacctgtcct ccgggggtag atactcgact gtagagtcaa gtgaccaaac     1080
ttcacgggaa gggaacgacc ttttgggttt cacaaaaaat aagtccgaac agtccccta      1140 ttgatggtct ttccatatgg acaactctga ctaagtctcc tcgttgggat aaatctttac     1200
ctaaatagta gtggagtttg ctctatatag ggcctactcc gactgaaaga cgaccccta      1260 cggtgacact tattgacaca aaggatggct ttgggacgtc tcccttggac catgtaggtc     1320
agtgaaacgg tctcggactc tctcgctaca ggagctccgc tactataaga gtggtaggac     1380
tgacttcact tgatacttca ttcgttgttc ctactgttct ttttgtaccc ctttgtctac     1440
ggagtcggat gaaagtgtga ttcttttttt gaacagaagg gaagactaac tnn             1493
```

<210> SEQ ID NO 27
<211> LENGTH: 476
<212> TYPE: PRT
<213> ORGANISM: Homo sapien

<400> SEQUENCE: 27

```
Met Asp Phe Ser Arg Asn Leu Tyr Asp Ile Gly Glu Gln Leu Asp Ser
 1               5                  10                  15

Glu Asp Leu Ala Ser Leu Lys Phe Leu Ser Leu Asp Tyr Ile Pro Gln
             20                  25                  30

Arg Lys Gln Glu Pro Ile Lys Asp Ala Leu Met Leu Phe Gln Arg Leu
         35                  40                  45

Gln Glu Lys Arg Met Leu Glu Glu Ser Asn Leu Ser Phe Leu Lys Glu
     50                  55                  60

Leu Leu Phe Arg Ile Asn Arg Leu Asp Leu Leu Ile Thr Tyr Leu Asn
 65                  70                  75                  80

Thr Arg Lys Glu Glu Met Glu Arg Glu Leu Gln Thr Pro Gly Arg Ala
                 85                  90                  95

Gln Ile Ser Ala Tyr Arg Phe His Phe Cys Arg Met Ser Trp Ala Glu
            100                 105                 110

Ala Asn Ser Gln Cys Gln Thr Gln Ser Val Pro Phe Trp Arg Arg Val
        115                 120                 125

Asp His Leu Leu Ile Arg Val Met Leu Tyr Gln Ile Ser Glu Glu Val
    130                 135                 140

Ser Arg Ser Glu Leu Arg Ser Phe Lys Phe Leu Leu Gln Glu Glu Ile
145                 150                 155                 160

Ser Lys Cys Lys Leu Asp Asp Met Asn Leu Leu Asp Ile Phe Ile
                165                 170                 175

Glu Met Glu Lys Arg Val Ile Leu Gly Glu Gly Lys Leu Asp Ile Leu
            180                 185                 190

Lys Arg Val Cys Ala Gln Ile Asn Lys Ser Leu Leu Lys Ile Asn
        195                 200                 205

Asp Tyr Glu Glu Phe Ser Lys Gly Glu Glu Leu Cys Lys Val Tyr Gln
    210                 215                 220

Met Lys Ser Lys Pro Arg Gly Tyr Cys Leu Ile Ile Asn Asn His Asn
225                 230                 235                 240

Phe Ala Lys Ala Arg Glu Lys Val Pro Lys Leu His Ser Ile Arg Asp
                245                 250                 255

Arg Asn Gly Thr His Leu Asp Ala Gly Ala Leu Thr Thr Thr Phe Glu
```

-continued

```
                    260                 265                 270
Glu Leu His Phe Glu Ile Lys Pro His His Asp Cys Thr Val Glu Gln
            275                 280                 285
Ile Tyr Glu Ile Leu Lys Ile Tyr Gln Leu Met Asp His Ser Asn Met
        290                 295                 300
Asp Cys Phe Ile Cys Cys Ile Leu Ser His Gly Asp Lys Gly Ile Ile
305                 310                 315                 320
Tyr Gly Thr Asp Gly Gln Glu Ala Pro Ile Tyr Glu Leu Thr Ser Gln
                325                 330                 335
Phe Thr Gly Leu Lys Cys Pro Ser Leu Ala Gly Lys Pro Lys Val Phe
            340                 345                 350
Phe Ile Gln Ala Cys Gln Gly Asp Asn Tyr Gln Lys Gly Ile Pro Val
        355                 360                 365
Glu Thr Asp Ser Glu Glu Gln Pro Tyr Leu Glu Met Asp Leu Ser Ser
    370                 375                 380
Pro Gln Thr Arg Tyr Ile Pro Asp Glu Ala Asp Phe Leu Leu Gly Met
385                 390                 395                 400
Ala Thr Val Asn Asn Cys Val Ser Tyr Arg Asn Pro Ala Glu Gly Thr
                405                 410                 415
Trp Tyr Ile Gln Ser Leu Cys Gln Ser Leu Arg Glu Arg Cys Pro Arg
            420                 425                 430
Gly Asp Asp Ile Leu Thr Ile Leu Thr Glu Val Asn Tyr Glu Val Ser
        435                 440                 445
Asn Lys Asp Asp Lys Lys Asn Met Gly Lys Gln Met Pro Gln Pro Thr
    450                 455                 460
Phe Thr Leu Arg Lys Lys Leu Val Phe Pro Ser Asp
465                 470                 475
```

<210> SEQ ID NO 28
<211> LENGTH: 1252
<212> TYPE: DNA
<213> ORGANISM: Homo sapien
<220> FEATURE:
<221> NAME/KEY: misc_feature
<222> LOCATION: (1)...(1252)
<223> OTHER INFORMATION: n = A,T,C or G

<400> SEQUENCE: 28

```
atggacgaag cggatcggcg gctcctgcgg cggtgccggc tgcggctggt ggaagagctg      60
caggtggacc agctctggga cgccctgctg agcagcgagc tgttcaggcc ccatatgatc     120
gaggacatcc agcgggcagg ctctggatct cggcgggatc aggccaggca gctgatcata     180
gatctggaga ctcgagggag tcaggctctt cctttgttca tctcctgctt agaggacaca     240
ggccaggaca tgctggcttc gtttctgcga actaacaggc aagcagcaaa gttgtcgaag     300
ccaaccctag aaaaccttac cccagtggtg ctcagaccag agattcgcaa accagaggtt     360
ctcagaccgg aaacacccag accagtggac attggttctg gaggatttgg tgatgtcggt     420
gctcttgaga gtttgagggg aaatgcagat ttggcttaca tcctgagcat ggagccctgt     480
ggccactgcc tcattatcaa caatgtgaac ttctgccgtg agtccgggct ccgcacccgc     540
actggctcca acatcgactg tgagaagttg cggcgtcgct ctcctcgcc  gcatttcatg     600
gtggaggtga agggcgacct gactgccaag aaaatggtgc tggctttgct ggagctggcg     660
cggcaggacc acgtgctct  ggactgctgc gtggtggtca ttctctctca cggctgtcag     720
gccagccacc tgcagttccc aggggctgtc tacggcacag atggatgccc tgtgtcggtc     780
```

-continued

```
gagaagattg tgaacatctt caatgggacc agctgcccca gcctgggagg aaagcccaag    840
ctcttttcca tccaggcctg tggtggggag cagaaagacc atgggtttga ggtggcctcc    900
acttcccctg aagacgagtc ccctggcagt aaccccgagc cagatgccac cccgttccag    960
gaaggtttga ggaccttcga ccagctggac gccatatcta gtttgccac acccagtgac    1020 atctttgtgt cctactctac tttcccaggt tttgtttcct ggagggaccc caagagtggc    1080
tcctggtacg ttgagaccct ggacgacatc tttgagcagt gggctcactc tgaagacctg    1140
cagtccctcc tgcttagggt cgctaatgct gtttcggtga agggattta taaacagatg    1200 cctggttgct ttaatttcct ccggaaaaaa cttttcttta aaacatcata an            1252
```

<210> SEQ ID NO 29
<211> LENGTH: 1252
<212> TYPE: DNA
<213> ORGANISM: Homo sapien
<220> FEATURE:
<221> NAME/KEY: misc_feature
<222> LOCATION: (1)...(1252)
<223> OTHER INFORMATION: n = A,T,C or G

<400> SEQUENCE: 29

```
tacctgcttc gcctagccgc cgaggacgcc gccacggccg acgccgacca ccttctcgac    60
gtccacctgg tcgagaccct gcgggacgac tcgtcgctcg acaagtccgg ggtatactag    120
ctcctgtagg tcgcccgtcc gagacctaga gccgccctag tccggtccgt cgactagtat    180
ctagacctct gagctccctc agtccgagaa ggaaacaagt agaggacgaa tctcctgtgt    240
ccggtcctgt acgaccgaag caaagacgct tgattgtccg ttcgtcgttt caacagcttc    300
ggttgggatc ttttggaatg gggtcaccac gagtctggtc tctaagcgtt tggtctccaa    360
gagtctggcc tttgtgggtc tggtcacctg taaccaagac ctcctaaacc actacagcca    420
cgagaactct caaactcccc tttacgtcta aaccgaatgt aggactcgta cctcgggaca    480
ccggtgacgg agtaatagtt gttacacttg aagacggcac tcaggcccga ggcgtgggcg    540
tgaccgaggt tgtagctgac actcttcaac gccgcagcga agaggagcgg cgtaaagtac    600
cacctccact tcccgctgga ctgacggttc ttttaccacg accgaaacga cctcgaccgc    660
gccgtcctgg tgccacgaga cctgacgacg caccaccagt aagagagagt gccgacagtc    720
cggtcggtgg acgtcaaggg tccccgacag atgccgtgtc tacctacggg acacagccag    780
ctcttctaac acttgtagaa gttacccctgg tcgacgggt cggaccctcc tttcgggttc    840
gagaaaaagt aggtccggac accacccctc gtctttctgg tacccaaact ccaccggagg    900 tgaagggggac ttctgctcag gggaccgtca ttggggctcg gtctacggtg gggcaaggtc    960
cttccaaact cctggaagct ggtcgacctg cggtatagat caaacgggtg tgggtcactg    1020
tagaaacaca ggatgagatg aaagggtcca aacaaaagga cctccctggg gttctcaccg    1080
aggaccatgc aactctggga cctgctgtag aaactcgtca cccgagtgag acttctggac    1140
gtcagggagg acgaatccca gcgattacga caaagccact ttccctaaat atttgtctac    1200
ggaccaacga aattaaagga ggcctttttt gaaaagaaat tttgtagtat tn             1252
```

<210> SEQ ID NO 30
<211> LENGTH: 416
<212> TYPE: PRT
<213> ORGANISM: Homo sapien

<400> SEQUENCE: 30

Met Asp Glu Ala Asp Arg Arg Leu Leu Arg Arg Cys Arg Leu Arg Leu

```
      1               5                    10                   15
  Val Glu Glu Leu Gln Val Asp Gln Leu Trp Asp Ala Leu Leu Ser Ser
                   20                  25                  30

Glu Leu Phe Arg Pro His Met Ile Glu Asp Ile Gln Arg Ala Gly Ser
               35                  40                  45

Gly Ser Arg Arg Asp Gln Ala Arg Gln Leu Ile Ile Asp Leu Glu Thr
  50                  55                  60

Arg Gly Ser Gln Ala Leu Pro Leu Phe Ile Ser Cys Leu Glu Asp Thr
  65                  70                  75                  80

Gly Gln Asp Met Leu Ala Ser Phe Leu Arg Thr Asn Arg Gln Ala Ala
                   85                  90                  95

Lys Leu Ser Lys Pro Thr Leu Glu Asn Leu Thr Pro Val Val Leu Arg
                  100                 105                 110

Pro Glu Ile Arg Lys Pro Glu Val Leu Arg Pro Glu Thr Pro Arg Pro
                  115                 120                 125

Val Asp Ile Gly Ser Gly Gly Phe Gly Asp Val Gly Ala Leu Glu Ser
                  130                 135                 140

Leu Arg Gly Asn Ala Asp Leu Ala Tyr Ile Leu Ser Met Glu Pro Cys
  145                 150                 155                 160

Gly His Cys Leu Ile Ile Asn Asn Val Asn Phe Cys Arg Glu Ser Gly
                  165                 170                 175

Leu Arg Thr Arg Thr Gly Ser Asn Ile Asp Cys Glu Lys Leu Arg Arg
                  180                 185                 190

Arg Phe Ser Ser Pro His Phe Met Val Glu Val Lys Gly Asp Leu Thr
                  195                 200                 205

Ala Lys Lys Met Val Leu Ala Leu Leu Glu Leu Ala Arg Gln Asp His
                  210                 215                 220

Gly Ala Leu Asp Cys Cys Val Val Val Ile Leu Ser His Gly Cys Gln
  225                 230                 235                 240

Ala Ser His Leu Gln Phe Pro Gly Ala Val Tyr Gly Thr Asp Gly Cys
                  245                 250                 255

Pro Val Ser Val Glu Lys Ile Val Asn Ile Phe Asn Gly Thr Ser Cys
                  260                 265                 270

Pro Ser Leu Gly Gly Lys Pro Lys Leu Phe Phe Ile Gln Ala Cys Gly
                  275                 280                 285

Gly Glu Gln Lys Asp His Gly Phe Glu Val Ala Ser Thr Ser Pro Glu
  290                 295                 300

Asp Glu Ser Pro Gly Ser Asn Pro Glu Pro Asp Ala Thr Pro Phe Gln
  305                 310                 315                 320

Glu Gly Leu Arg Thr Phe Asp Gln Leu Asp Ala Ile Ser Ser Leu Pro
                  325                 330                 335

Thr Pro Ser Asp Ile Phe Val Ser Tyr Ser Thr Phe Pro Gly Phe Val
                  340                 345                 350

Ser Trp Arg Asp Pro Lys Ser Gly Ser Trp Tyr Val Glu Thr Leu Asp
                  355                 360                 365

Asp Ile Phe Glu Gln Trp Ala His Ser Glu Asp Leu Gln Ser Leu Leu
                  370                 375                 380

Leu Arg Val Ala Asn Ala Val Ser Val Lys Gly Ile Tyr Lys Gln Met
  385                 390                 395                 400

Pro Gly Cys Phe Asn Phe Leu Arg Lys Lys Leu Phe Phe Lys Thr Ser
                  405                 410                 415
```

<210> SEQ ID NO 31

<211> LENGTH: 1440
<212> TYPE: DNA
<213> ORGANISM: Homo sapien

<400> SEQUENCE: 31

| | | | | | |
|---|---|---|---|---|---|
| atgaaatctc | aaggtcaaca | ttggtattcc | agttcagata | aaaactgtaa | agtgagcttt | 60 |
| cgtgagaagc | ttctgattat | tgattcaaac | ctggggtcc | aagatgtgga | gaacctcaag | 120 |
| tttctctgca | taggattggt | ccccaacaag | aagctggaga | agtccagctc | agcctcagat | 180 |
| gttttgaac | atctccttggc | agaggatctg | ctgagtgagg | aagaccctt | cttcctggca | 240 |
| gaactcctct | atatcatacg | gcagaagaag | ctgctgcagc | acctcaactg | taccaaagag | 300 |
| gaagtggagc | gactgctgcc | cacccgacaa | agggtttctc | tgtttagaaa | cctgctctac | 360 |
| gaactgtcag | aaggcattga | ctcagagaac | ttaaaggaca | tgatcttcct | tctgaaagac | 420 |
| tcgcttccca | aaactgaaat | gacctcccta | agtttcctgg | catttctaga | gaaacaaggt | 480 |
| aaaatagatg | aagataatct | gacatgcctg | gaggacctct | gcaaaacagt | tgtacctaaa | 540 |
| cttttgagaa | acatagagaa | atacaaaaga | gagaaagcta | tccagatagt | gacacctcct | 600 |
| gtagacaagg | aagccgagtc | gtatcaagga | gaggaagaac | tagtttccca | aacagatgtt | 660 |
| aagacattct | tggaagcctt | accgagggca | gctgtgtaca | ggatgaatcg | gaaccacaga | 720 |
| ggcctctgtg | tcattgtcaa | caaccacagc | tttacctccc | tgaaggacag | acaaggaacc | 780 |
| cataaagatg | ctgagatcct | gagtcatgtg | ttccagtggc | ttgggttcac | agtgcatata | 840 |
| cacaataatg | tgacgaaagt | ggaaatggag | atggtcctgc | agaagcagaa | gtgcaatcca | 900 |
| gcccatgccg | acgggactg | cttcgtgttc | tgtattctga | cccatgggag | atttggagct | 960 |
| gtctactctt | cggatgaggc | cctcattccc | attcggaga | tcatgtctca | cttcacagcc | 1020 |
| ctgcagtgcc | ctagactggc | tgaaaaacct | aaactctttt | tcatccaggc | ctgccaaggt | 1080 |
| gaagagatac | agccttccgt | atccatcgaa | gcagatgctc | tgaaccctga | gcaggcaccc | 1140 |
| acttccctgc | aggacagtat | tcctgccgag | gctgacttcc | tacttggtct | ggccactgtc | 1200 |
| ccaggctatg | tatcctttcg | gcatgtggag | gaaggcagct | ggtatattca | gtctctgtgt | 1260 |
| aatcatctga | gaaattggt | cccaagacat | gaagacatct | tatccatcct | cactgctgtc | 1320 |
| aacgatgatg | tgagtcgaag | agtggacaaa | cagggaacaa | agaaacagat | gccccagcct | 1380 |
| gctttcacac | taaggaaaaa | actagtattc | cctgtgcccc | tggatgcact | ttcaatatag | 1440 |

<210> SEQ ID NO 32
<211> LENGTH: 1440
<212> TYPE: DNA
<213> ORGANISM: Homo sapien

<400> SEQUENCE: 32

| | | | | | |
|---|---|---|---|---|---|
| tactttagag | ttccagttgt | aaccataagg | tcaagtctat | ttttgacatt | tcactcgaaa | 60 |
| gcactcttcg | aagactaata | actaagtttg | gaccccagg | ttctacacct | cttggagttc | 120 |
| aaagagacgt | atcctaacca | ggggttgttc | ttcgacctct | tcaggtcgag | tcggagtcta | 180 |
| caaaaacttg | tagagaaccg | tctcctagac | gactcactcc | ttctgggaaa | gaaggaccgt | 240 |
| cttgaggaga | tatagtatgc | cgtcttcttc | gacgacgtcg | tggagttgac | atggtttctc | 300 |
| cttcacctcg | ctgacgacgg | gtgggctgtt | tcccaaagag | acaaatcttt | ggacgagatg | 360 |
| cttgacagtc | ttccgtaact | gagtctcttg | aatttcctgt | actagaagga | agactttctg | 420 |
| agcgaagggt | tttgacttta | ctggagggat | tcaaggacc | gtaaagatct | ctttgttcca | 480 |
| ttttatctac | ttctattaga | ctgtacggac | ctcctggaga | cgttttgtca | acatggattt | 540 |

-continued

```
gaaaactctt tgtatctctt tatgttttct ctctttcgat aggtctatca ctgtggagga   600
catctgttcc ttcggctcag catagttcct ctccttcttg atcaaagggt ttgtctacaa   660
ttctgtaaga accttcggaa tggctcccgt cgacacatgt cctacttagc cttggtgtct   720
ccggagacac agtaacagtt gttggtgtcg aaatggaggg acttcctgtc tgttccttgg   780
gtatttctac gactctagga ctcagtacac aaggtcaccg aacccaagtg tcacgtatat   840
gtgttattac actgctttca cctttacctc taccaggacg tcttcgtctt cacgttaggt   900
cgggtacggc tgcccctgac gaagcacaag acataagact gggtaccctc taaacctcga   960
cagatgagaa gcctactccg ggagtaaggg taagccctct agtacagagt gaagtgtcgg   1020
gacgtcacgg gatctgaccg acttttggaa tttgagaaaa agtaggtccg gacggttcca   1080
cttctctatg tcggaaggca taggtagctt cgtctacgag acttgggact cgtccgtggg   1140
tgaagggacg tcctgtcata aggacggctc cgactgaagg atgaaccaga ccggtgacag   1200
ggtccgatac ataggaaagc cgtacacctc cttccgtcga ccatataagt cagagacaca   1260
ttagtagact tctttaacca gggttctgta cttctgtaga ataggtagga gtgacgacag   1320
ttgctactac actcagcttc tcacctgttt gtcccttgtt tctttgtcta cggggtcgga   1380
cgaaagtgtg attcctttt tgatcataag ggacacgggg acctacgtga aagttatatc   1440
```

<210> SEQ ID NO 33
<211> LENGTH: 479
<212> TYPE: PRT
<213> ORGANISM: Homo sapien

<400> SEQUENCE: 33

```
Met Lys Ser Gln Gly Gln His Trp Tyr Ser Ser Asp Lys Asn Cys
 1               5                  10                  15

Lys Val Ser Phe Arg Glu Lys Leu Leu Ile Ile Asp Ser Asn Leu Gly
                20                  25                  30

Val Gln Asp Val Glu Asn Leu Lys Phe Leu Cys Ile Gly Leu Val Pro
            35                  40                  45

Asn Lys Lys Leu Glu Lys Ser Ser Ala Ser Asp Val Phe Glu His
        50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
```

-continued

```
            210                 215                 220
Glu Ala Leu Pro Arg Ala Ala Val Tyr Arg Met Asn Arg Asn His Arg
225                 230                 235                 240

Gly Leu Cys Val Ile Val Asn Asn His Ser Phe Thr Ser Leu Lys Asp
                245                 250                 255

Arg Gln Gly Thr His Lys Asp Ala Glu Ile Leu Ser His Val Phe Gln
            260                 265                 270

Trp Leu Gly Phe Thr Val His Ile His Asn Asn Val Thr Lys Val Glu
        275                 280                 285

Met Glu Met Val Leu Gln Lys Gln Lys Cys Asn Pro Ala His Ala Asp
    290                 295                 300

Gly Asp Cys Phe Val Phe Cys Ile Leu Thr His Gly Arg Phe Gly Ala
305                 310                 315                 320

Val Tyr Ser Ser Asp Glu Ala Leu Ile Pro Ile Arg Glu Ile Met Ser
                325                 330                 335

His Phe Thr Ala Leu Gln Cys Pro Arg Leu Ala Glu Lys Pro Lys Leu
            340                 345                 350

Phe Phe Ile Gln Ala Cys Gln Gly Glu Glu Ile Gln Pro Ser Val Ser
        355                 360                 365

Ile Glu Ala Asp Ala Leu Asn Pro Glu Gln Ala Pro Thr Ser Leu Gln
    370                 375                 380

Asp Ser Ile Pro Ala Glu Ala Asp Phe Leu Leu Gly Leu Ala Thr Val
385                 390                 395                 400

Pro Gly Tyr Val Ser Phe Arg His Val Glu Glu Gly Ser Trp Tyr Ile
                405                 410                 415

Gln Ser Leu Cys Asn His Leu Lys Lys Leu Val Pro Arg His Glu Asp
            420                 425                 430

Ile Leu Ser Ile Leu Thr Ala Val Asn Asp Asp Val Ser Arg Arg Val
        435                 440                 445

Asp Lys Gln Gly Thr Lys Lys Gln Met Pro Gln Pro Ala Phe Thr Leu
    450                 455                 460

Arg Lys Lys Leu Val Phe Pro Val Pro Leu Asp Ala Leu Ser Ile
465                 470                 475
```

<210> SEQ ID NO 34
<211> LENGTH: 290
<212> TYPE: PRT
<213> ORGANISM: Artificial Sequence
<220> FEATURE:
<223> OTHER INFORMATION: Rev-Caspase-3 contructed from human caspase -3

<400> SEQUENCE: 34

```
Met Ile Glu Thr Asp Ser Gly Val Asp Asp Met Ala Cys His Lys
1               5                   10                  15

Ile Pro Val Glu Ala Asp Phe Leu Tyr Ala Tyr Ser Thr Ala Pro Gly
                20                  25                  30

Tyr Tyr Ser Trp Arg Asn Ser Lys Asp Gly Ser Trp Phe Ile Gln Ser
            35                  40                  45

Leu Cys Ala Met Leu Lys Gln Tyr Ala Asp Lys Leu Glu Phe Met His
    50                  55                  60

Ile Leu Thr Arg Val Asn Arg Lys Val Ala Thr Glu Phe Glu Ser Phe
65                  70                  75                  80

Ser Phe Asp Ala Thr Phe His Ala Lys Lys Gln Ile Pro Cys Ile Val
                85                  90                  95

Ser Met Leu Thr Lys Glu Leu Tyr Phe Tyr His Asp Glu Val Asp Gly
```

```
            100                 105                 110
Gly Ser Pro Met Glu Asn Thr Glu Asn Ser Val Asp Ser Lys Ser Ile
        115                 120                 125

Lys Asn Leu Glu Pro Lys Ile Ile His Gly Ser Glu Ser Met Asp Ser
130                 135                 140

Gly Ile Ser Leu Asp Asn Ser Tyr Lys Met Asp Tyr Pro Glu Met Gly
145                 150                 155                 160

Leu Cys Ile Ile Ile Asn Asn Lys Asn Phe His Lys Ser Thr Gly Met
                165                 170                 175

Thr Ser Arg Ser Gly Thr Asp Val Asp Ala Ala Asn Leu Arg Glu Thr
            180                 185                 190

Phe Arg Asn Leu Lys Tyr Glu Val Arg Asn Lys Asn Asp Leu Thr Arg
        195                 200                 205

Glu Glu Ile Val Glu Leu Met Arg Asp Val Ser Lys Glu Asp His Ser
    210                 215                 220

Lys Arg Ser Ser Phe Val Cys Val Leu Leu Ser His Gly Glu Glu Gly
225                 230                 235                 240

Ile Ile Phe Gly Thr Asn Gly Pro Val Asp Leu Lys Lys Ile Thr Asn
                245                 250                 255

Phe Phe Arg Gly Asp Arg Cys Arg Ser Leu Thr Gly Lys Pro Lys Leu
            260                 265                 270

Phe Ile Ile Gln Ala Cys Arg Gly Thr Glu Leu Asp Cys Gly Ile Glu
        275                 280                 285

Thr Asp
    290

<210> SEQ ID NO 35
<211> LENGTH: 285
<212> TYPE: PRT
<213> ORGANISM: Artificial Sequence
<220> FEATURE:
<223> OTHER INFORMATION: Uncleavable Rev-Caspase-3 contructed from human
      caspase -3

<400> SEQUENCE: 35

Met Ile Glu Thr Asp Ser Gly Val Asp Asp Met Ala Cys His Lys
1               5                   10                  15

Ile Pro Val Glu Ala Asp Phe Leu Tyr Ala Tyr Ser Thr Ala Pro Gly
            20                  25                  30

Tyr Tyr Ser Trp Arg Asn Ser Lys Asp Gly Ser Trp Phe Ile Gln Ser
        35                  40                  45

Leu Cys Ala Met Leu Lys Gln Tyr Ala Asp Lys Leu Glu Phe Met His
50                  55                  60

Ile Leu Thr Arg Val Asn Arg Lys Val Ala Thr Glu Phe Glu Ser Phe
65                  70                  75                  80

Ser Phe Asp Ala Thr Phe His Ala Lys Lys Gln Ile Pro Cys Ile Val
                85                  90                  95

Ser Met Leu Thr Lys Glu Leu Tyr Phe Tyr His Gly Ser Pro Met Glu
            100                 105                 110

Asn Thr Glu Asn Ser Val Ala Ser Lys Ser Ile Lys Asn Leu Glu Pro
        115                 120                 125

Lys Ile Ile His Gly Ser Glu Ser Met Ala Ser Gly Ile Ser Leu Asp
    130                 135                 140

Asn Ser Tyr Lys Met Asp Tyr Pro Glu Met Gly Leu Cys Ile Ile Ile
145                 150                 155                 160
```

-continued

```
Asn Asn Lys Asn Phe His Lys Ser Thr Gly Met Thr Ser Arg Ser Gly
                165                 170                 175

Thr Asp Val Asp Ala Ala Asn Leu Arg Glu Thr Phe Arg Asn Leu Lys
            180                 185                 190

Tyr Glu Val Arg Asn Lys Asn Asp Leu Thr Arg Glu Ile Val Glu
        195                 200                 205

Leu Met Arg Asp Val Ser Lys Glu Asp His Ser Lys Arg Ser Ser Phe
    210                 215                 220

Val Cys Val Leu Leu Ser His Gly Glu Glu Gly Ile Ile Phe Gly Thr
225                 230                 235                 240

Asn Gly Pro Val Asp Leu Lys Lys Ile Thr Asn Phe Phe Arg Gly Asp
                245                 250                 255

Arg Cys Arg Ser Leu Thr Gly Lys Pro Lys Leu Phe Ile Ile Gln Ala
                260                 265                 270

Cys Arg Gly Thr Glu Leu Asp Cys Gly Ile Glu Thr Asp
            275                 280                 285
```

<210> SEQ ID NO 36
<211> LENGTH: 300
<212> TYPE: PRT
<213> ORGANISM: Artificial Sequence
<220> FEATURE:
<223> OTHER INFORMATION: Rev-Caspase-6 contructed from human caspase-6

<400> SEQUENCE: 36

```
Met Val Glu Ile Asp Ala Ala Ser Val Tyr Thr Leu Pro Ala Gly Ala
1               5                   10                  15

Asp Phe Leu Met Cys Tyr Ser Val Ala Glu Gly Tyr Tyr Ser His Arg
                20                  25                  30

Glu Thr Val Asn Gly Ser Trp Tyr Ile Gln Asp Leu Cys Glu Met Leu
            35                  40                  45

Gly Lys Tyr Gly Ser Ser Leu Glu Phe Thr Glu Leu Leu Thr Leu Val
        50                  55                  60

Asn Arg Lys Val Ser Gln Arg Val Asp Phe Cys Lys Asp Pro Ser
65                  70                  75                  80

Ala Ile Gly Lys Lys Gln Val Pro Cys Phe Ala Ser Met Leu Thr Lys
                85                  90                  95

Lys Leu His Phe Phe Pro Lys Ser Asn Leu Glu His His His His His
                100                 105                 110

His Val Glu Ile Asp Gly Gly Ser Pro Met Ser Ala Ser Gly Leu
            115                 120                 125

Arg Arg Gly His Pro Ala Gly Gly Glu Glu Asn Met Thr Glu Thr Asp
    130                 135                 140

Ala Phe Tyr Lys Arg Glu Met Phe Asp Pro Ala Glu Lys Tyr Lys Met
145                 150                 155                 160

Asp His Arg Arg Arg Gly Ile Ala Leu Ile Phe Asn His Glu Arg Phe
                165                 170                 175

Phe Trp His Leu Thr Leu Pro Glu Arg Arg Gly Thr Cys Ala Asp Arg
                180                 185                 190

Asp Asn Leu Thr Arg Arg Phe Ser Asp Leu Gly Phe Glu Val Lys Cys
            195                 200                 205

Phe Asn Asp Leu Lys Ala Glu Glu Leu Leu Leu Lys Ile His Glu Val
    210                 215                 220

Ser Thr Val Ser His Ala Asp Ala Asp Cys Phe Val Cys Val Phe Leu
225                 230                 235                 240
```

```
Ser His Gly Glu Gly Asn His Ile Tyr Ala Tyr Asp Ala Lys Ile Glu
                245                 250                 255

Ile Gln Thr Leu Thr Gly Leu Phe Lys Gly Asp Lys Cys His Ser Leu
            260                 265                 270

Val Gly Lys Pro Lys Ile Phe Ile Ile Gln Ala Cys Arg Gly Asn Gln
        275                 280                 285

His Asp Val Pro Val Ile Pro Leu Asp Val Val Asp
    290                 295                 300

<210> SEQ ID NO 37
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase
<221> NAME/KEY: VARIANT
<222> LOCATION: (1)...(5)
<223> OTHER INFORMATION: Xaa = Any Amino Acid

<400> SEQUENCE: 37

Asp Xaa Xaa Asp Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase

<400> SEQUENCE: 38

Asp Glu Val Asp Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase

<400> SEQUENCE: 39

Ile Glu Thr Asp Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase

<400> SEQUENCE: 40

Tyr Val Ala Asp Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase
```

```
<400> SEQUENCE: 41

Tyr Val His Asp Gly
 1               5

<210> SEQ ID NO 42
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase

<400> SEQUENCE: 42

Trp Glu His Asp Gly
 1               5

<210> SEQ ID NO 43
<211> LENGTH: 22
<212> TYPE: DNA
<213> ORGANISM: Artificial Sequence
<220> FEATURE:
<223> OTHER INFORMATION: PCR primer for large subunit of caspase-3

<400> SEQUENCE: 43
atggagaaca ctgaaaactc ag                                          22

<210> SEQ ID NO 44
<211> LENGTH: 22
<212> TYPE: DNA
<213> ORGANISM: Artificial Sequence
<220> FEATURE:
<223> OTHER INFORMATION: PCR primer for large subunit of caspase-3

<400> SEQUENCE: 44
gtcatcatca cacctcagt ct                                           22

<210> SEQ ID NO 45
<211> LENGTH: 26
<212> TYPE: DNA
<213> ORGANISM: Artificial Sequence
<220> FEATURE:
<223> OTHER INFORMATION: PCR primer for small subunit of caspase-3

<400> SEQUENCE: 45
ggatccatga ttgagacaga cagtgg                                      26

<210> SEQ ID NO 46
<211> LENGTH: 30
<212> TYPE: DNA
<213> ORGANISM: Artificial Sequence
<220> FEATURE:
<223> OTHER INFORMATION: PCR primer for small subunit of caspase-3

<400> SEQUENCE: 46
atcaacttca tcgtgataaa aatagagttc                                  30

<210> SEQ ID NO 47
<211> LENGTH: 18
<212> TYPE: DNA
<213> ORGANISM: Artificial Sequence
<220> FEATURE:
<223> OTHER INFORMATION: PCR primer for large subunit of caspase-6

<400> SEQUENCE: 47
atgagctcgg cctcgggg                                               18
```

```
<210> SEQ ID NO 48
<211> LENGTH: 21
<212> TYPE: DNA
<213> ORGANISM: Artificial Sequence
<220> FEATURE:
<223> OTHER INFORMATION: PCR primer for large subunit of caspase-6

<400> SEQUENCE: 48
ttaatctact acatccaaag g                                           21

<210> SEQ ID NO 49
<211> LENGTH: 36
<212> TYPE: DNA
<213> ORGANISM: Artificial Sequence
<220> FEATURE:
<223> OTHER INFORMATION: PCR primer for small subunit of caspase-6

<400> SEQUENCE: 49
ggatccatgg tagaaataga tgcagcctcc gtttac                           36

<210> SEQ ID NO 50
<211> LENGTH: 30
<212> TYPE: DNA
<213> ORGANISM: Artificial Sequence
<220> FEATURE:
<223> OTHER INFORMATION: PCR primer for small subunit of caspase-6

<400> SEQUENCE: 50
atcaattcaa cgtggtggtg gtggtggtgc                                  30

<210> SEQ ID NO 51
<211> LENGTH: 5
<212> TYPE: PRT
<213> ORGANISM: Homo sapien
<220> FEATURE:
<221> NAME/KEY: VARIANT
<222> LOCATION: (1)...(5)
<223> OTHER INFORMATION: Xaa = Any Amino Acid

<400> SEQUENCE: 51

Gln Ala Cys Xaa Gly
 1               5

<210> SEQ ID NO 52
<211> LENGTH: 4
<212> TYPE: PRT
<213> ORGANISM: Homo Sapien

<400> SEQUENCE: 52

Asp Glu Val Asp
 1

<210> SEQ ID NO 53
<211> LENGTH: 4
<212> TYPE: PRT
<213> ORGANISM: Homo sapien

<400> SEQUENCE: 53

Ile Glu Thr Asp
 1

<210> SEQ ID NO 54
<211> LENGTH: 6
<212> TYPE: PRT
<213> ORGANISM: Homo sapien
```

<400> SEQUENCE: 54

Arg Thr Arg Thr Gly Ser
1               5

<210> SEQ ID NO 55
<211> LENGTH: 6
<212> TYPE: PRT
<213> ORGANISM: Homo sapien

<400> SEQUENCE: 55

Leu Ser His Gly Cys Gln
1               5

<210> SEQ ID NO 56
<211> LENGTH: 9
<212> TYPE: PRT
<213> ORGANISM: Homo sapien

<400> SEQUENCE: 56

Phe Ile Gln Ala Cys Gly Gly Glu Gln
1               5

<210> SEQ ID NO 57
<211> LENGTH: 5
<212> TYPE: PRT
<213> ORGANISM: Homo sapien

<400> SEQUENCE: 57

Pro Glu Pro Asp Ala
1               5

<210> SEQ ID NO 58
<211> LENGTH: 5
<212> TYPE: PRT
<213> ORGANISM: Homo sapien

<400> SEQUENCE: 58

Asp Gln Leu Asp Ala
1               5

<210> SEQ ID NO 59
<211> LENGTH: 15
<212> TYPE: PRT
<213> ORGANISM: Homo sapien

<400> SEQUENCE: 59

Gly Phe Val Ser Trp Arg Asp Pro Lys Ser Gly Ser Trp Tyr Val
1               5                   10                  15

<210> SEQ ID NO 60
<211> LENGTH: 6
<212> TYPE: PRT
<213> ORGANISM: Homo sapien

<400> SEQUENCE: 60

Arg Asp Arg Asn Gly Thr
1               5

<210> SEQ ID NO 61
<211> LENGTH: 6
<212> TYPE: PRT
<213> ORGANISM: Homo sapien

<400> SEQUENCE: 61

```
Leu Ser His Gly Asp Lys
  1               5
```

<210> SEQ ID NO 62
<211> LENGTH: 9
<212> TYPE: PRT
<213> ORGANISM: Homo sapien

<400> SEQUENCE: 62

```
Phe Ile Gln Ala Cys Gln Gly Asp Asn
  1               5
```

<210> SEQ ID NO 63
<211> LENGTH: 5
<212> TYPE: PRT
<213> ORGANISM: Homo sapien

<400> SEQUENCE: 63

```
Val Glu Thr Asp Ser
  1               5
```

<210> SEQ ID NO 64
<211> LENGTH: 5
<212> TYPE: PRT
<213> ORGANISM: Homo sapien

<400> SEQUENCE: 64

```
Leu Glu Met Asp Leu
  1               5
```

<210> SEQ ID NO 65
<211> LENGTH: 15
<212> TYPE: PRT
<213> ORGANISM: Homo sapien

<400> SEQUENCE: 65

```
Asn Cys Val Ser Tyr Arg Asn Pro Ala Glu Gly Thr Trp Tyr Ile
  1               5                  10                  15
```

<210> SEQ ID NO 66
<211> LENGTH: 6
<212> TYPE: PRT
<213> ORGANISM: Homo sapien

<400> SEQUENCE: 66

```
Lys Asp Arg Gln Gly Thr
  1               5
```

<210> SEQ ID NO 67
<211> LENGTH: 6
<212> TYPE: PRT
<213> ORGANISM: Homo sapien

<400> SEQUENCE: 67

```
Leu Thr His Gly Arg Phe
  1               5
```

<210> SEQ ID NO 68
<211> LENGTH: 9
<212> TYPE: PRT
<213> ORGANISM: Homo sapien

<400> SEQUENCE: 68

```
Phe Ile Gln Ala Cys Gln Gly Glu Glu
```

-continued

<210> SEQ ID NO 69
<211> LENGTH: 5
<212> TYPE: PRT
<213> ORGANISM: Homo sapien

<400> SEQUENCE: 69

Ile Glu Ala Asp Ala
1               5

<210> SEQ ID NO 70
<211> LENGTH: 15
<212> TYPE: PRT
<213> ORGANISM: Homo sapien

<400> SEQUENCE: 70

Gly Tyr Val Ser Phe Arg His Val Glu Glu Gly Ser Trp Tyr Ile
1               5                   10                  15

<210> SEQ ID NO 71
<211> LENGTH: 6
<212> TYPE: PRT
<213> ORGANISM: Homo sapien

<400> SEQUENCE: 71

Gly Val Arg Asn Gly Thr
1               5

<210> SEQ ID NO 72
<211> LENGTH: 6
<212> TYPE: PRT
<213> ORGANISM: Homo sapien

<400> SEQUENCE: 72

Leu Ser His Gly Glu Glu
1               5

<210> SEQ ID NO 73
<211> LENGTH: 9
<212> TYPE: PRT
<213> ORGANISM: Homo sapien

<400> SEQUENCE: 73

Phe Ile Gln Ala Cys Arg Gly Thr Glu
1               5

<210> SEQ ID NO 74
<211> LENGTH: 5
<212> TYPE: PRT
<213> ORGANISM: Homo sapien

<400> SEQUENCE: 74

Ile Gln Ala Asp Ser
1               5

<210> SEQ ID NO 75
<211> LENGTH: 15
<212> TYPE: PRT
<213> ORGANISM: Homo sapien

<400> SEQUENCE: 75

Gly Tyr Tyr Ser Trp Arg Ser Pro Gly Arg Gly Ser Trp Phe Val
1               5                   10                  15

<210> SEQ ID NO 76
<211> LENGTH: 6
<212> TYPE: PRT
<213> ORGANISM: Homo sapien

<400> SEQUENCE: 76

Pro Glu Arg Arg Gly Thr
1               5

<210> SEQ ID NO 77
<211> LENGTH: 6
<212> TYPE: PRT
<213> ORGANISM: Homo sapien

<400> SEQUENCE: 77

Leu Ser His Gly Glu Gly
1               5

<210> SEQ ID NO 78
<211> LENGTH: 9
<212> TYPE: PRT
<213> ORGANISM: Homo sapien

<400> SEQUENCE: 78

Ile Ile Gln Ala Cys Arg Gly Asn Gln
1               5

<210> SEQ ID NO 79
<211> LENGTH: 5
<212> TYPE: PRT
<213> ORGANISM: Homo sapien

<400> SEQUENCE: 79

Asp Val Val Asp Asn
1               5

<210> SEQ ID NO 80
<211> LENGTH: 5
<212> TYPE: PRT
<213> ORGANISM: Homo sapien

<400> SEQUENCE: 80

Thr Glu Val Asp Ala
1               5

<210> SEQ ID NO 81
<211> LENGTH: 15
<212> TYPE: PRT
<213> ORGANISM: Homo sapien

<400> SEQUENCE: 81

Gly Tyr Tyr Ser His Arg Glu Thr Val Asn Gly Ser Trp Tyr Ile
1               5                   10                  15

<210> SEQ ID NO 82
<211> LENGTH: 6
<212> TYPE: PRT
<213> ORGANISM: Homo sapien

<400> SEQUENCE: 82

Thr Ser Arg Ser Gly Thr
1               5

<210> SEQ ID NO 83

```
<211> LENGTH: 6
<212> TYPE: PRT
<213> ORGANISM: Homo sapien

<400> SEQUENCE: 83

Leu Ser His Gly Glu Glu
 1               5

<210> SEQ ID NO 84
<211> LENGTH: 9
<212> TYPE: PRT
<213> ORGANISM: Homo sapien

<400> SEQUENCE: 84

Ile Ile Gln Ala Cys Arg Gly Thr Glu
 1               5

<210> SEQ ID NO 85
<211> LENGTH: 5
<212> TYPE: PRT
<213> ORGANISM: Homo sapien

<400> SEQUENCE: 85

Ile Glu Thr Asp Ser
 1               5

<210> SEQ ID NO 86
<211> LENGTH: 15
<212> TYPE: PRT
<213> ORGANISM: Homo sapien

<400> SEQUENCE: 86

Gly Tyr Tyr Ser Trp Arg Asn Ser Lys Asp Gly Ser Trp Phe Ile
 1               5                  10                  15

<210> SEQ ID NO 87
<211> LENGTH: 6
<212> TYPE: PRT
<213> ORGANISM: Homo sapien

<400> SEQUENCE: 87

Pro Thr Arg Asn Gly Thr
 1               5

<210> SEQ ID NO 88
<211> LENGTH: 6
<212> TYPE: PRT
<213> ORGANISM: Homo sapien

<400> SEQUENCE: 88

Leu Ser His Gly Glu Glu
 1               5

<210> SEQ ID NO 89
<211> LENGTH: 9
<212> TYPE: PRT
<213> ORGANISM: Homo sapien

<400> SEQUENCE: 89

Phe Val Gln Ala Cys Arg Gly Glu Arg
 1               5

<210> SEQ ID NO 90
<211> LENGTH: 5
<212> TYPE: PRT
```

-continued

```
<213> ORGANISM: Homo sapien

<400> SEQUENCE: 90

Asp Ser Val Asp Gly
 1               5

<210> SEQ ID NO 91
<211> LENGTH: 15
<212> TYPE: PRT
<213> ORGANISM: Homo sapien

<400> SEQUENCE: 91

Gln Tyr Val Ser Trp Arg Asn Ser Ala Arg Gly Ser Trp Phe Ile
 1               5                  10                  15

<210> SEQ ID NO 92
<211> LENGTH: 6
<212> TYPE: PRT
<213> ORGANISM: Homo sapien

<400> SEQUENCE: 92

Pro Arg Arg Thr Gly Ala
 1               5

<210> SEQ ID NO 93
<211> LENGTH: 6
<212> TYPE: PRT
<213> ORGANISM: Homo sapien

<400> SEQUENCE: 93

Met Ser His Gly Ile Arg
 1               5

<210> SEQ ID NO 94
<211> LENGTH: 9
<212> TYPE: PRT
<213> ORGANISM: Homo sapien

<400> SEQUENCE: 94

Ile Ile Gln Ala Cys Arg Gly Asp Ser
 1               5

<210> SEQ ID NO 95
<211> LENGTH: 5
<212> TYPE: PRT
<213> ORGANISM: Homo sapien

<400> SEQUENCE: 95

Trp Phe Lys Asp Ser
 1               5

<210> SEQ ID NO 96
<211> LENGTH: 5
<212> TYPE: PRT
<213> ORGANISM: Homo sapien

<400> SEQUENCE: 96

Phe Glu Asp Asp Ala
 1               5

<210> SEQ ID NO 97
<211> LENGTH: 15
<212> TYPE: PRT
<213> ORGANISM: Homo sapien
```

-continued

<400> SEQUENCE: 97

Asp Asn Val Ser Trp Arg His Pro Thr Met Gly Ser Val Phe Ile
1               5                   10                  15

<210> SEQ ID NO 98
<211> LENGTH: 6
<212> TYPE: PRT
<213> ORGANISM: Homo sapien

<400> SEQUENCE: 98

Pro Pro Arg Asn Gly Ala
1               5

<210> SEQ ID NO 99
<211> LENGTH: 6
<212> TYPE: PRT
<213> ORGANISM: Homo sapien

<400> SEQUENCE: 99

Met Ser His Gly Ile Leu
1               5

<210> SEQ ID NO 100
<211> LENGTH: 9
<212> TYPE: PRT
<213> ORGANISM: Homo sapien

<400> SEQUENCE: 100

Ile Val Gln Ala Cys Arg Gly Ala Asn
1               5

<210> SEQ ID NO 101
<211> LENGTH: 5
<212> TYPE: PRT
<213> ORGANISM: Homo sapien

<400> SEQUENCE: 101

Trp Val Lys Asp Ser
1               5

<210> SEQ ID NO 102
<211> LENGTH: 5
<212> TYPE: PRT
<213> ORGANISM: Homo sapien

<400> SEQUENCE: 102

Leu Glu Glu Asp Ala
1               5

<210> SEQ ID NO 103
<211> LENGTH: 15
<212> TYPE: PRT
<213> ORGANISM: Homo sapien

<400> SEQUENCE: 103

His Asn Val Ser Trp Arg Asp Ser Thr Met Gly Ser Ile Phe Ile
1               5                   10                  15

<210> SEQ ID NO 104
<211> LENGTH: 6
<212> TYPE: PRT
<213> ORGANISM: Homo sapien

<400> SEQUENCE: 104

```
Pro Ala Arg Asn Gly Ala
 1               5

<210> SEQ ID NO 105
<211> LENGTH: 6
<212> TYPE: PRT
<213> ORGANISM: Homo sapien

<400> SEQUENCE: 105

Met Ser His Gly Ile Leu
 1               5

<210> SEQ ID NO 106
<211> LENGTH: 9
<212> TYPE: PRT
<213> ORGANISM: Homo sapien

<400> SEQUENCE: 106

Ile Val Gln Ala Cys Arg Gly Glu Lys
 1               5

<210> SEQ ID NO 107
<211> LENGTH: 5
<212> TYPE: PRT
<213> ORGANISM: Homo sapien

<400> SEQUENCE: 107

Trp Val Arg Asp Ser
 1               5

<210> SEQ ID NO 108
<211> LENGTH: 5
<212> TYPE: PRT
<213> ORGANISM: Homo sapien

<400> SEQUENCE: 108

Leu Glu Ala Asp Ser
 1               5

<210> SEQ ID NO 109
<211> LENGTH: 15
<212> TYPE: PRT
<213> ORGANISM: Homo sapien

<400> SEQUENCE: 109

His Asn Val Ser Trp Arg Asp Arg Thr Arg Gly Ser Ile Phe Ile
 1               5                  10                  15

<210> SEQ ID NO 110
<211> LENGTH: 6
<212> TYPE: PRT
<213> ORGANISM: Homo sapien

<400> SEQUENCE: 110

Glu Phe Arg Ser Gly Gly
 1               5

<210> SEQ ID NO 111
<211> LENGTH: 6
<212> TYPE: PRT
<213> ORGANISM: Homo sapien

<400> SEQUENCE: 111

Leu Ser His Gly Val Glu
 1               5
```

-continued

```
<210> SEQ ID NO 112
<211> LENGTH: 9
<212> TYPE: PRT
<213> ORGANISM: Homo sapien

<400> SEQUENCE: 112

Phe Ile Gln Ala Cys Arg Gly Asp Glu
 1               5

<210> SEQ ID NO 113
<211> LENGTH: 5
<212> TYPE: PRT
<213> ORGANISM: Homo sapien

<400> SEQUENCE: 113

Asp Gln Gln Asp Gly
 1               5

<210> SEQ ID NO 114
<211> LENGTH: 5
<212> TYPE: PRT
<213> ORGANISM: Homo sapien

<400> SEQUENCE: 114

Glu Glu Ser Asp Ala
 1               5

<210> SEQ ID NO 115
<211> LENGTH: 15
<212> TYPE: PRT
<213> ORGANISM: Homo sapien

<400> SEQUENCE: 115

Gly Thr Ala Ala Met Arg Asn Thr Lys Arg Gly Ser Trp Tyr Ile
 1               5                  10                  15

<210> SEQ ID NO 116
<211> LENGTH: 5
<212> TYPE: PRT
<213> ORGANISM: Artificial Sequence
<220> FEATURE:
<223> OTHER INFORMATION: Protease sensitive linker region between the
      small and large subunits of a Rev-caspase

<400> SEQUENCE: 116

Val Glu Ile Asp Ser
 1               5
```